US009688717B2

(12) United States Patent
Cheng et al.

(10) Patent No.: US 9,688,717 B2
(45) Date of Patent: Jun. 27, 2017

(54) RAMAN TAG

(71) Applicant: Purdue Research Foundation, West Lafayette, IN (US)

(72) Inventors: Ji-xin Cheng, West Lafayette, IN (US); Mingji Dai, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 14/850,949

(22) Filed: Sep. 10, 2015

(65) Prior Publication Data

US 2016/0068562 A1 Mar. 10, 2016

Related U.S. Application Data

(60) Provisional application No. 62/048,484, filed on Sep. 10, 2014.

(51) Int. Cl.

| | |
|---|---|
| ***C07J 9/00*** | (2006.01) |
| ***G01N 33/52*** | (2006.01) |
| ***C07J 17/00*** | (2006.01) |
| ***C07J 41/00*** | (2006.01) |

(52) U.S. Cl.
CPC ................ *C07J 9/00* (2013.01); *C07J 9/005* (2013.01); *C07J 17/00* (2013.01); *C07J 41/0094* (2013.01); *G01N 33/52* (2013.01)

(58) Field of Classification Search
CPC .................................. C07J 9/00; G01N 33/52
See application file for complete search history.

(56) References Cited

PUBLICATIONS

Peyrot et al, The Journal of Biological Chemistry, Tracking the Subcellular Fate of 20(S)-Hydroxycholesterol with Click Chemistry Reveals a Transport Pathway to the Golgi, 2014, 289(16), pp. 11095-11110.*

Yamakoshi et al, Journal of the American Chemical Society, Alkyne-Tag Raman Imaging for Visualization of Mobile Small Molecules in Live Cells, 2012, 134, pp. 20681-20689.*

* cited by examiner

*Primary Examiner* — Paul A Zucker

(74) *Attorney, Agent, or Firm* — Purdue Research Foundation; Yonghao Hou

(57) ABSTRACT

The present invention provides novel Raman tags for exploring membrane interactions in cells. The tags comprise a phenyl diyne probe where in the dyine is capped with the phenyl group. Methods for using the tags are also provided.

6 Claims, 42 Drawing Sheets

S1

$^1$H NMR of S1 (500 MHz, $CDCl_3$)

S1

$^{13}C$ NMR of S1 (100 MHz, $CDCl_3$)

$^1$H NMR of S2 (400 MHz, $CDCl_3$)

S2

$^{13}C$ NMR of S2 (100 MHz, $CDCl_3$)

$^1$H NMR of S3 (400 MHz, $CDCl_3$)

$^{13}C$ NMR of S3 (100 MHz, $CDCl_3$)

$^1$H NMR of 4 (500 MHz, $CDCl_3$)

$^{13}C$ NMR of 4 (125 MHz, $CDCl_3$)

$^1$H NMR of 5 (400 MHz, CDCl$_3$)

$^{13}C$ NMR of 5 (100 MHz, $CDCl_3$)

S4

$^1$H NMR of S4 (400 MHz, $CDCl_3$)

S4

$^{13}C$ NMR of S4 (125 MHz, $CDCl_3$)

$^1H$ NMR of S5 (500 MHz, $CDCl_3$)

S5

$^{13}C$ NMR of S5 (125 MHz, $CDCl_3$)

$^1H$ NMR of 8 (400 MHz, $CDCl_3$)

$^{13}C$ NMR of 8 (100 MHz, $CDCl_3$)

S6

$^1$H NMR of S6 (400 MHz, $CDCl_3$)

S6

$^{13}C$ NMR of S6 (100 MHz, $CDCl_3$)

$^{1}H$ NMR of 6 (400 MHz, $CDCl_3$)

6

$^{13}C$ NMR of 6 (100 MHz, $CDCl_3$)

S7

$^{1}$H NMR of S7 (400 MHz, CDCl$_3$)

S7

$^{13}C$ NMR of S7 (100 MHz, $CDCl_3$)

$^1$H NMR of 7 (400 MHz, $CDCl_3$)

$^{13}C$ NMR of 7 (100 MHz, $CDCl_3$)

$^1H$ NMR of S8 (500 MHz, $CDCl_3$)

S8

$^{13}$C NMR of S8 (100 MHz, $CDCl_3$)

$^1$H NMR of 8 (400 MHz, $CDCl_3$)

$^{13}C$ NMR of 8 (125 MHz, $CDCl_3$)

RAMAN TAG

This invention was made with government support under CA182608 awarded by the National Institutes of Health. The government has certain rights in the invention.

TECHNICAL FIELD

The present disclosure generally relates to tags for imaging molecules using Raman spectroscopy, and in particular to a method and composition that uses cholesterol mimics to track the location and movement of cholesterol.

BACKGROUND

This section introduces aspects that may help facilitate a better understanding of the disclosure. Accordingly, these statements are to be read in this light and are not to be understood as admissions about what is or is not prior art.

An important component of cellular membrane, cholesterol controls physical properties of the membrane and contributes to specific membrane structures such as lipid rafts. Inside cells, cholesterol plays an important role in various signaling pathways and serves as the precursor for signaling molecules, and modifies specific proteins, such as hedgehog, to control protein trafficking and activity. The distribution of cholesterol in a living cell is highly regulated. Intracellular cholesterol is stored in lipid droplets (LDs) in the form of cholesteryl ester to avoid the toxicity caused by free cholesterol. Dysregulation of cholesterol metabolism and/or trafficking has been linked to various diseases, including atherosclerosis, Niemann-Pick type C (NP-C) disease, and various cancers.

Intracellular cholesterol transport and metabolism have been studied extensively using various reporter molecules, including cholesterol binding molecules and cholesterol analogs. Cholesterol binding molecules, such as cholesterol oxidase, filipin, and perfringolysin O derivatives, are commonly used to study steady-state distribution of cholesterol in fixed cells and tissues. Fluorescent cholesterol, including intrinsic fluorescent sterols (DHE for dehydroergosterol) and fluorophore-tagged analogs (NBD-cholesterol and BODIPY-cholesterol) are widely used in vitro and in vivo. Radiolabeled cholesterol or its precursors are used in biochemical studies of metabolism and trafficking of cholesterol.

These current cholesterol assays have limitations. Cholesterol oxidase is commonly used in fluorometric or colorimetric assays to quantify total cholesterol in homogenized cells. Radiolabeled cholesterol has to be used in combination with separation methods to determine intracellular cholesterol distribution indirectly. For imaging purpose, filipin is the most commonly used molecule for visualizing distribution of free cholesterol, but it is only applicable to fixed cells or tissues with moderate specificity because filipin also labels other lipids. Fluorescent BODIPY-cholesterol is known to cause perturbations due to bulkiness of the fluorophore. DHE has the closest structure as cholesterol, but its fluorescence undergoes rapid photo-bleaching, which impedes real-time observation of cholesterol trafficking There exists a need for new technologies that allow for real time imaging of cholesterol transport and low toxicity in live cells.

SUMMARY OF THE INVENTION

The present invention provides novel Raman tags for exploring membrane interactions in cells. The tags comprise a phenyl diyne probe where in the dyine is capped with the phenyl group. Methods for using the tags are also provided.

(b) Schematic graph showing the hypothesis of PhDY-Chol metabolism inside the cells. ACAT-1: Acyl-CoA:cholesterol acyltransferase. (c) SRS images of PhDY-Chol in CHO cells and ACAT-1 inhibited CHO cells by avasimibe treatment. As shown in circles, PhDY-Chol was stored in LDs in CHO cells, but not in avasimibe treated CHO cells. Image acquisition speed: 100 μs per pixel for 400×400 pixels. Scalar bar: 10 μm. Intensity bars in a and c show the ΔI/I of the SRS image. (d) Quantification of PhDY-rich and BODIPY-rich LDs in CHO cells before and after ACAT-1 inhibition. The number of the LDs was normalized by the control group (n=7). Error bars represent standard deviation. *: $p<0.05$. (e) TPEF images of BODIPY-cholesterol and SRS images C—H-rich structures in CHO cells and ACAT-1 inhibited CHO cells. As shown in circles, BODIPY-cholesterol showed no difference between the two groups. Scalar bar: 10 μm.

Figure 5:
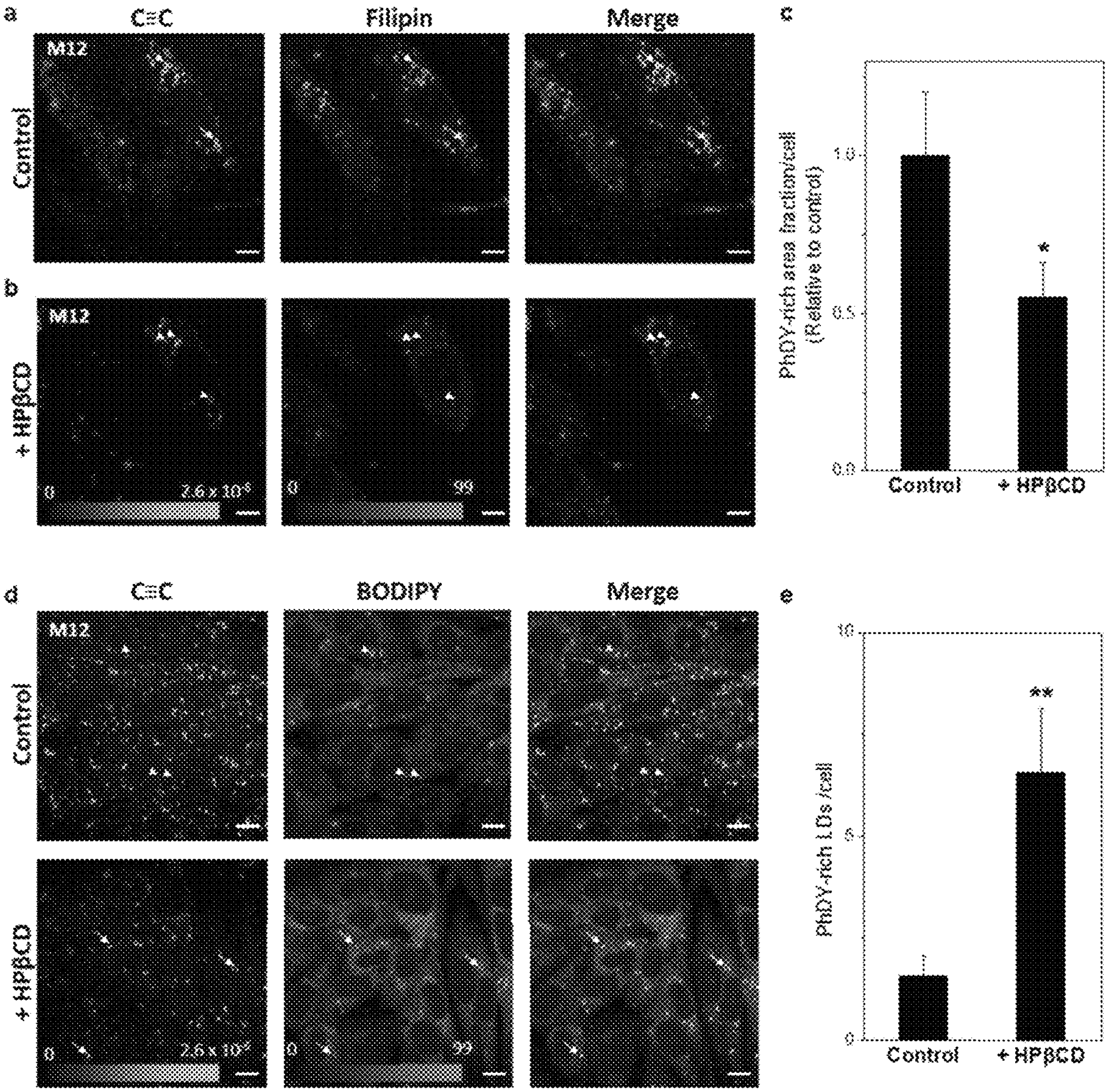

FIG. 5. Restored cholesterol transport in M12 cells treated with HPβCD. TPEF images of filipin and SRS images PhDY-Chol in (a) PhDY-Chol-loaded M12 cells, and (b) the same cells treated with HPβCD (500 μM) for 30 h. Arrows indicate PhDY-rich area labeled by filipin before treatment (non-esterified PhDY-Chol), and arrow heads indicate PhDY-rich area not labeled by filipin after treatment (esterified PhDY-Chol). Green intensity bar shows the ΔI/I value of the SRS image; red intensity bar represents the relative intensity of fluorescence. Image acquisition speed: 100 μs per pixel for 400×400 pixels. Scalar bar: 10 μm. (c) Quantification of PhDY-rich area in the cells before and after HPβCD treatment (n=7). Error bars represent standard deviation. *: $p<0.05$. (d) TPEF images of BODIPY and SRS images of PhDY-Chol in M12 cells treated with or without HPβCD (500 μM) for 30 h. Arrow heads indicate LDs without PhDY-Chol before treatment, and arrows indicate LDs with PhDY-Chol after treatment. Green intensity bar shows the ΔI/I value of the SRS image; red intensity bar represents the relative intensity of fluorescence. Image acquisition speed: 100 μs per pixel for 400×400 pixels. Scalar bar: 10 μm. (e) Quantification of PhDY-rich LDs in the cells before and after HPβCD treatment (n=7). Error bars represent standard deviation. ** : $p<0.005$.

Figure 6:
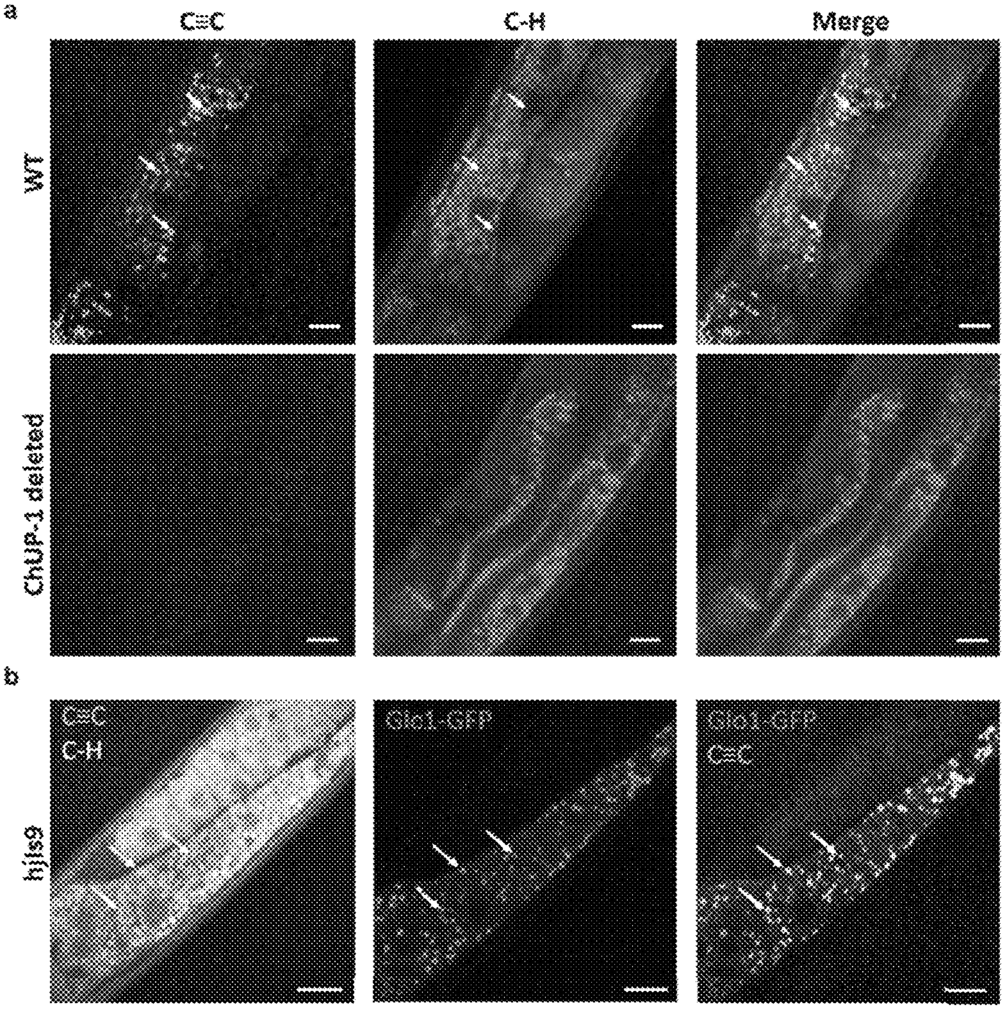

FIG. 6. SRS imaging of PhDY-Chol visualizes compartments of cholesterol storage in live *C. elegans*. (a) SRS images of live wildtype and ChUP-1 deleted *C. elegans* fed with PhDY-Chol (500 μM) for 3 days. Arrows indicate PhDY-rich particles in the intestine. Image acquisition speed: 10 μs per pixel for 400×400 pixels. Scalar bar: 10 μm. (b) TPEF and SRS images of live hjIs9 [ges-1p::glo-1::GFP+unc-119(+)] worm fed with PhDY-Chol (500 μM) for 3 days. Arrows indicate the PhDY-rich particles in LROs. Image acquisition speed: 10 μs per pixel for 400×400 pixels. Scalar bar: 10 μm.

Figure 7:
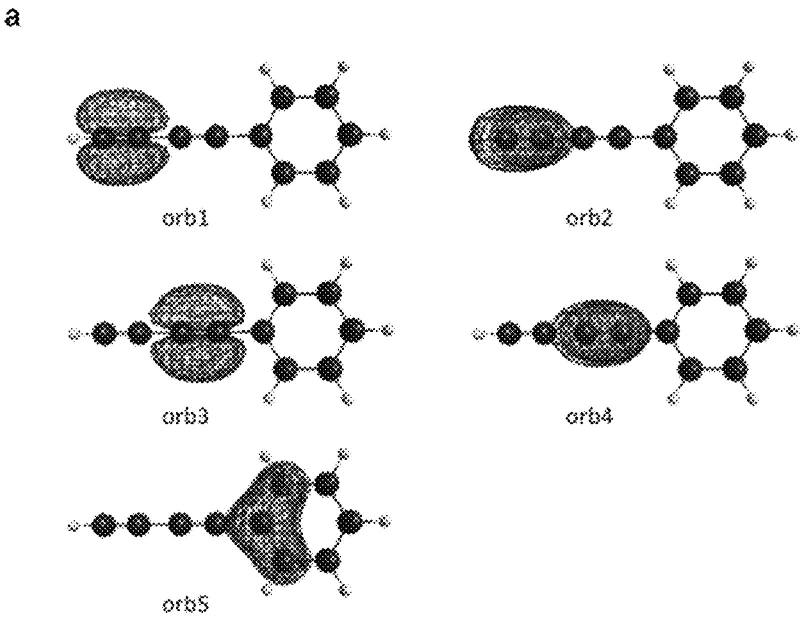
Figure 7:
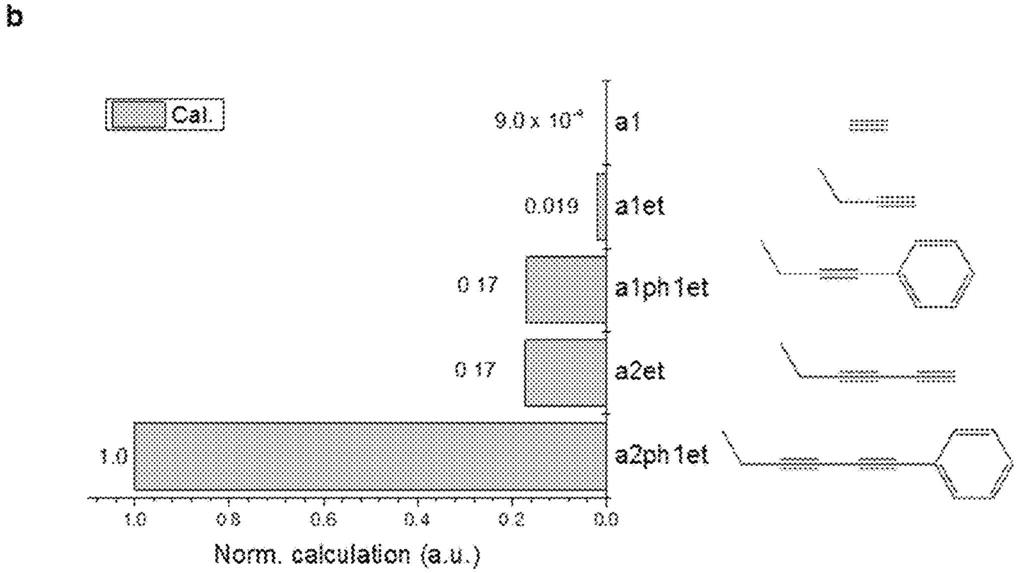

FIG. 7. Theoretical Raman intensities of the C≡C stretching mode in various tags. The total molecular polarizability is broken down in terms of the value of the polarizability corresponding to each bond in the molecule. The Raman scattering cross section arises from the polarizability caused by conjugation of the π-electrons of the alkyne and the phenyl groups. The π-orbitals possess large polarizability tensors, such that the polarizability of the triple bond is mainly determined by the polarizability of π-orbitals. (a) Depiction of symmetry-localized π-orbitals in $C_4H—C_6H_5$ (C≡C—C≡C—Ph). The distributed polarizabilities corresponding to the localized orbitals on C≡C and phenyl ring are shown in Supplementary Table 1, such that the polarizabilities of orbitals 1 and 2 determine the total polarizability of the left C≡C bond, polarizabilities of orbitals 3 and 4 sum up to the polarizability of the middle C≡C bond. Additionally, the closest to alkyne part of the ring (orbital 5) exhibits significant change in polarizability along triple-bond stretching vibration, and therefore polarizabilities corresponding to this orbital are included in the total count of polarizability of the triple-bond system. Distributed polarizabilities are calculated using GAMESS electronic structure package[1]. (b) Comparison of C≡C stretching Raman intensities in various tags computed using the Q-Chem quantum chemistry software[2]. Intensities were normalized to the highest intensity.

Figure 8:
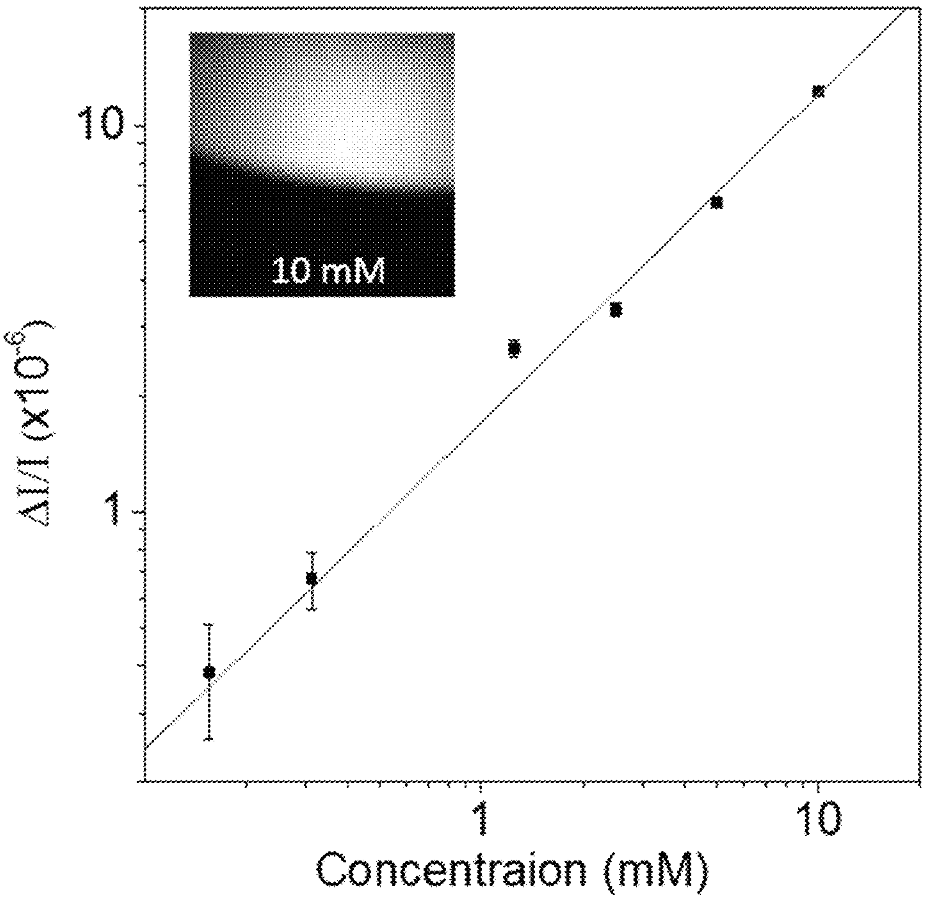

FIG. 8. Linear correlation between PhDY-Chol concentration and modulation depth. Concentration of PhDY-Chol and modulation depth (ΔI/I) show linear correlation, which can be expressed as: $y=0.85x-5.77$ ($R^2=0.98$). Inset is an SRS image of 10 mM PhDY-Chol in cyclohexanone. Data acquisition speed: 200 μs per pixel. Error bars represent standard errors.

Figure 9:
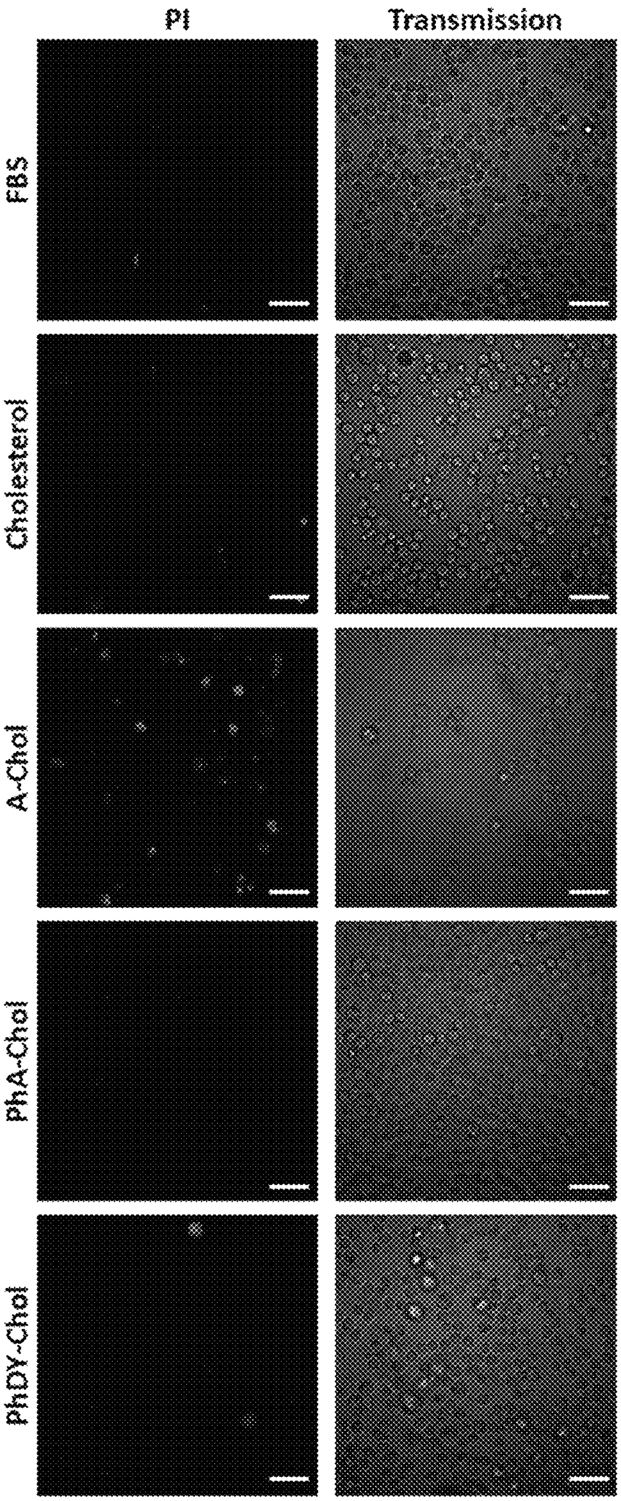

FIG. 9. Phenyl group prevented cytotoxicity of the probe molecules. Propidium iodide staining show that alkyne-cholesterol induces apoptosis and necrosis. Transmission images show reduced cell number in alkyne-cholesterol treated CHO cells. Phenyl group prevented the cytotoxic effect. A-Chol: alkyne cholesterol; PhA-Chol: phenyl-alkyne cholesterol; PhDY-Chol: phenyl-diyne cholesterol; PI: propidium iodide. Scalar bar: 50 μm.

Figure 10:
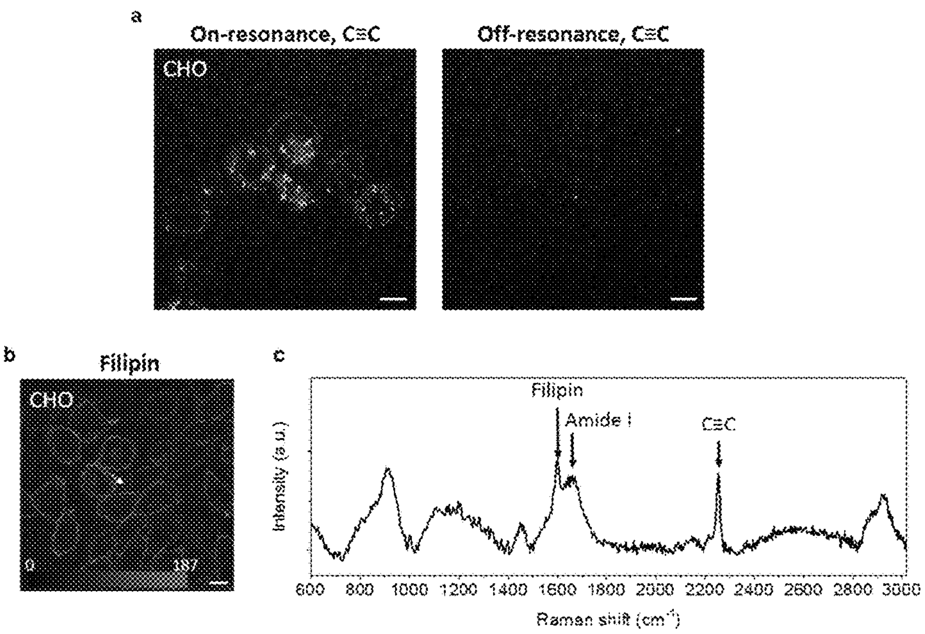

FIG. 10. PhDY-Chol is incorporated into cellular membrane. (a) SRS images of live CHO cells. Cells were trypsinized and suspended in medium. PhDY-Chol was seen in plasma membrane and intracellular structures. Data acquisition time: 10 μs per pixel for 800×800 pixels. Scalar bar: 10 μm. (b) TPEF image of filipin-labeled CHO cells. Arrow indicates the point used for Raman spectral analysis. Red intensity bar represents the relative intensity of fluorescence. Scalar bar: 10 μm. (c) Raman spectrum of filipin-labeled cell membrane acquired on the same TPEF microscope. The bands for filipin, protein (amide I), and C≡C vibrational mode are indicated by black arrows. Spectrum acquisition time: 30 s.

Figure 11:
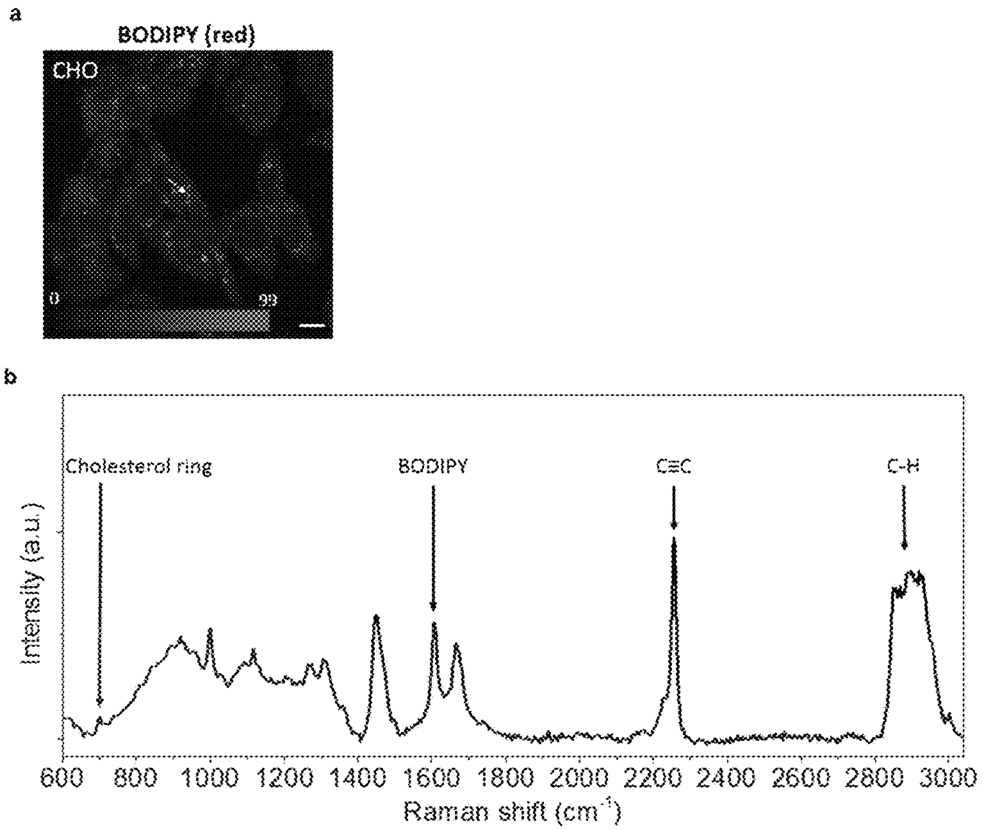

FIG. 11. TPEF imaging and Raman spectral analysis to confirm that PhDY-Chol is stored into LDs. (a) TPEF image of BODIPY-labeled CHO cells. Arrow indicates the point used for Raman spectral analysis. Red intensity bar represents the relative intensity of fluorescence. Scalar bar: 10 μm. (b) Raman spectrum of BODIPY-labeled LDs acquired on the same TPEF microscope. The bands for cholesterol ring, BODIPY, C≡C, and C—H vibrational modes are indicated by black arrows. Spectrum acquisition time: 30 s.

Figure 12:
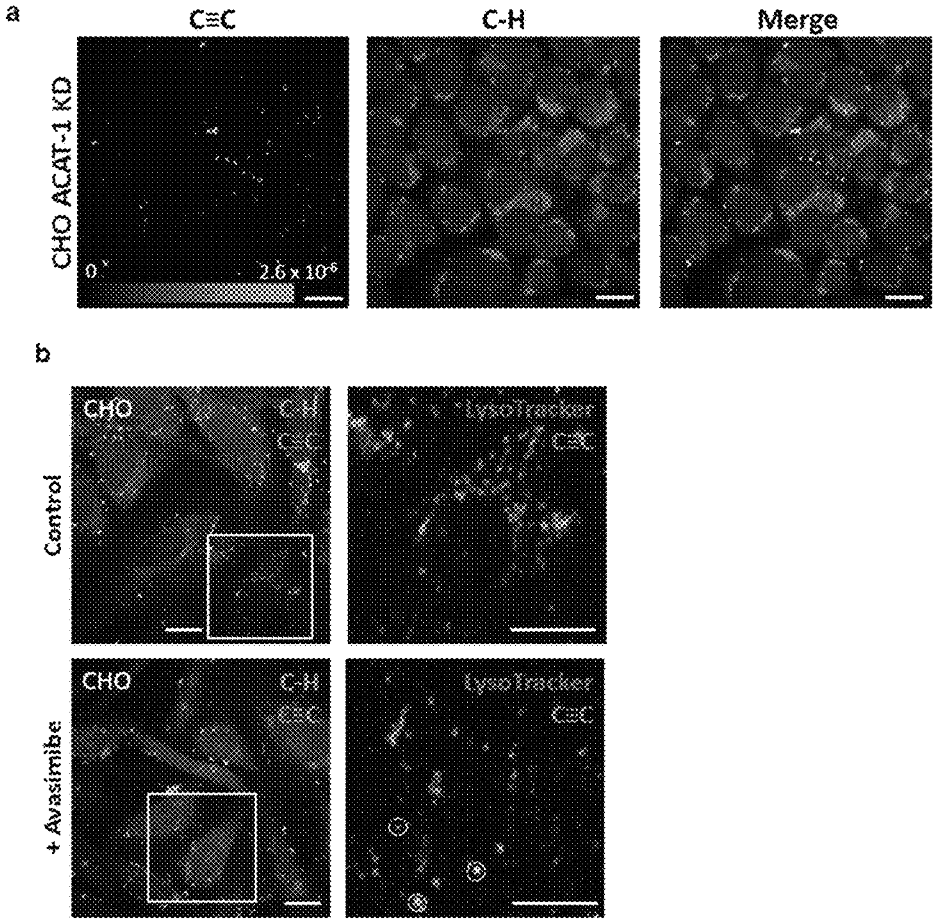

FIG. 12. ACAT-1 inhibition blocks PhDY-CHOL storage into LDs. (a) SRS images of ACAT-1 knocked down CHO cells. No overlap was observed between PhDY-rich particles and LDs. Intensity bar shows the ΔI/I value of the SRS image. Image acquisition speed: 10 μs per pixel for 400×400 pixels. Scalar bar: 10 μm. (b) SRS images of PhDY-Chol and TPEF images of LysoTracker-stained organelles in CHO cells and ACAT-1 inhibited CHO cells by avasimibe treatment. PhDY-Chol was overlapped with LDs but not with LysoTracker-stained organelles in control CHO cells. After avasimibe treatment, PhDY-Chol was not overlapped with LDs but with LysoTracker-stained organelles (circles). Image acquisition speed: 10 μs per pixel for 400×400 pixels. Scalar bar: 10 μm.

Figure 13:
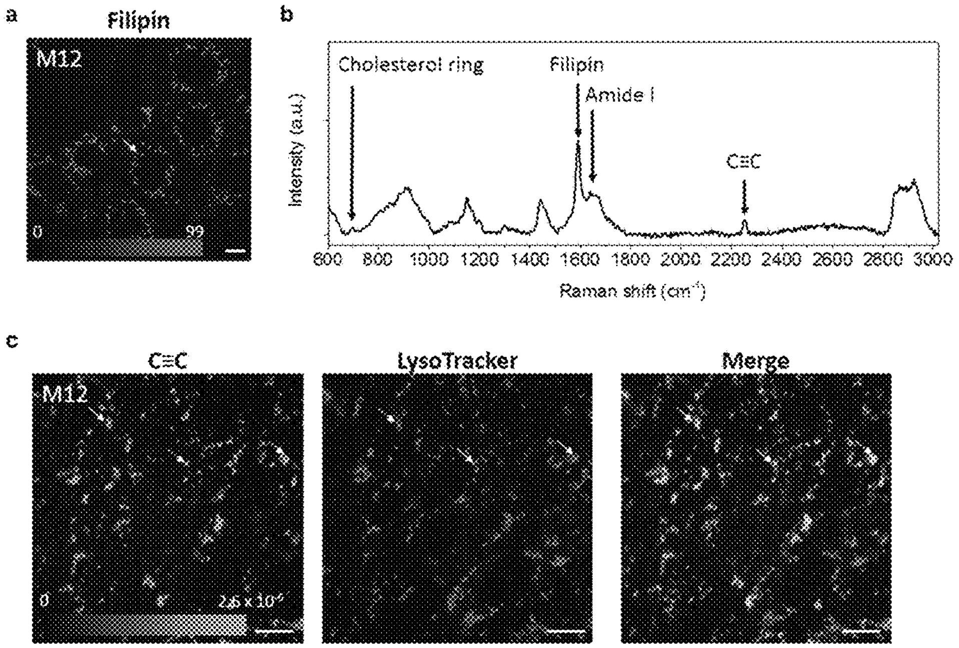

FIG. 13. PhDY-Chol reflects lysosomal cholesterol accumulation in M12 cells. (a) TPEF image of filipin-labeled M12 cells. Arrow indicates the point used for Raman spectral analysis. Red intensity bar represents the relative intensity of fluorescence. Image acquisition speed: 10 μs per pixel for 400×400 pixels. Scalar bar: 10 μm. (b) Raman spectrum of the filipin-labeled organelle acquired on the same TPEF microscope. The bands for cholesterol ring, filipin, protein (amide I), and C≡C vibrational mode are indicated by black arrows. Spectrum acquisition time: 30 s. (c) SRS image of PhDY-Chol and TPEF image of LysoTracker-stained organelles in M12 cells. All PhDY-CHOL was found inside lysosomes. Arrows representatively indicate that PhDY-Chol is accumulated in lysosomes. Intensity bar shows the ΔI/I value of the image. Image acquisition speed: 10 μs per pixel for 400×400 pixels. Scalar bar: 10 μm.

Figure 14:
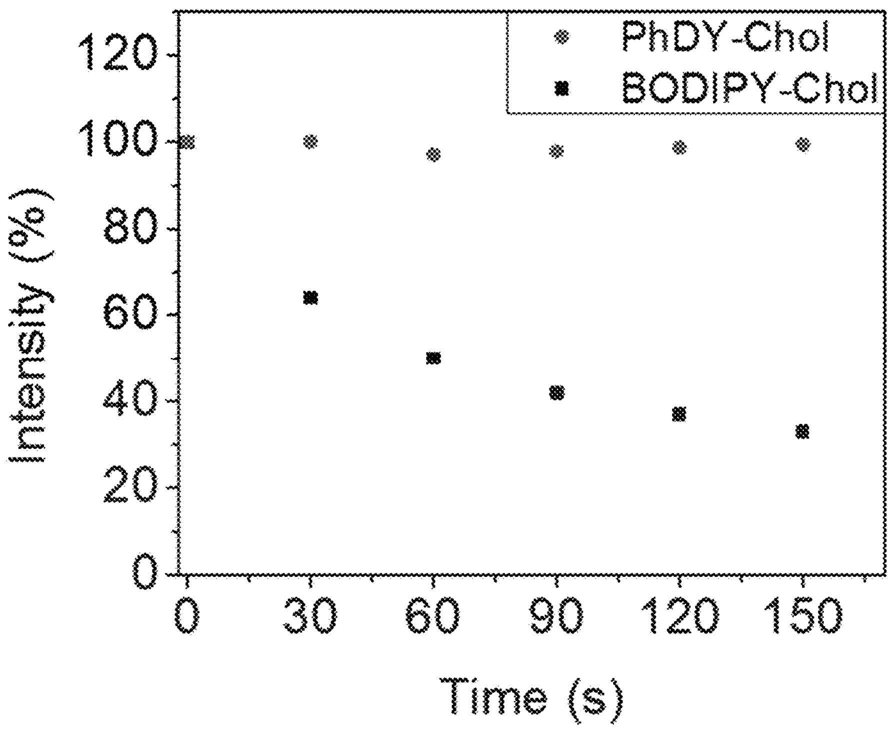

FIG. 14. The photostability of PhDY-Chol and the photobleaching of BODIPY-Chol. The SRS images of 50 mM PhDY-Chol solution and TPEF images of 50 mM BODIPY-Chol solution were acquired continuously for 150 s (one acquisition every 30 s). No significant change of the SRS signal was observed for PhDY-Chol, and a rapid photobleaching was observed for BODIPY-Chol.

Figure 15:
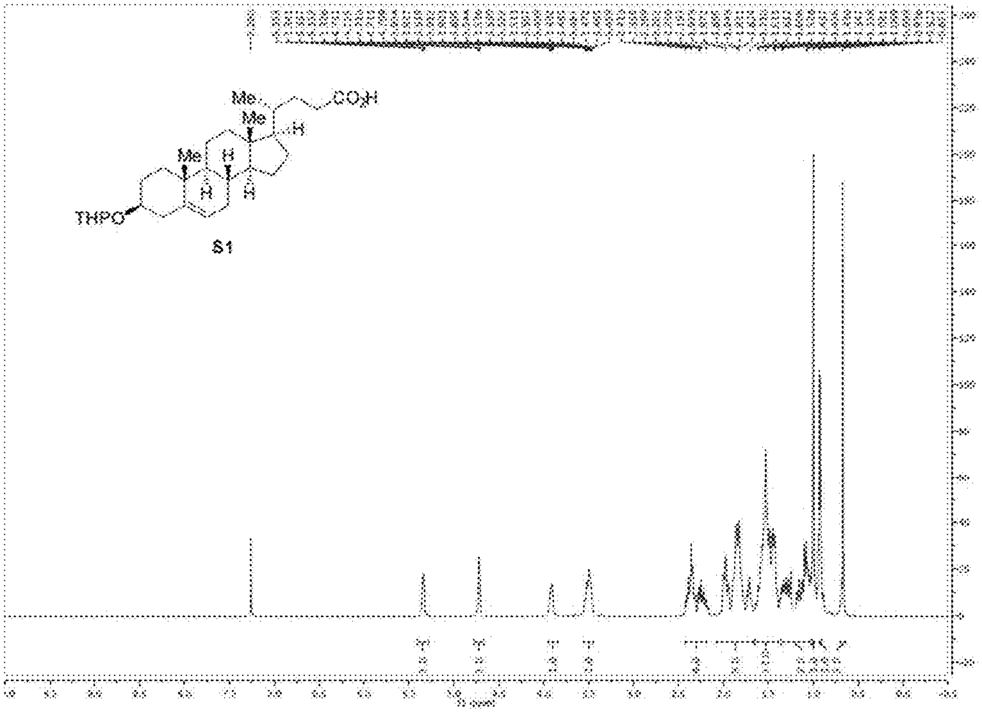

FIG. 15. $^1$H NMR of S1 (500 MHz, $CDCl_3$)

Figure 16:
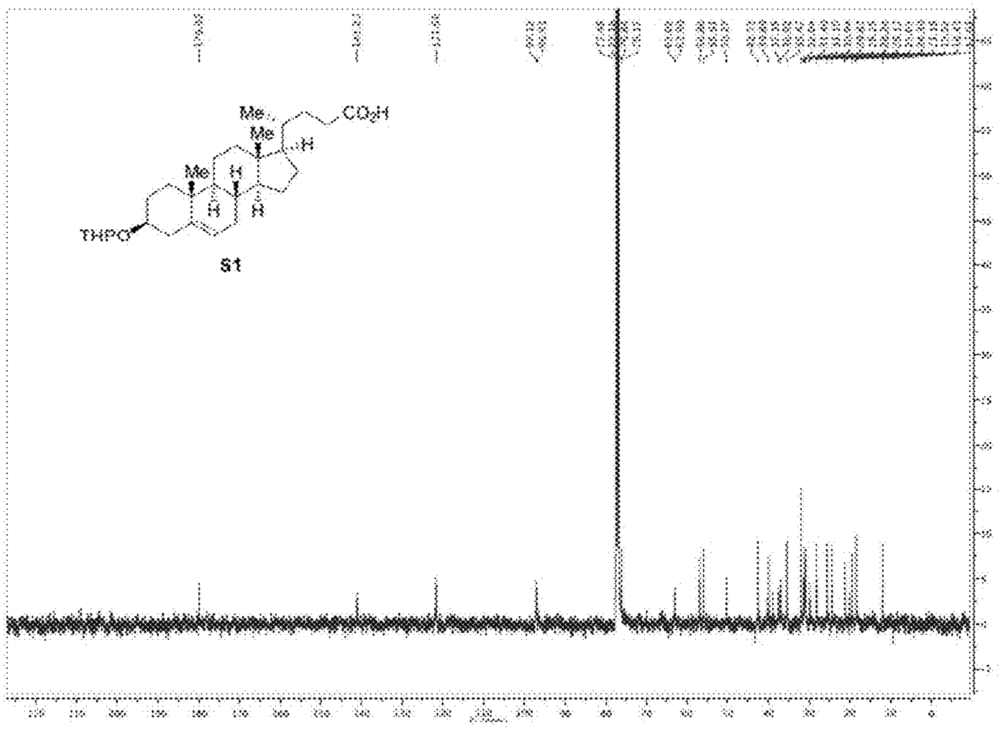

FIG. 16. $^{13}$C NMR of S1 (100 MHz, $CDCl_3$)

Figure 17:
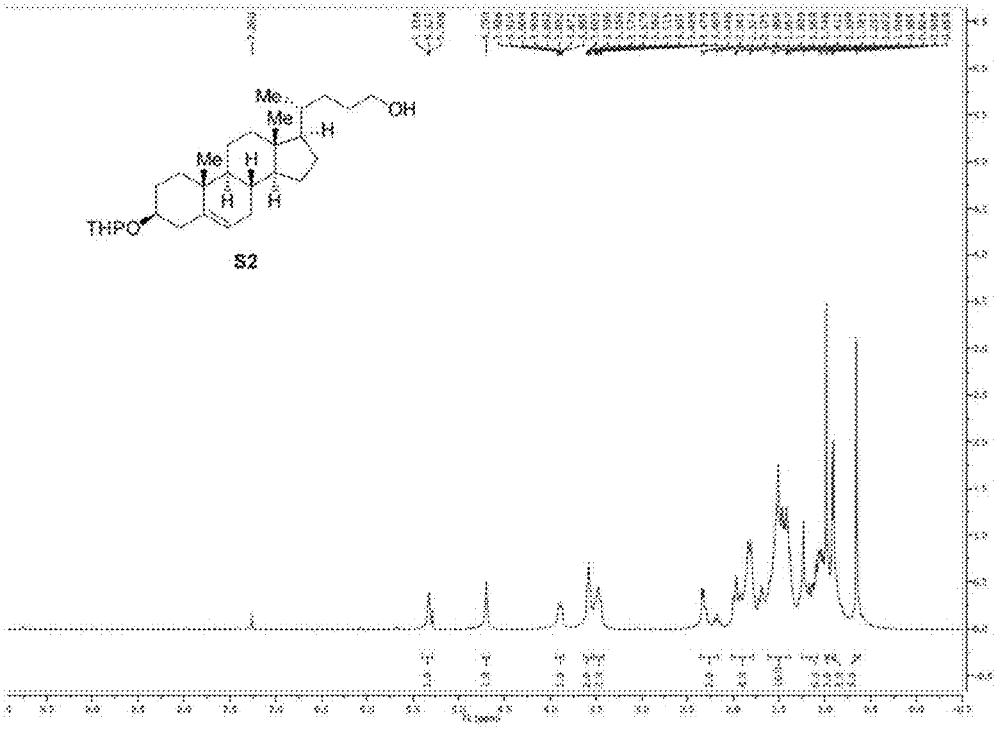

FIG. 17. $^1$H NMR of S2 (400 MHz, $CDCl_3$)

Figure 18:
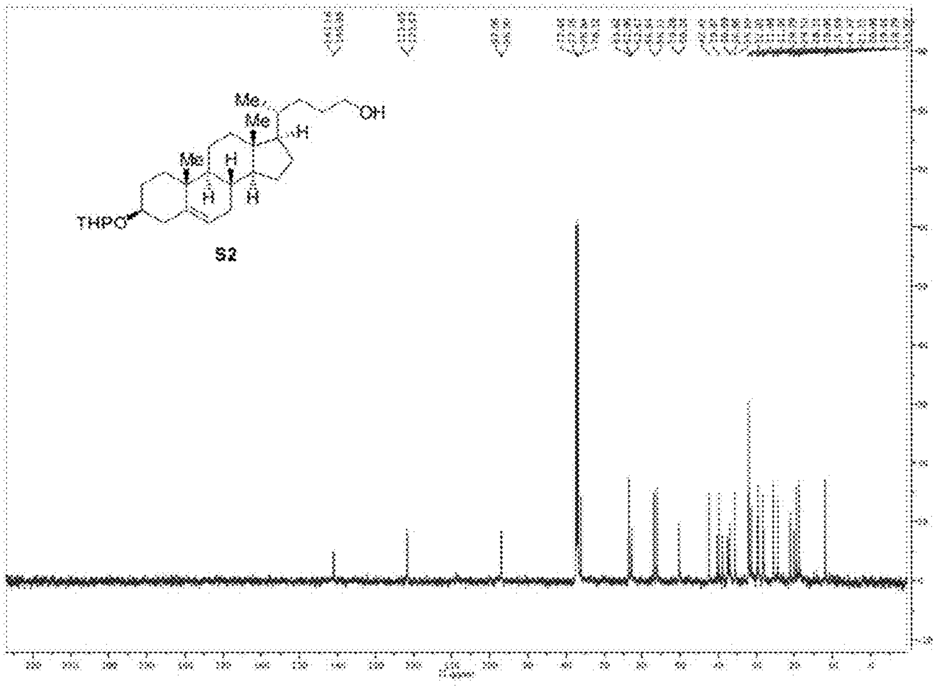

FIG. 18. $^{13}$C NMR of S2 (100 MHz, $CDCl_3$)

Figure 19:
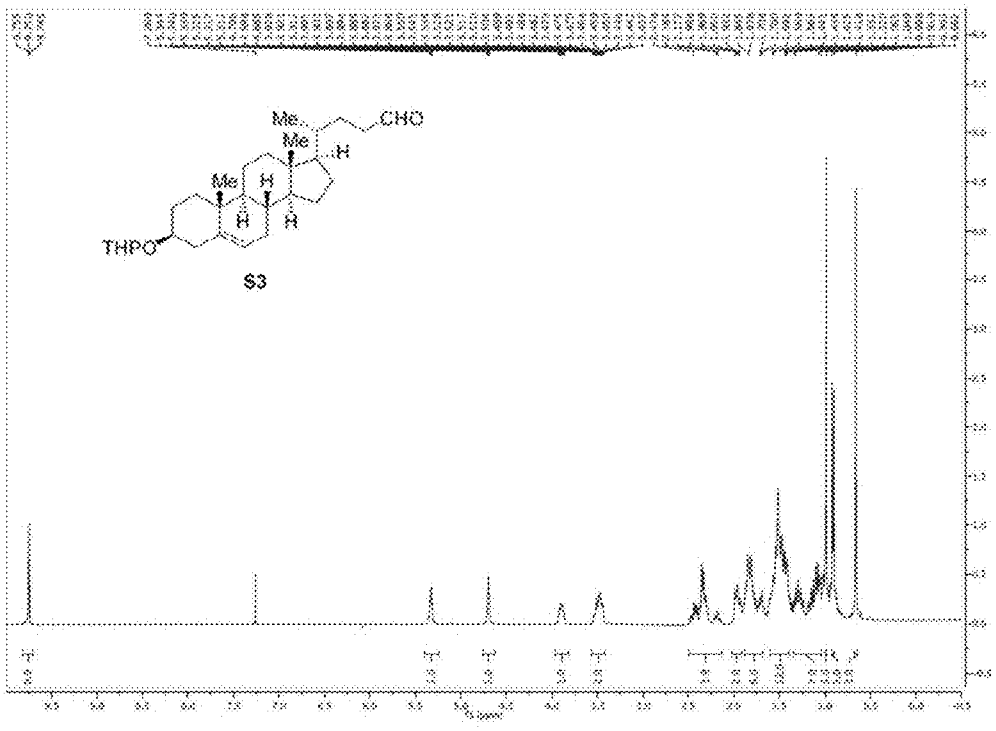

FIG. 19. $^1$H NMR of S3 (400 MHz, $CDCl_3$)

Figure 20:
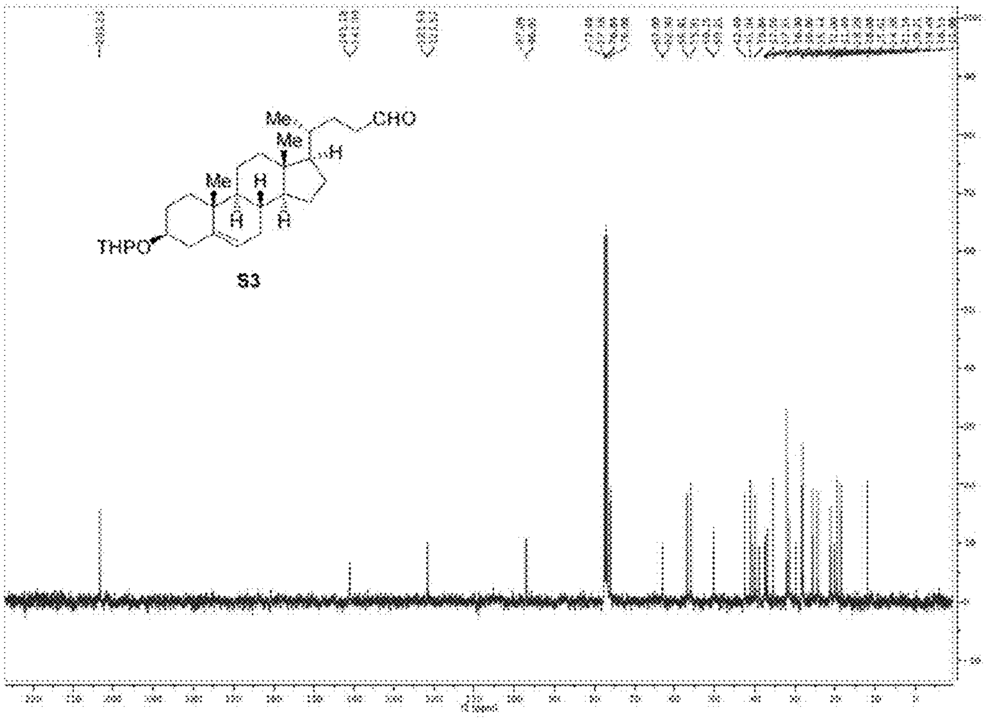

FIG. 20. $^{13}$C NMR of S3 (100 MHz, $CDCl_3$)

Figure 21:
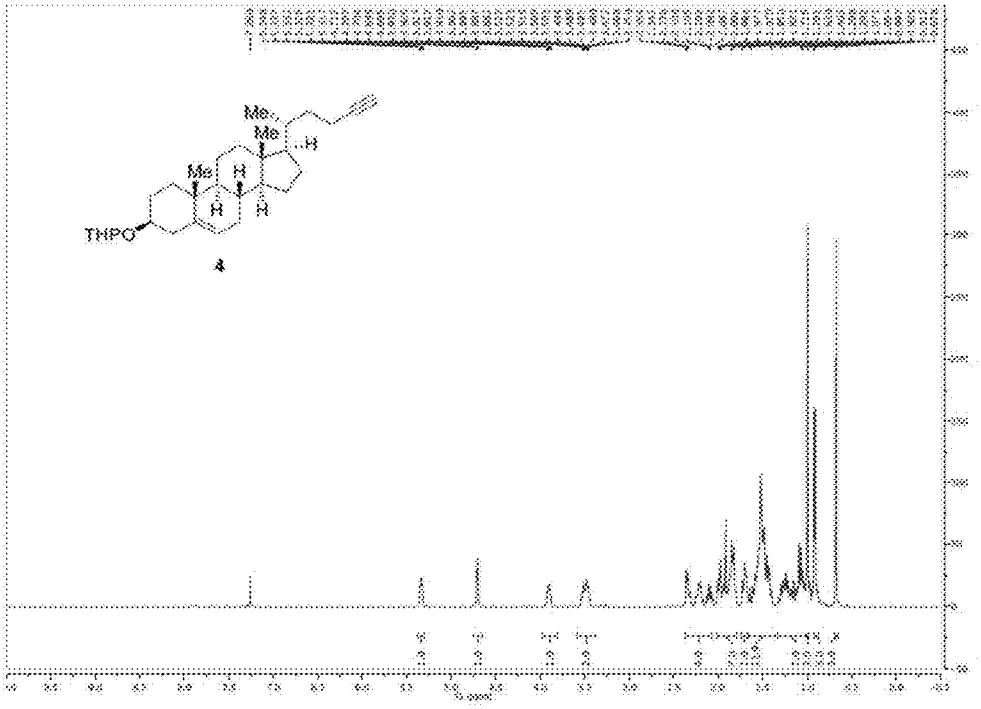

FIG. 21. $^1$H NMR of 4 (500 MHz, $CDCl_3$)

Figure 22:
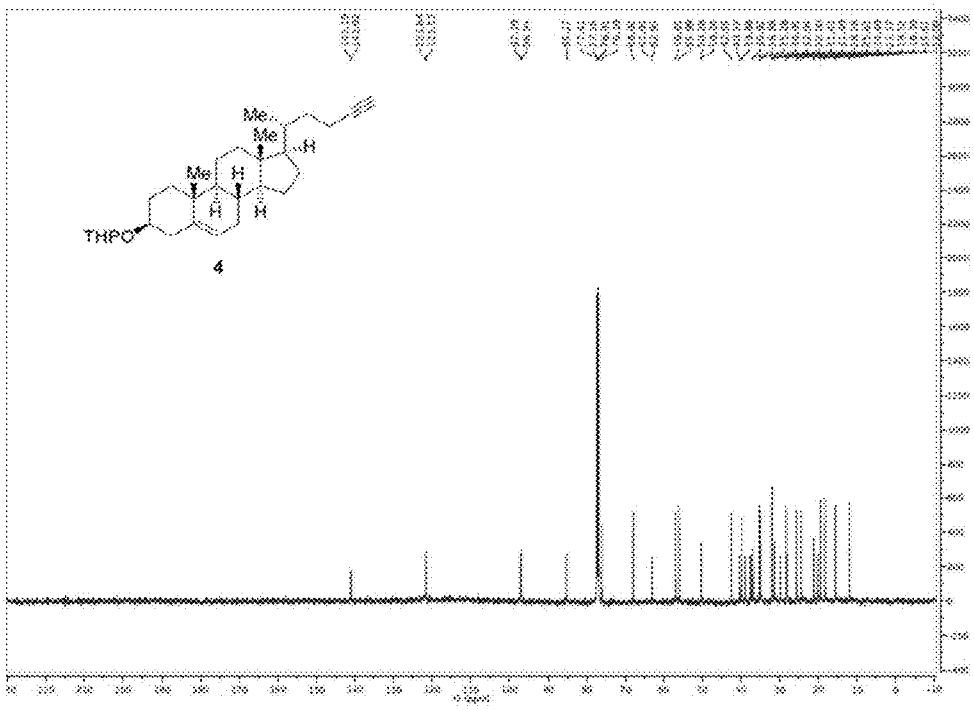

FIG. 22. $^{13}$C NMR of 4 (125 MHz, $CDCl_3$)

Figure 23:
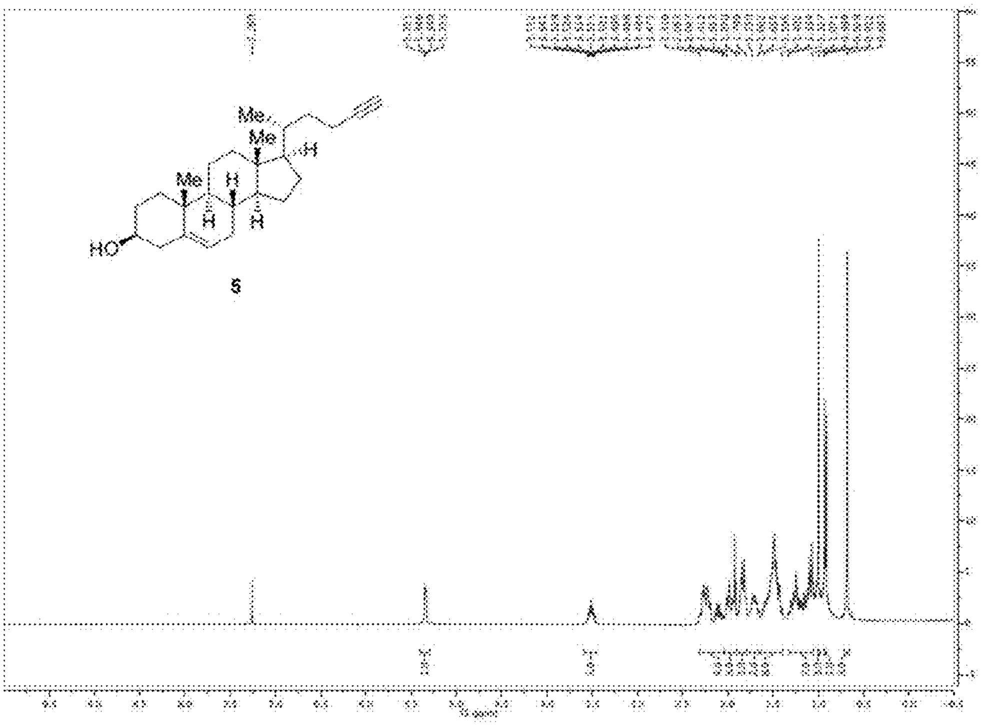

FIG. 23. $^1$H NMR of 5 (400 MHz, $CDCl_3$)

Figure 24:
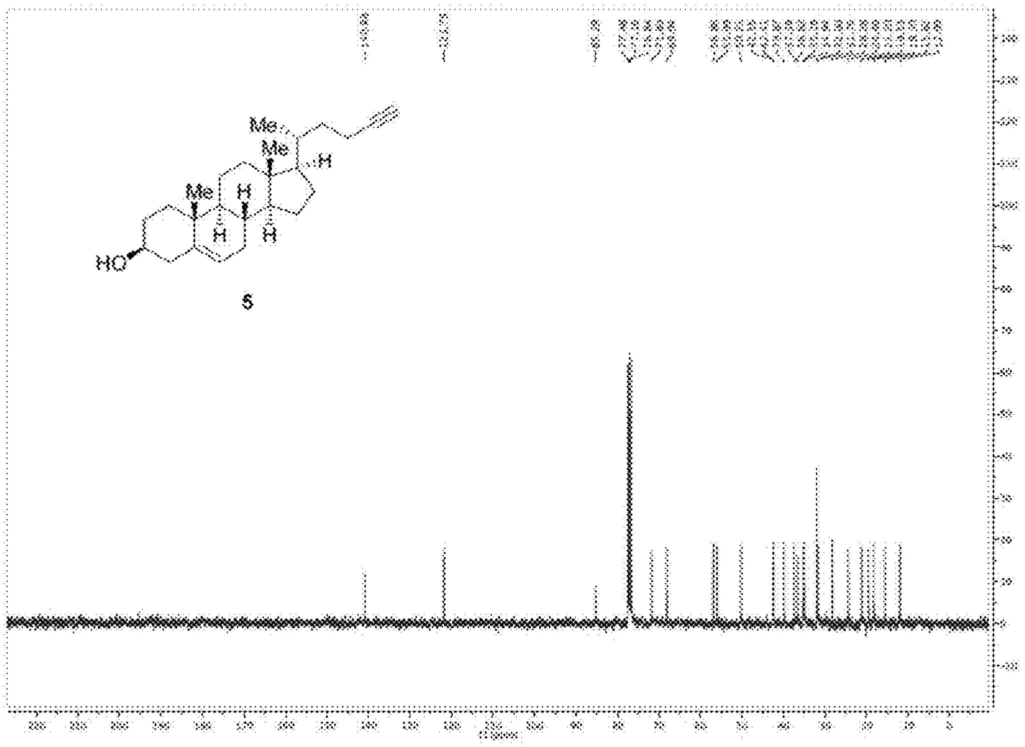

FIG. 24. $^{13}$C NMR of 5 (100 MHz, $CDCl_3$)

Figure 25:
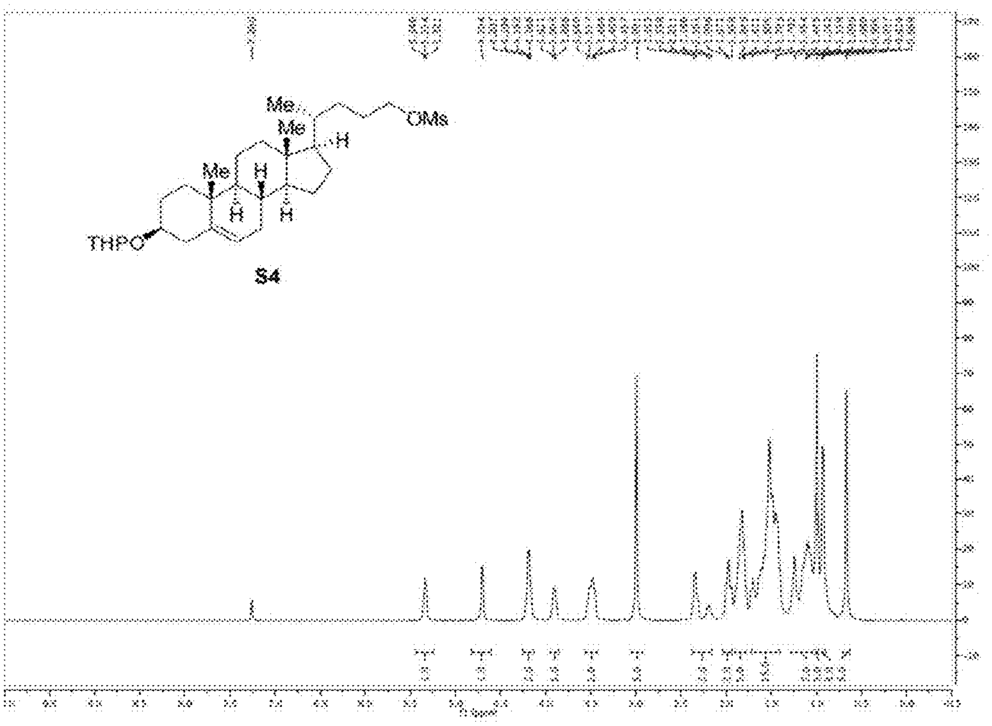

FIG. 25. $^1$H NMR of S4 (400 MHz, $CDCl_3$)

Figure 26:
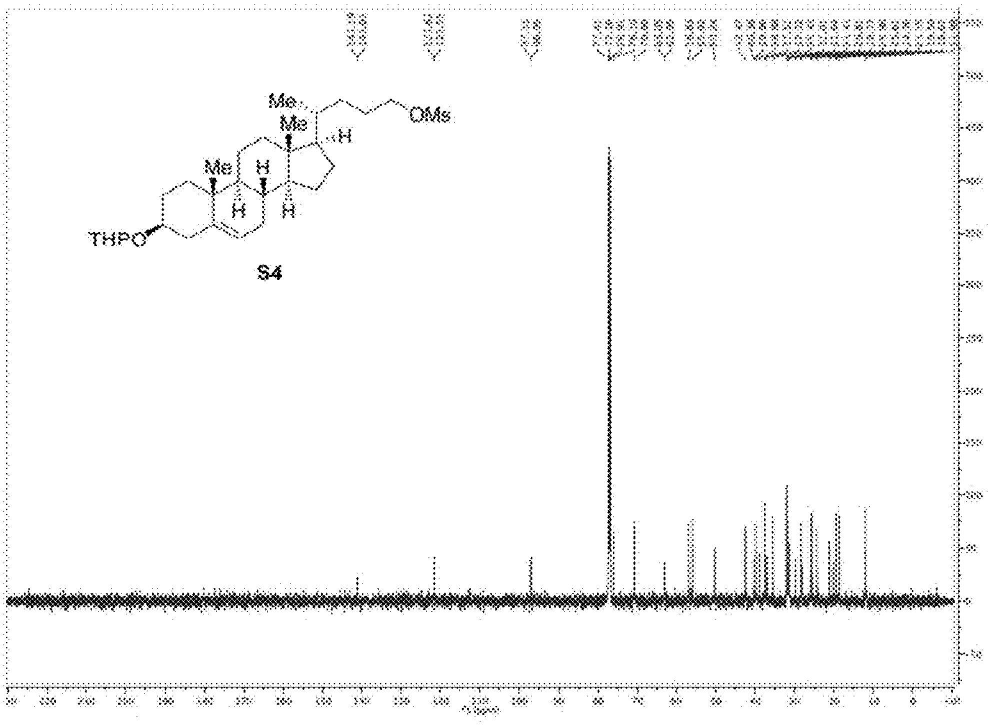

FIG. 26. $^{13}$C NMR of S4 (125 MHz, $CDCl_3$)

Figure 27:
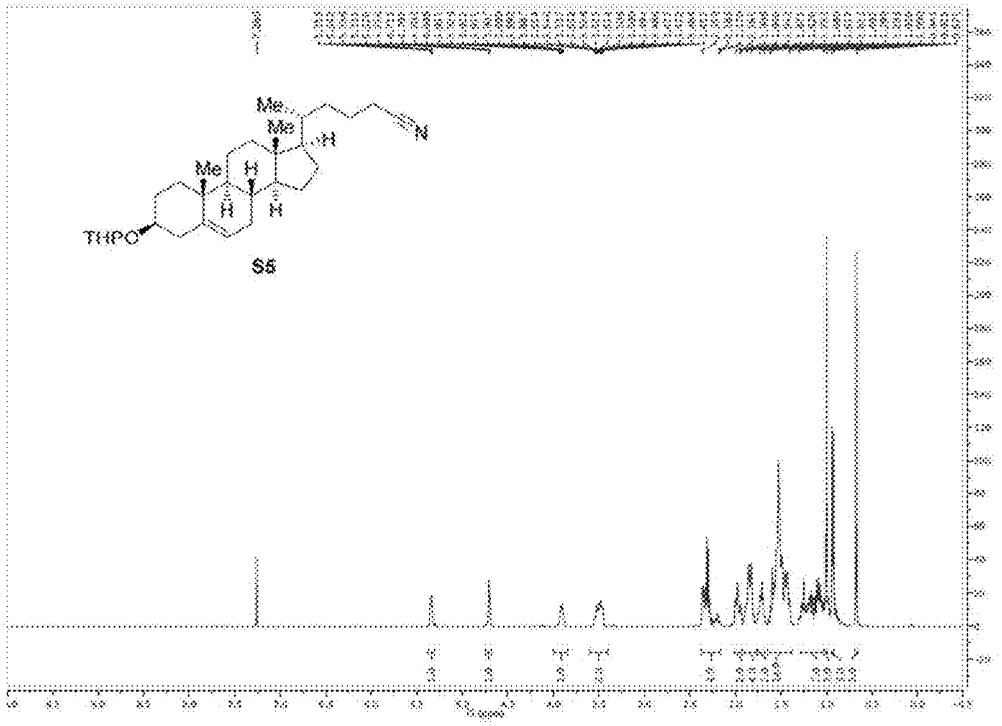

FIG. 27. $^1$H NMR of S5 (500 MHz, $CDCl_3$)

Figure 28:
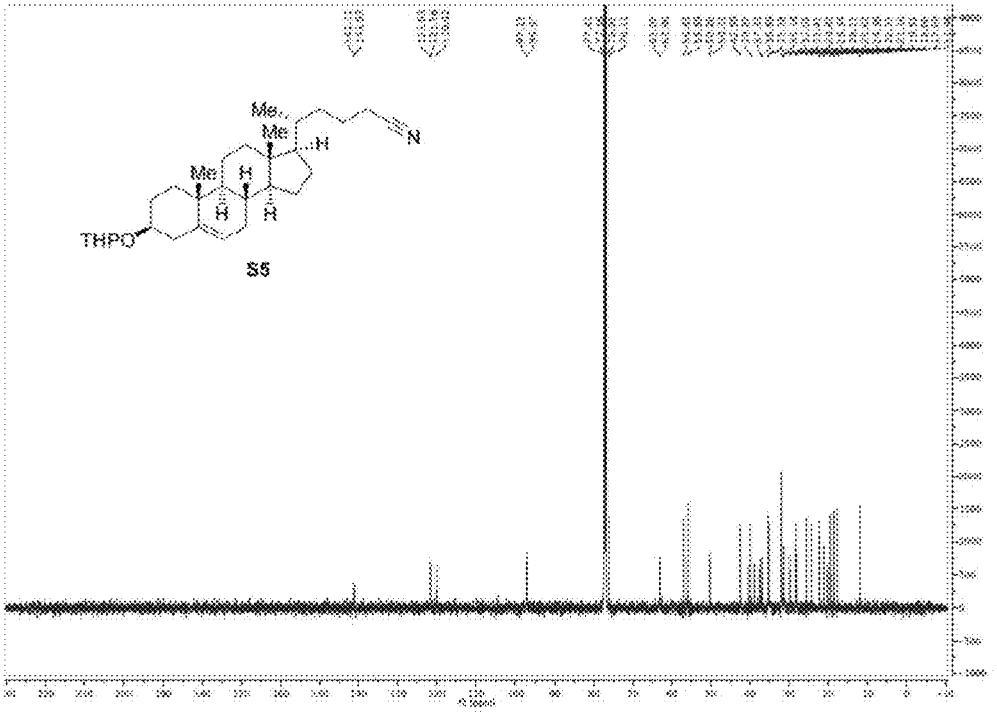

FIG. 28. $^{13}$C NMR of S5 (125 MHz, $CDCl_3$)

Figure 29:
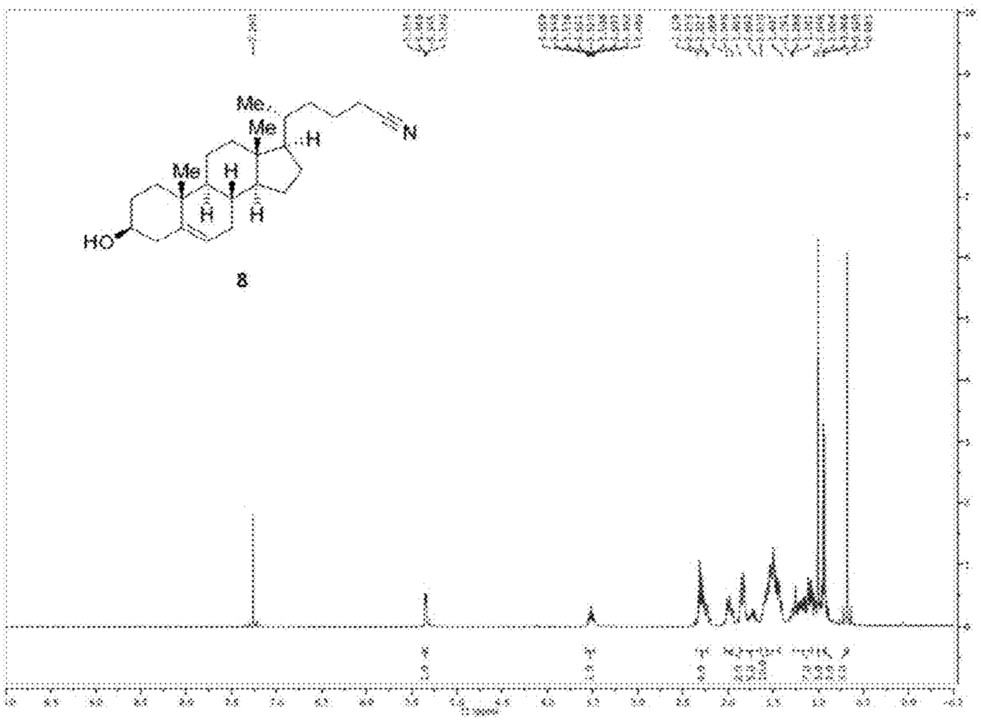

FIG. 29. $^1$H NMR of 8 (400 MHz, $CDCl_3$)

Figure 30:
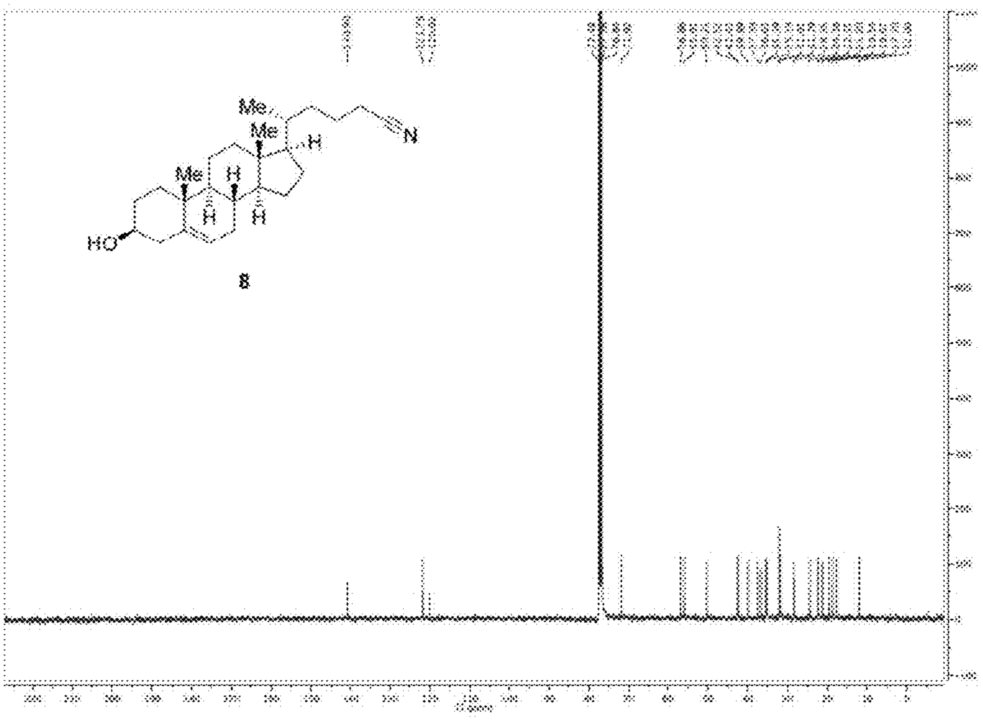

FIG. 30. $^{13}$C NMR of 8 (100 MHz, $CDCl_3$)

Figure 31:
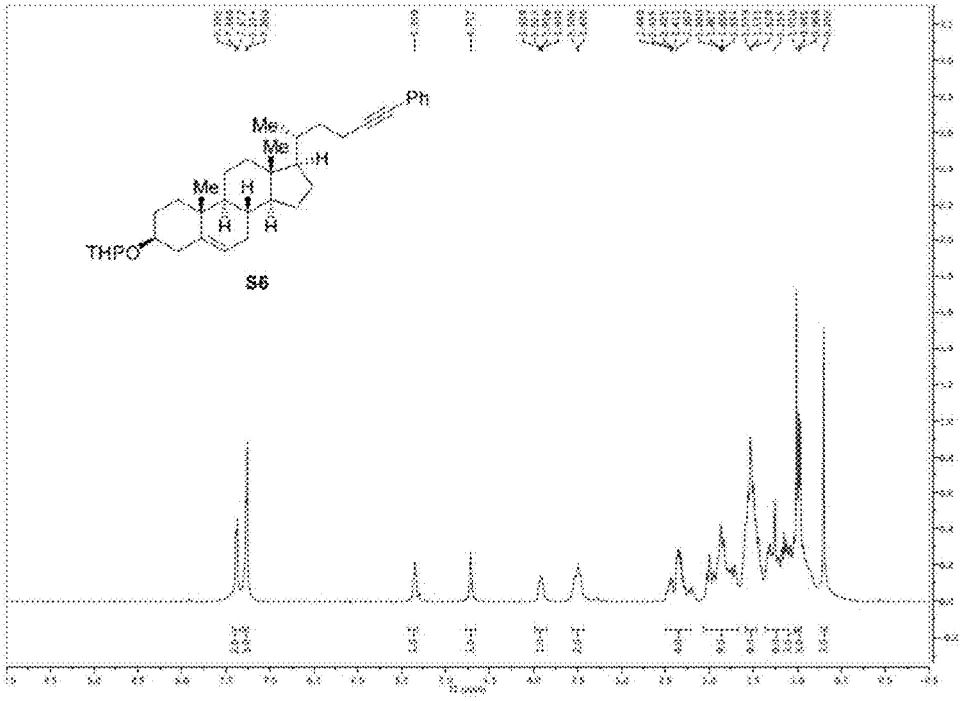

FIG. 31. $^1$H NMR of S6 (400 MHz, $CDCl_3$)

Figure 32:
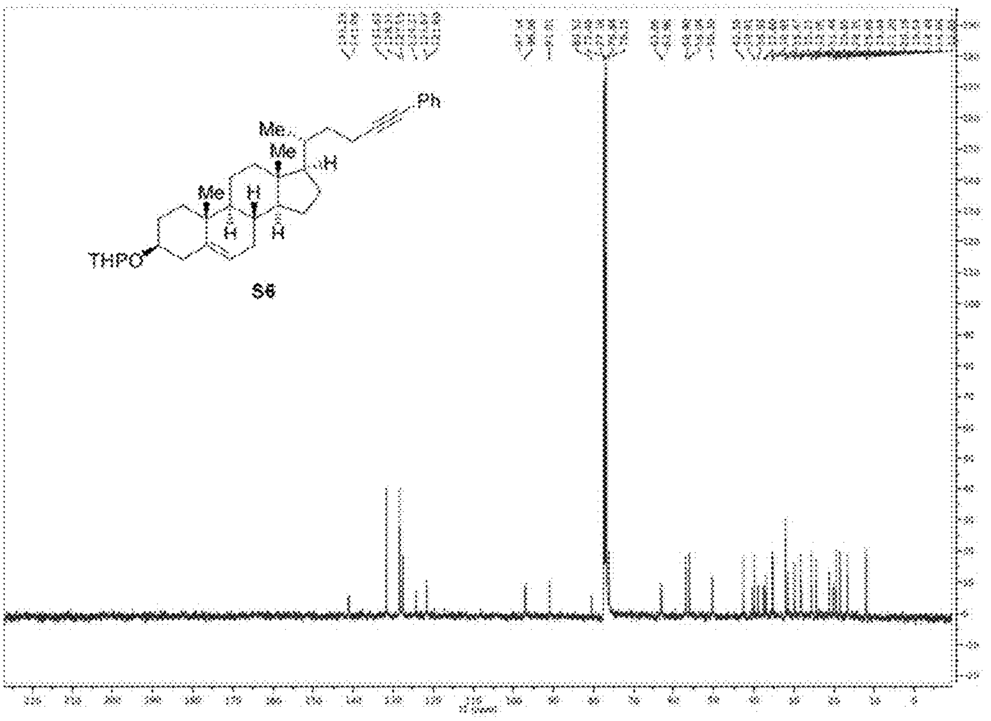

FIG. 32. $^{13}$C NMR of S6 (100 MHz, $CDCl_3$)

Figure 33:
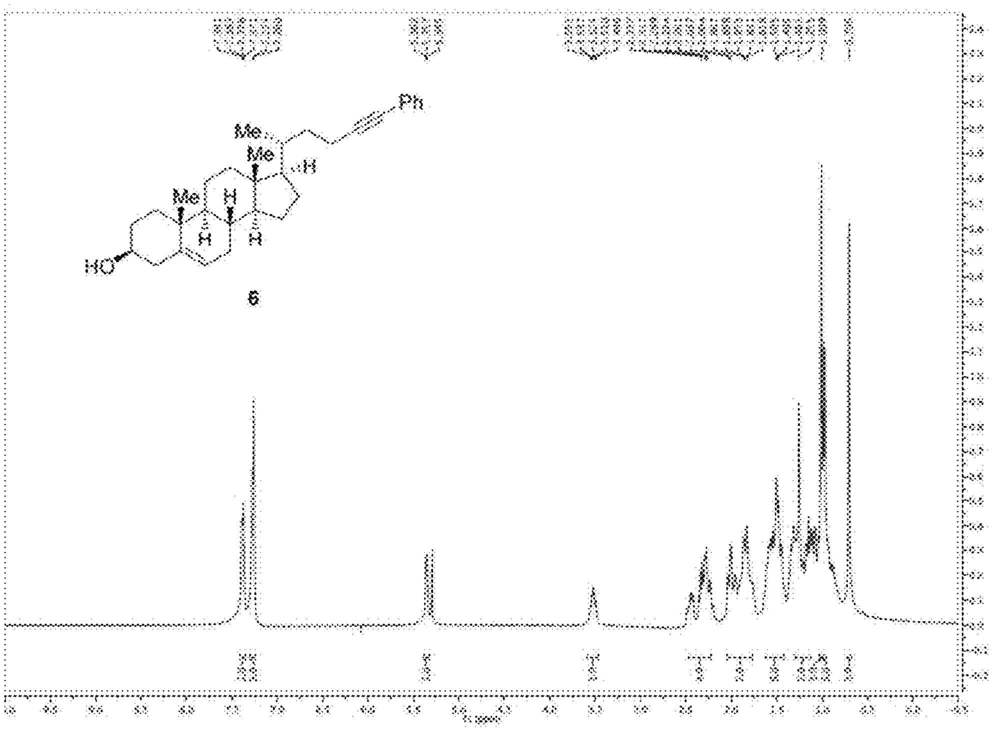

FIG. 33. $^1$H NMR of 6 (400 MHz, $CDCl_3$)

Figure 34:
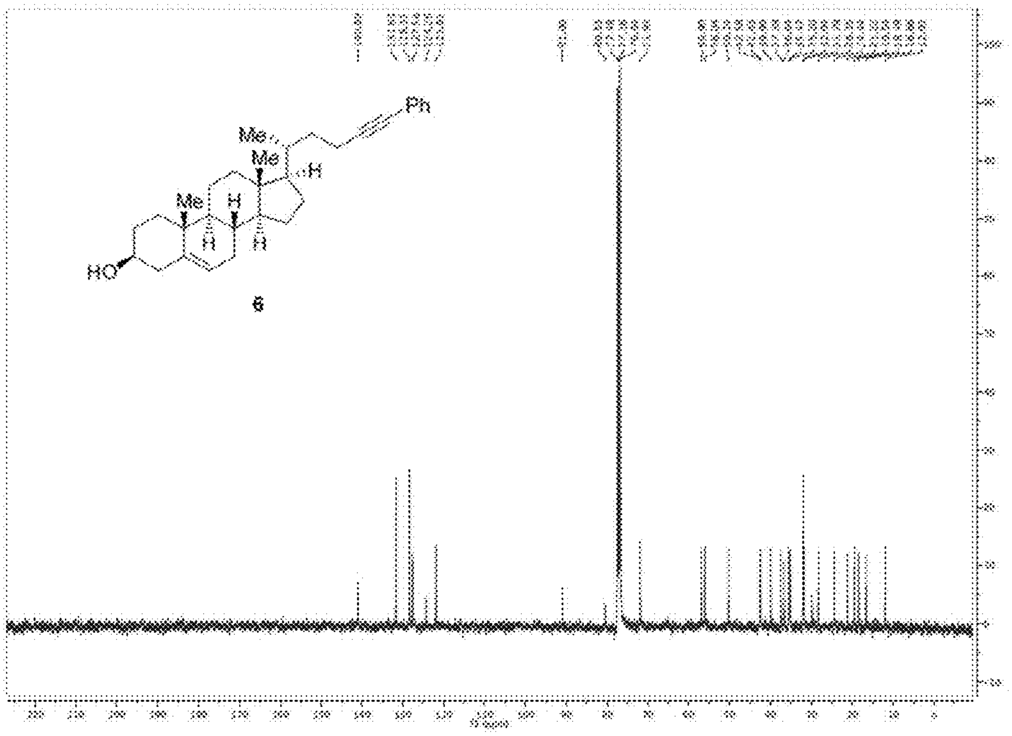

FIG. 34. $^{13}$C NMR of 6 (100 MHz, $CDCl_3$)

Figure 35:
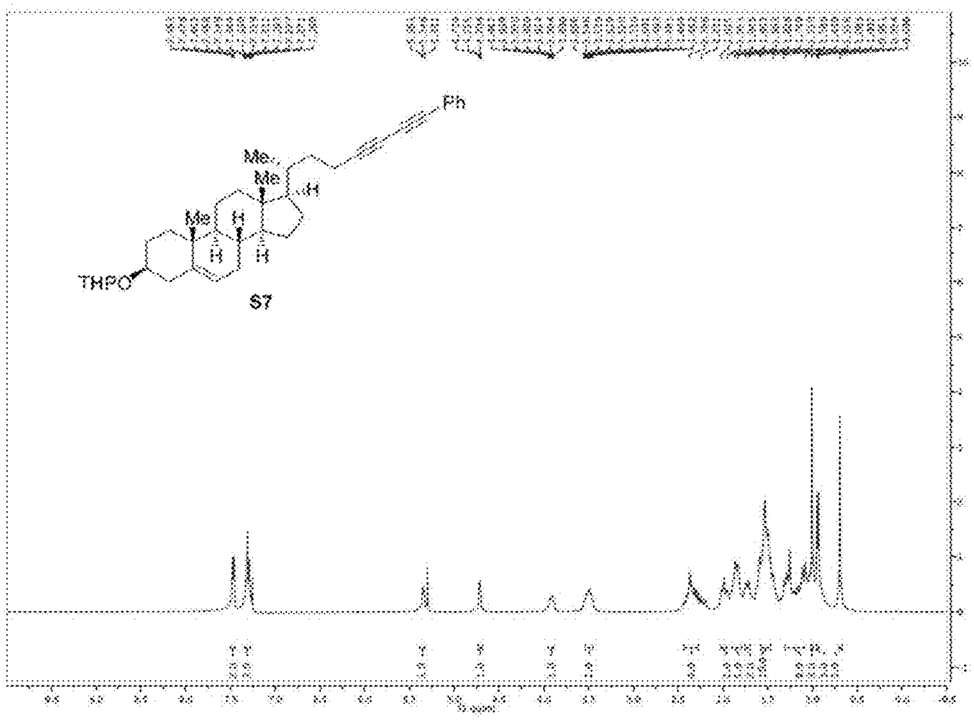

FIG. 35. $^1$H NMR of S7 (400 MHz, $CDCl_3$)

Figure 36:
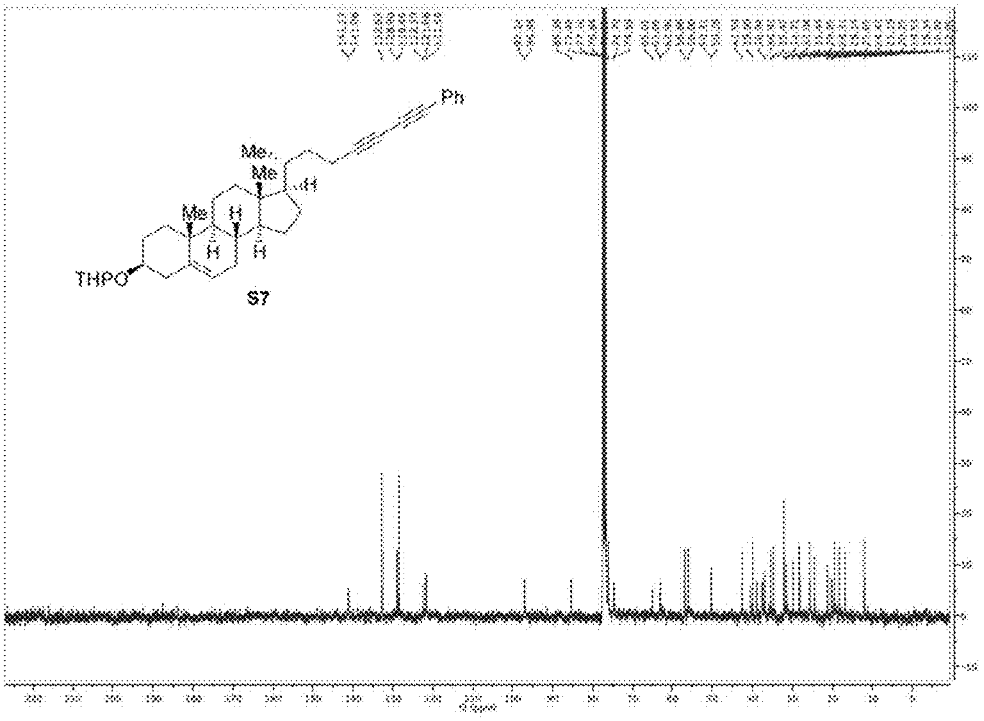

FIG. 36. $^{13}$C NMR of S7 (100 MHz, $CDCl_3$)

Figure 37:
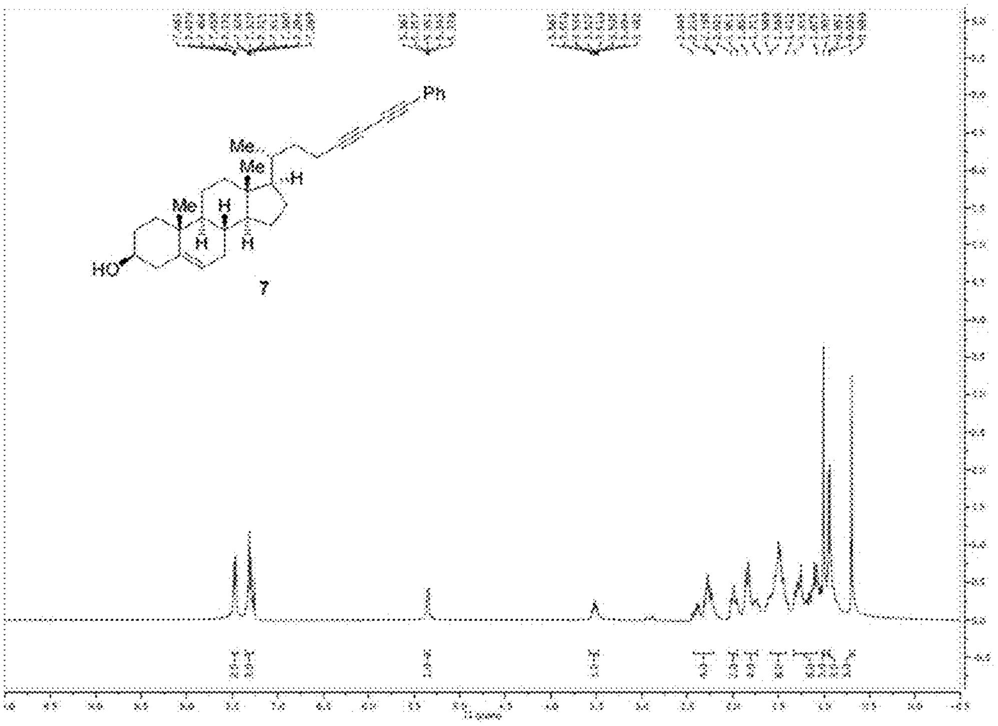

FIG. 37. $^1$H NMR of 7 (400 MHz, $CDCl_3$)

Figure 38:
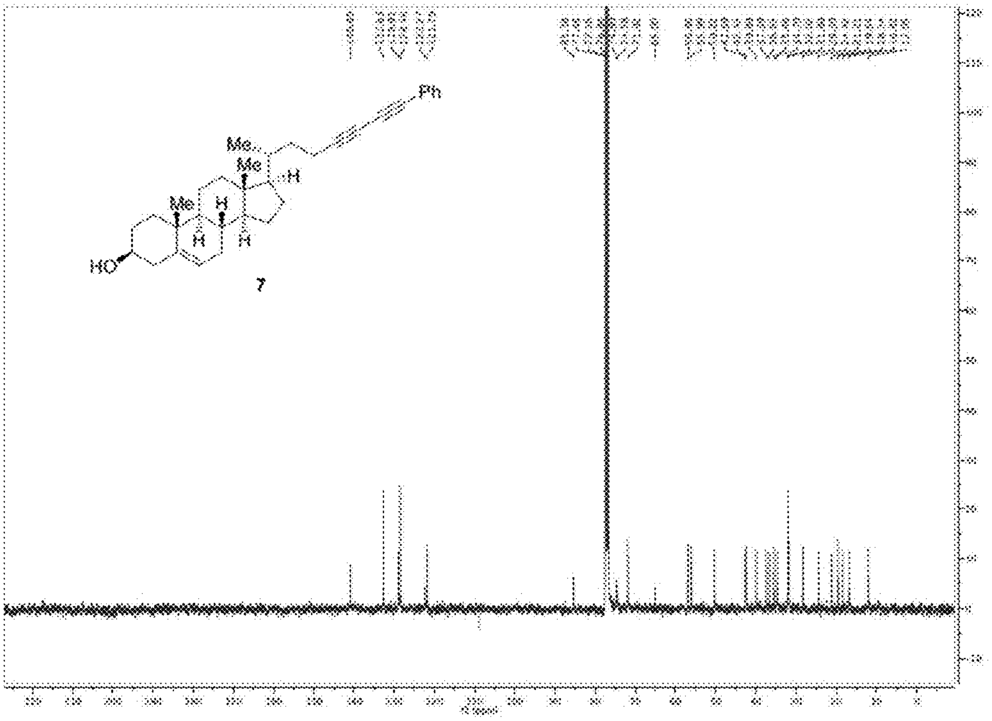

FIG. 38. $^{13}$C NMR of 7 (100 MHz, $CDCl_3$)

Figure 39:
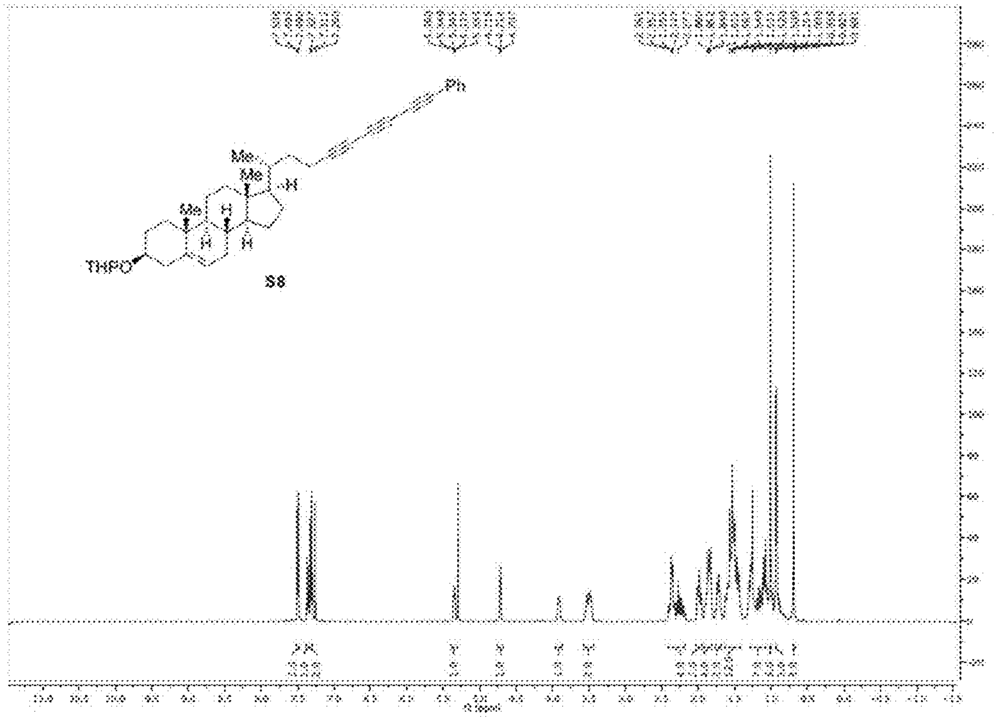

FIG. 39. $^1$H NMR of S8 (500 MHz, $CDCl_3$)

Figure 40:
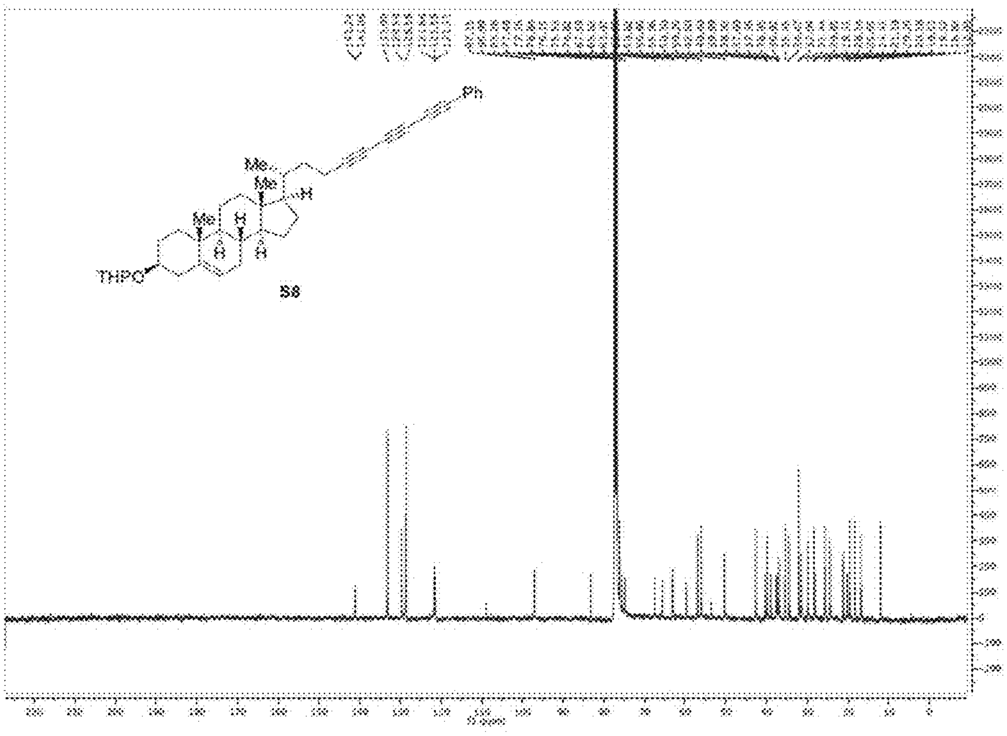

FIG. 40. $^{13}$C NMR of S8 (100 MHz, $CDCl_3$)

Figure 41:
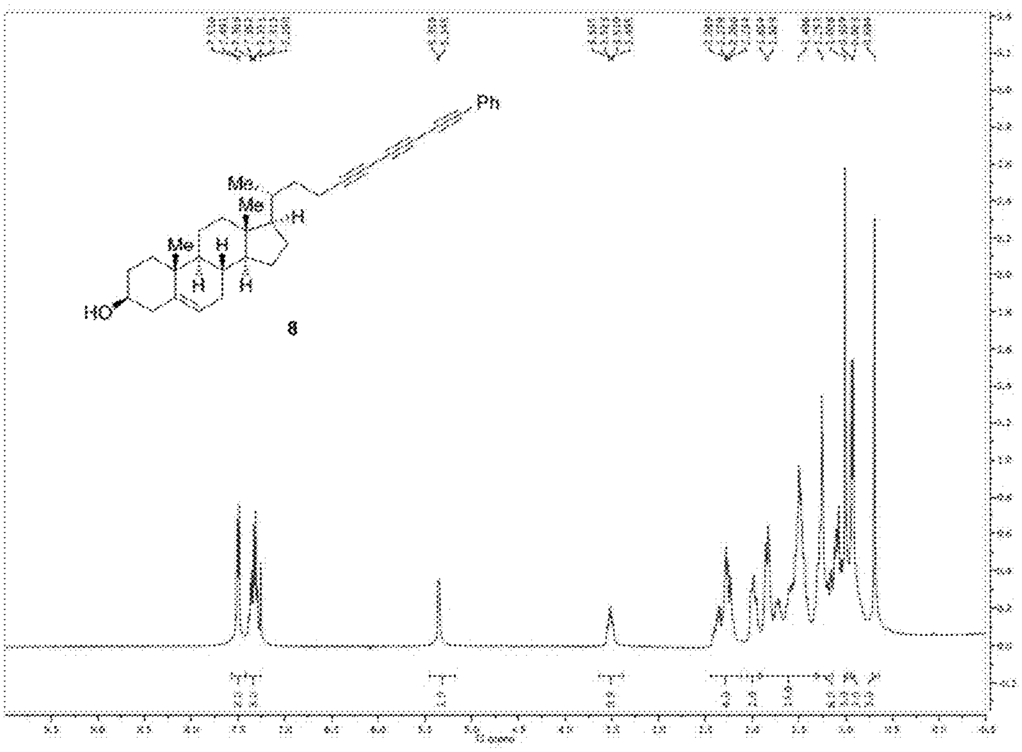

FIG. 41. $^1$H NMR of 8 (400 MHz, $CDCl_3$)

Figure 42:
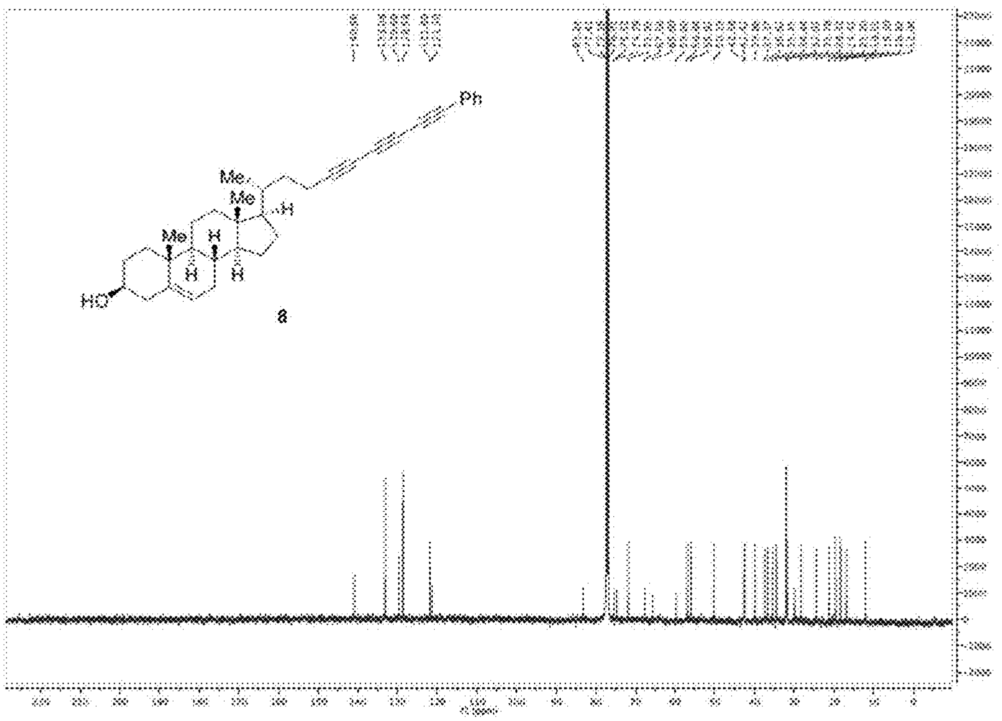

FIG. 42. $^{13}$C NMR of 8 (125 MHz, $CDCl_3$)

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended. The terms "I," "we," "our" and the like throughout the Detailed Description do not refer to any specific individual or group of individuals.

A novel composition and a method that allows bioorthogonal imaging of cholesterol esterification, storage, and trafficking inside living cells and vital organisms. By rational design and chemical synthesis, we prepared a probe molecule, phenyl-diyne cholesterol (PhDY-Chol), which gives a 2,254 $cm^{-1}$ Raman peak that is 122 times stronger than the endogenous C═O stretching band. Compared to alkyne-cholesterol mimic of which the $IC_{50}$ is 16 μM, the phenyl-diyne group is biologically inert and did not cause cytotoxicity after 16 h incubation at 50 μM. In live Chinese hamster ovary (CHO) cells, SRS imaging showed incorporation into plasma membrane, esterification of PhDY-Chol by acyl-CoA: cholesterol acyltransferase 1 (ACAT-1), and storage in lipid droplets (LDs). In a cellular model of NP-C disease, PhDY-Chol is selectively accumulated in lysosomes and is esterified and relocated to LDs after treatment with a cholesterol-mobilization drug. In live *C.elegans*, SRS imaging of PhDY-Chol revealed a previously unnoticed compartment of cholesterol storage, regulated by the cholesterol uptake protein ChUP-1. These studies herald the potential of the method for unveiling intracellular cholesterol trafficking mechanisms and highly efficient screening of drugs that target cholesterol metabolism.

The following describes compositions, methods of synthesis, and methods of use of these compositions in the study of cholesterol. These compositions may be used to study cholesterol localization and movement within live cells. The cholesterol mimics may be used to study and understand different changes in metabolism and organization by tracking the changes in localization and modification of cholesterol. The cholesterol mimics may be used to generate assays for screening lead compounds or treatments to prevent or treat a metabolic irregularity or disease such as cancer. In other aspects the cholesterol mimic may be used to study the lipid droplets with in a given cell, healthy or not healthy, to provide an analysis. The cholesterol mimcs may be used as a target in a drug delivery system, where the drug targets the mimic in a certain unmodified or modified state, specifically. The cholesterol mimics may be used to provide a diagnosis or monitor the health of a patient's cells before or during treatment for a disease. The cholesterol mimics may be used in vitro or in vivo (i.e. cells and tissues, whole organs, or live animals or humans), and may be analyzed in live or fixed cells.

The cholesterol mimics may be provided for use in a powder or crystal form, or suspended in liquid. The cholesterol mimics may be supplied by several delivery means including but not limited to orally, intravenously, injection, inhalation, catheter, dermal absorption, or ingestion.

Figure 1:
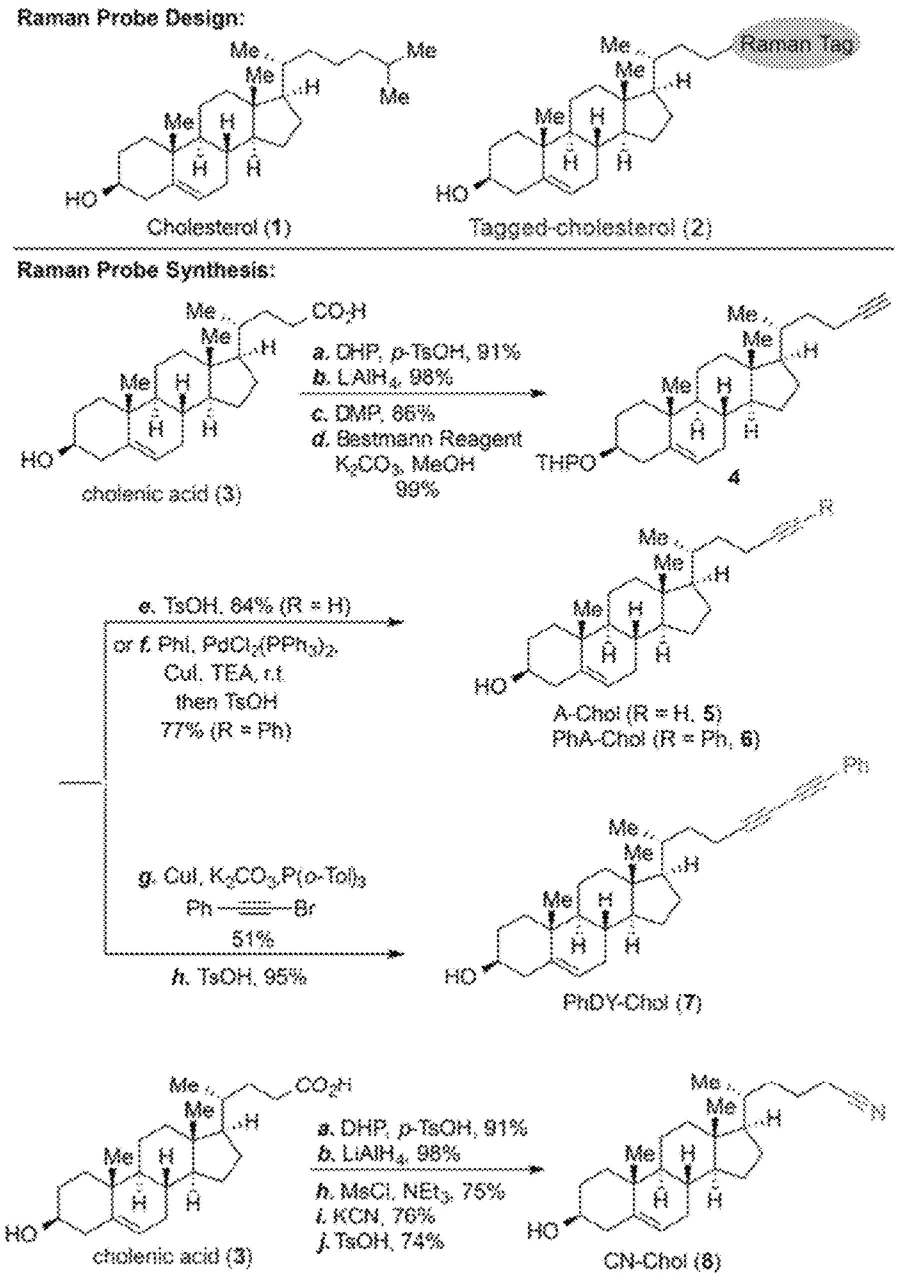
FIG. 1. Design and synthesis of tagged cholesterol probes. Reagents and conditions: a) DHP (5.0 equiv), p-TsOH (0.2 equiv), THF, RT, 91%; b) $LiAlH_4$ (3.0 equiv), THF, 0° C. RT, 98%; c) DMP (3.0 equiv), $NaHCO_3$ (3.0 equiv), $CH_2Cl_2$, 0° C., 86%; d) dimethyl (1-diazo-2-oxopropyl)phosphonate (Bestmann reagent, 2.4 equiv), $K_2CO_3$ (4.0 equiv), THF/MeOH, RT, 99%; e) p-TsOH (1.0 equiv), THF/MeOH, RT, 84%; f) Iodobenzene (1.02 equiv), $PdCl_2(PPh_3)_2$ (0.05 equiv), CuI (0.05 equiv), TEA, RT; then TsOH (1.0 equiv), THF/MeOH, RT, 77%; g) CuI (0.1 equiv), $K_2CO_3$ (2.0 equiv), P(o-Tol)$_3$ (0.2 equiv), phenyl bromoacetylene (1.3 equiv), EtOH, 100° C., 51%; h) TsOH (1.0 equiv), THF/MeOH, RT, 95%; i) MsCl (3.0 equiv), TEA (3.0 equiv), $CH_2Cl_2$, 0° C. RT, 75%; j) KCN (2.0 equiv), DMSO, 90° C., 76%; k) TsOH (1.0 equiv), THF/MeOH, RT, 74%. DHP=3,4-Dihydro-2H-pyran, DMP=Dess-Martin Periodinane, p-TsOH=p-Toluenesulfonic acid, TEA=triethylamine, P(o-Tol)$_3$=tri(o-tolyl)phosphine, MsCl=methanesulfonyl chloride. CN: cyano; A: alkyne; PhA: phenyl-alkyne; PhDY: phenyl-diyne; Chol: cholesterol.

In general, a cholesterol mimic is generated by replacing the aliphatic chain of in cholesterol with a group that changes the Raman spectra produced during Raman spectroscopy. Ideally, a peak is generated from this molecule that is differentiated from other signals produced by a cell or tissue. One aspect, is to replace the aliphatic chain of cholesterol with a group that will generate a peak between 1,800 and 2,800 $cm^{-1}$ in a Raman scatter. One way to produce a signal in this region is to add a C≡C moiety to cholesterol, as shown in FIG. 1. In certain aspects a C≡C bond may be added one, two, three, four, five, or six times to increase signal. In certain aspects there are three C≡C bonds included in the cholesterol mimic.

In certain aspects the PhDY-Chol mimic probe was generated by replacing the aliphatic chain in cholesterol with phenyl-diyne. The following chemical structures illustrate some of the mimics:

-continued (I)

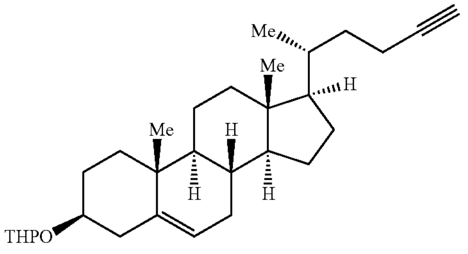

4

(II)

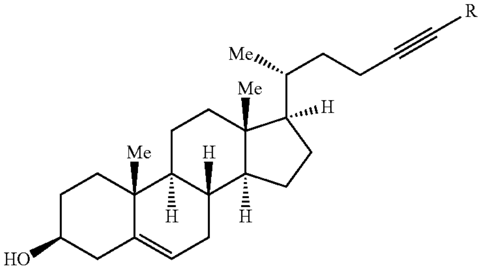

A-Chol (R = H, 5)
PhA-Chol (R = Ph, 6)

(III)

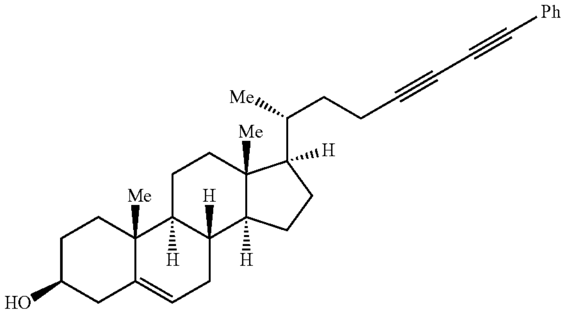

PhDY-Chol (7)

(IV)

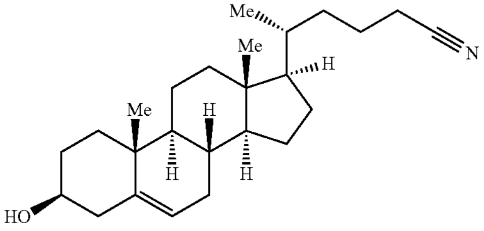

CN-Chol (8)

(V)

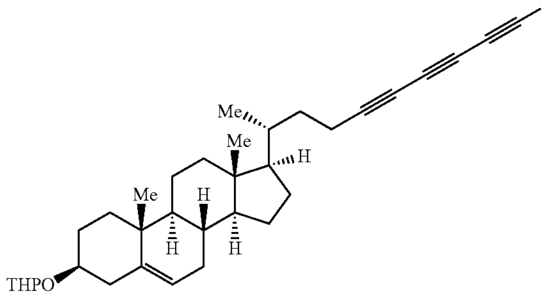

S8

(VI)

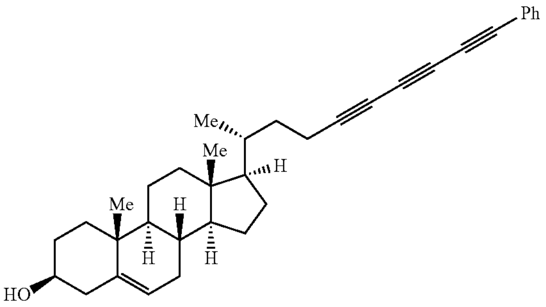

9

In certain aspects of the technology, the mimic is viewed by Raman spectroscopy. Those of skill in the art will understand the set up and laser sources to use given the chemical nature of the cholesterol mimic. For illustrative purposes only, one may look to the contents of the Figures, Brief Descriptions of the Figures and Detailed Description of this Application, to understand one example of a setup for performing Raman spectroscopy using the disclosed cholesterol mimics.

Cholesterol mimics were synthesized and a few specific embodiments will now be described. Referring now to FIG. 1, alkyne cholesterol (A-Chol, 5), phenyl-alkyne cholesterol (PhA-Chol, 6), phenyl-diyne cholesterol (PhDY-Chol, 7), and cyano cholesterol (CN-Chol, 8). Initially, synthesis commenced with cholenic acid 3. Using a sequence of THP-protection, $LiA1H_4$ reduction, Dess-Martin oxidation and Seyferth-Gilbert-Bestmann homologation, cholenic acid 3 was converted to compound 4 intermediate with a terminal alkyne group. Removal of the THP-protecting group gave probe A-Chol 5. PhA-Chol 6 and PhDY-Chol 7 were prepared from compound 4 intermediate via a palladium-catalyzed Sonogashira reaction and a copper-catalyzed Cadiot-Chodkiewicz reaction, respectively, followed by acidic removal of THP group. Additionally, CN-Chol 8 was prepared from cholenic acid 3 via standard transformations.

The following are specific examples and embodiments, and not meant to be limiting in any way.

Design and Synthesis of Composition

Referring to FIG. 1, in order to design a probe molecule that not only maintains physiological functions of cholesterol, but also has a large Raman scattering cross section, we chose to replace the aliphatic side chain of cholesterol with a cyano or alkynyl groups. These groups have small size, which could minimize structural perturbation of the molecule of interest, in this case, cholesterol. These groups produce strong Raman scattering peaks in a cellular silent region (1,800-2,800 $cm^{-1}$), and can be used for Raman imaging in a low-concentration condition. It has been reported that as the chain length increases, the hyperpolarizability increases in polyynes. Also, aromatic ring capped alkyne was shown to give stronger Raman signals than terminal alkyne. To design cholesterol mimic with very strong Raman intensity, we calculated the Raman cross section of potential tags—alkyne, phenyl-alkyne, diyne, phenyl-diyne using the Q-Chem and GAMES S electronic structure packages to provide insight of the relation between molecular structure and Raman intensity. The results showed that the localized polarizabilities on each C≡C moiety increase with the number of conjugated triple bonds, as well as with addition of a phenyl ring.

The total polarizability of the molecule increases as a result of the additive effect as well as non-linear boost in the polarizability of conjugated bonds. The phenyl ring serves as both a donor and an acceptor of π-electrons from the neighboring triple bonds, further escalating polarizabilities of neighboring conjugated bonds. Taking into account that the Raman intensity is proportional to squares of polarizability derivatives, the additional three-fold enhancement of the total polarizability due to conjugation results in a ~10-fold boost in Raman intensity. Together, the Raman intensity increases further by adding a phenyl group to the terminal alkyne, and increases even further by conjugating a phenyl group and another alkyne.

Raman Spectral Analysis of Stimulate Raman Scattering of Cholesterol Mimics

Figure 2:
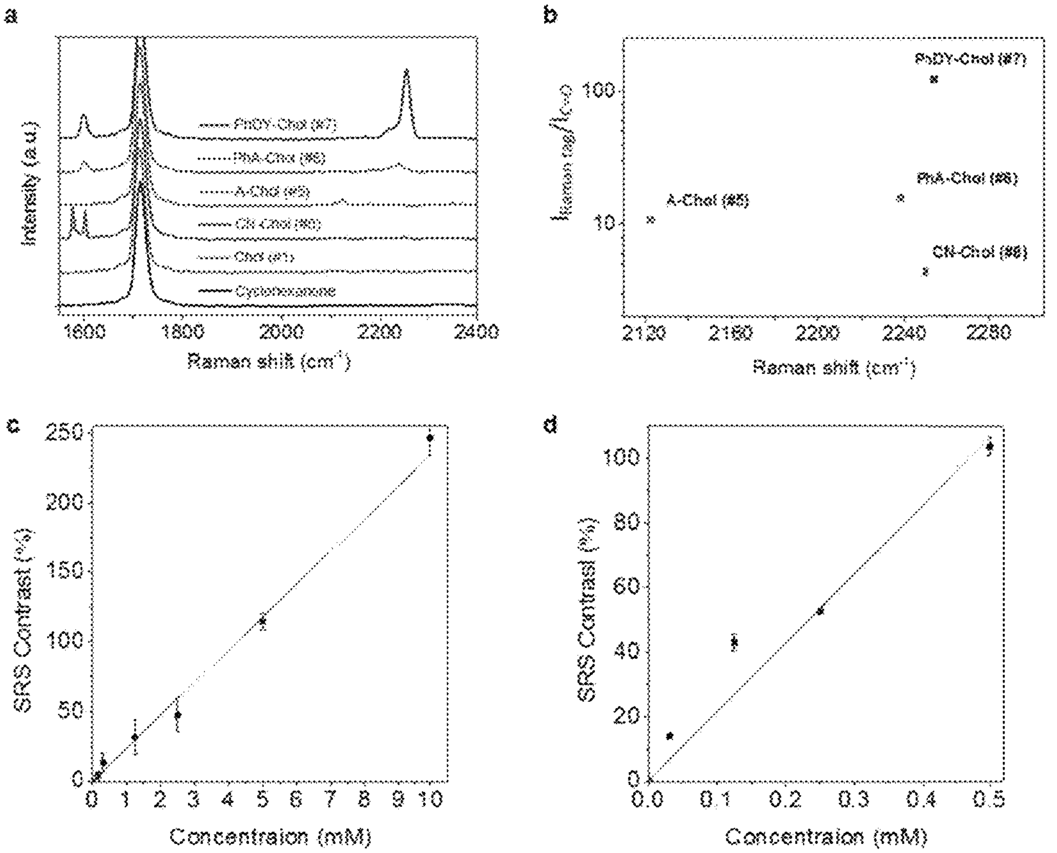
FIG. 2. Raman spectral analysis of tagged cholesterol and SRS detection of PhDY-Chol. (a) Raman spectra of 50 mM tagged cholesterols in cyclohexanone (solvent). Spectral intensity was normalized by C═O vibration band at 1,714 $cm^{-1}$. Spectral acquisition time: 10 s. (b) Plot of relative intensity of Raman tags versus solvent and Raman shifts of tagged cholesterols. Based on the molar concentration of the molecules (50 mM) and the solvent (9.7 M), the Raman intensities of C≡C from A-Chol, PhA-Chol, and PhDY-Chol are 11 times, 16 times, and 122 times higher than the C═O band from the solvent, respectively. CN: cyano; A: alkyne; PhA: phenyl-alkyne; PhDY: phenyl-diyne; Chol: cholesterol. (c) SRS contrast versus concentration plot of PhDY-Chol solutions. 13% contrast was reached at 313 μM and 4% contrast was reached at 156 μM. Image acquisition speed: 200 μs per pixel. Data represents the mean±SEM in 3 measurements. $R^2$=0.996. (d) SRS contrast versus concentration plot of PhDY-Chol solutions using chirped femtosecond lasers with spectral focusing approach. 14% contrast was reached at 31 μM. Image acquisition speed: 200 μs per pixel. Data represents the mean±SEM in 3 measurements. $R^2$=0.980. Contrast was defined as (S−B)/B. S: SRS signal; B: background.

Referring now to FIG. 2, to determine the Raman shift of the C≡C stretching vibrational mode and to compare the level of Raman signals from the cholesterol mimics, 50 mM of each compound was prepared in cyclohexanone and confocal Raman spectral analysis was performed. The signal from CN-Chol was too weak to be detected. A-Chol showed its peak for C≡C vibrational mode at 2,122 $cm^{-1}$; PhA-Chol at 2,239 $cm^{-1}$; PhDY-Chol at 2,254 $cm^{-1}$. Comparing the Raman peak of each tag to the 1,714 $cm^{-1}$ C═O vibrational peak from the solvent (9.7 M for pure cyclohexanone), the alkyne, PhA, and PhDY groups were 11 times, 16 times, and 122 times stronger in Raman intensity, respectively. This showed that the PhDY tag produces a spectrally-isolated peak, which is stronger than the C═O vibrational mode by two orders of magnitude.

To determine the SRS imaging sensitivity for PhDY-Chol, we used a femtosecond stimulated Raman loss (SRL) microscope reported elsewhere. Cyclohexanone solutions of PhDY-Chol were prepared by serial dilution, and SRS images of PhDY-Chol were recorded with the laser beating frequency tuned to be resonant with C≡C vibration at 2,252 $cm^{-1}$. In solutions without PhDY-Chol, a residual background was detected, caused by cross phase modulation. The SRS contrast, defined as (S−B)/B, where S and B denote SRS signal and background, was calculated as a function of PhDY-Chol molar concentration. At the speed of 200 μs per pixel, a linear relationship was observed and 13% and 4% contrasts were reached at 313 μM and 156 μM, respectively. To increase the detection sensitivity, we chirped the femtosecond lasers to 0.8 picosecond with a SF-10 glass rod. This spectral focusing approach maintained 85% of the SRS signal while reduced the cross phase modulation background level by 3 times, to a level of $6.3\times10^{-7}$ in terms of modulation depth. As a result, the SRS contrast became 14% at 31 μM, corresponding to ~1,800 molecules in the excitation volume. We also depicted the modulation depth (ΔI/I) as a function of molar concentration (FIG. 8). which is used for estimating the molar concentration of PhDY-Chol inside cells in following studies.

Cytoxicity Analysis of the Cholesterol Mimics

Figure 3:
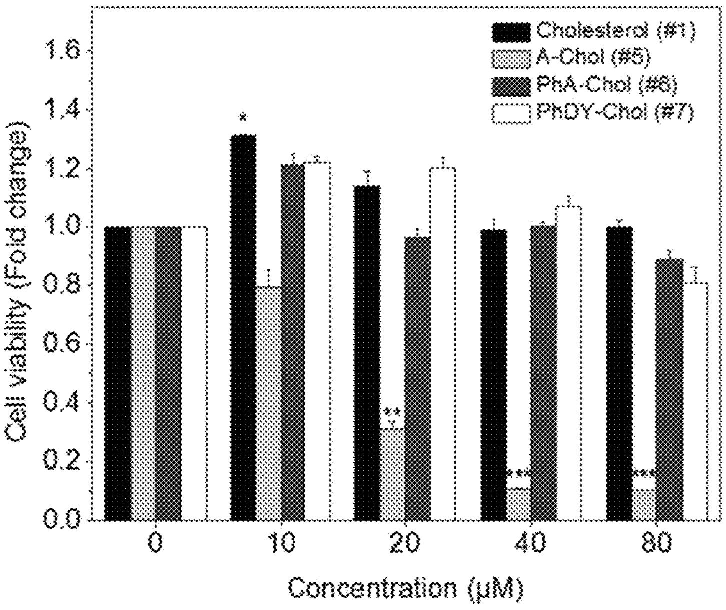
FIG. 3. Cell-viability assays showing that phenyl group reduces cytotoxicity of the probes. MTT Cell-viability assays show that A-Chol is toxic to the cells, but phenyl group prevents the cytotoxicity. CHO cells were incubated with each probe in various concentrations for 48 h before MTT cell-viability assays were conducted. Error bars represent standard error of the mean (SEM). n>3, *: $p<0.05$; : $p<0.005$; *: $p<0.0005$. A: alkyne; PhA: phenyl-alkyne; PhDY: phenyl-diyne; Chol: cholesterol.

Referring now to FIG. 3, the cytotoxicity of cholesterol mimics was evaluated by MTT cell-viability assays after treating CHO cells with cholesterol mimic. Various concentrations of cholesterol mimic were added to the culture media and the cells were incubated for 48 hours before the assays were conducted. A-Chol was found to be toxic to the cells with $IC_{50}$ of 16 μM. Adding a phenyl group reduced the cytotoxicity. To directly visualize the toxic effect, we stained the cells with propidium iodide for late apoptosis and necrosis. Cells incubated with A-Chol showed reduced density and extensive apoptosis, whereas both PhA and PhDY caused minimum cell death FIG. 9. This result presents another important role of the phenyl group, which is to reduce the toxicity caused by terminal alkyne.

Membrane Incorporation of Cholesterol Mimics

Figure 4:
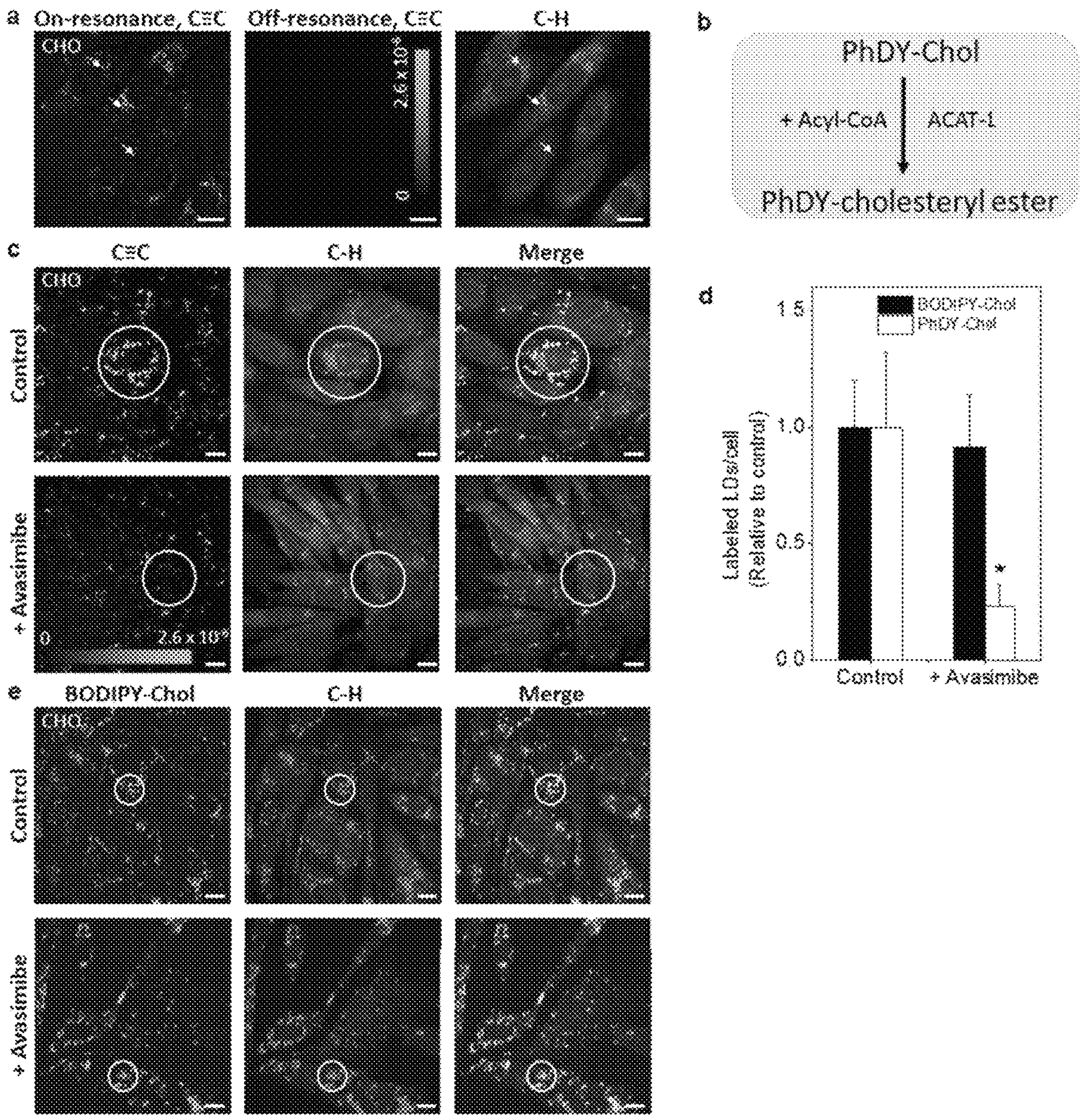
FIG. 4. SRS images of PhDY-Chol in live CHO cells and blockage of PhDY-Chol storage into LDs via ACAT-1 inhibition. (a) SRS images of live CHO cells treated with PhDY-Chol (50 μM) for 16 h. C≡C vibrational mode at 2,252 $cm^{-1}$ was used for PhDY-Chol, and C—H vibrational mode at 2,885 $cm^{-1}$ was used for C—H-rich lipid structures. Lasers were also tuned away to 2,099 $cm^{-1}$ to show specificity of PhDY-Chol signal inside the cells. PhDY-Chol was found to accumulate in LDs (arrows). Image acquisition speed: 10 μs per pixel for 512×512 pixels. Scalar bar: 10 μm.

Referring now to FIG. 4, CHO cells which are commonly used for cholesterol trafficking and metabolism studies, were used in these studies. To enhance cellular uptake of PhDY-Chol, the cells were pre-incubated in medium supplemented with lipoprotein-deficient serum to deplete medium cholesterol, after which the cells were incubated with 50 μM PhDY-Chol for 16 hours. By tuning the laser beating frequency to be resonant with C≡C vibration (2,252 $cm^{-1}$), SRL signals arose from PhDY-Chol. We also tuned the laser to be resonant with C-H vibration (2,885 $cm^{-1}$) and obtained signals from C-H-rich lipid structures, such as LDs.

To show the incorporation of PhDY-Chol into the plasma membrane, the cells were trypsinized and performed spectral-focusing SRS imaging of the rounded live CHO cells with 10 μs per pixel speed. PhDY-Chol in the membrane was detected in the on-resonance image, and the contrast disappeared in the off-resonance image. The membrane incorporation was confirmed by filipin staining of free cholesterol and Raman spectral analysis (FIG. 10). By focusing at the filipin-stained membrane, we have obtained the Raman spectrum showing the C═C band from filipin, the amide I band from protein, and the C≡C band from the PhDY (FIG. 10). Inside live CHO cells, PhDY-Chol was colocalized with LDs found in the C—H vibrational region, as shown in FIG. 4. This colocalization was confirmed by two-photon-excited fluorescence (TPEF) imaging and Raman spectral analysis of BODIPY-stained LDs in fixed CHO cells. (FIG. 10). The Raman spectrum of the BODIPY-labeled LDs showed the C═C band from BODIPY, 702 $cm^{-1}$ peak from cholesterol ring, and the C≡C band from the PhDY (FIG. 11), which further supports the localization of PhDY-Chol in LDs.

It is important to note that PhDY-Chol-rich structures inside the CHO cells could not be stained by filipin (FIG. 12), indicating that it is not in the free form. It is hypothesized that PhDY-Chol is converted into PhDY-cholesteryl ester, by ACAT-1, the enzyme responsible for cholesterol esterification, as diagrammed in FIG. 4. To confirm the esterification of PhDY-Chol, we inhibited ACAT-1 with avasimibe for 24 h before addition of PhDY-Chol. After blocking cholesterol esterification, the amount of PhDY-Chol found in CHO cells significantly decreased (FIG. 4*c*). Although LDs were still visible, the amount of PhDY-Chol signal found inside LDs reduced by 4 times (FIG. 4*d*). ACAT-1 knockdown by shRNA was also conducted to specifically inhibit the enzyme. Similarly, we found decreased amount of PhDY-Chol in ACAT-1 knocked down CHO cells, and the amount of PhDY-Chol in LDs reduced significantly (FIG. 12). To determine where PhDY-Chol accumulates after ACAT-1 inhibition, we stained the cells with LysoTracker for lysosomes. Our results indicated that after ACAT-1 inhibition, PhDY-Chol partially located in lysosomes (FIG. 12). Collectively, these results show that PhDY-Chol can be transported into cells, converted into PhDY-cholesteryl ester by ACAT-1, and stored in LDs following the normal metabolic pathway of cholesterol. To emphasize the physiological compatibility of our PhDY tag, we treated CHO cells with BODIPY-cholesterol. The amount of BODIPY-cholesterol incorporated into LDs did not change after ACAT-1 inhibition (FIGS. 4*d* and *e*), indicating that BODIPY-cholesterol directly labels the LDs without metabolic conversion into cholesteryl ester.

Lysosomal accumulation and relocation to Lipid Droplets in NP—C animal disease model discovery using cholesterol mimics.

Referring now to FIG. 5, the potential of PhDY-Chol for studying cholesterol transport in NP-C disease, a disorder featured by abnormal cholesterol accumulation in late endosome/lysosome caused by mutation in NPC1 or 2 gene, was explored. M12 cells, mutant CHO cells that contain a deletion of the NPC1 locus, were established as a cellular model of the NP-C disease. By combining SRL imaging of PhDY with TPEF imaging of filipin, we observed that, unlike wildtype CHO cells, the PhDY-Chol-rich structures were stained by filipin, indicating that these PhDY-Chol molecules were located in lysosomes. (FIG. 13). Moreover, we observed some filipin labeled structures that do not contain PhDY-Chol. This result is reasonable given that filipin has been shown to label other lipid molecules, such as glycosphingolipids. As additional evidence, we incubated M12 cells with PhDY-Chol and stained the cells with LysoTracker. It was found that all PhDY-Chol-rich areas were localized in LysoTracker-stained organelles (FIG. 13). Collectively, these results showed that PhDY-Chol can selectively represent the lysosomal storage of cholesterol in the NP-C disease model.

We then treated the PhDY-Chol-labeled M12 cells with a cholesterol-mobilizing drug, hydroxypropyl-β-cyclodextrin (HPβCD). This drug is known to mediate lysosomal escape of cholesterol, and promote storage of excess cholesterol into LDs. After treating with HPβCD, the amount of PhDY-Chol in M12 cells decreased by half (FIG. 5*b* and *c*). Interestingly, we observed that some PhDY-Chol-rich areas were not labeled by filipin after HPβCD treatment (FIG. 5*b*, arrow heads). These areas likely represent PhDY-cholesteryl ester stored in LDs. To confirm this possibility, we stained the cells with BODIPY for localization of LDs. The result clearly showed that PhDY-Chol moved into LDs after HPβCD treatment, and the number of PhDY-rich LDs increased significantly (FIGS. 5*d* and *e*). Together, these data indicate that PhDY-Chol can be used as a reliable probe molecule to study cholesterol mobilization inside living cells.

Cholesterol mimics identify cholesterol storage compartments in animal model.

Referring to FIG. 6, to demonstrate the capability of monitoring cholesterol uptake and distribution in vivo, we fed N2 wildtype *C. elegans* with PhDY-Chol-labeled *E. coli* and imaged PhDY-Chol storage in the worms using our SRL microscope at speed of 40 μs per pixel. PhDY-Chol was found to be stored in the intestinal cells inside the wildtype worms (FIG. 6*a*, upper panels). To confirm the uptake of PhDY-Chol by intestinal cells, we fed mutant *C. elegans*, in which dietary cholesterol uptake is inhibited by ChUP-1 deletion, with PhDY-Chol. We did not observe PhDY-Chol inside this strain (FIG. 6*a*, lower panels), which indicates that the PhDY tag did not affect the cholesterol uptake process. Then, we tuned the laser to be resonant with C-H vibration for lipid-rich LDs. Unlike wildtype CHO cells, the PhDY-Chol-rich compartments were found to be distinguished from LDs in wildtype worms (FIG. 6*a*, upper panels). To explore the nature of these compartments, we used hjIs9 worms that contains GFP targeted to lysosome-related organelles (LROs) in intestinal cells. Dual-modality SRS and TPEF imaging showed that PhDY-Chol is stored in the LROs (FIG. 6*b*). Collectively, these results suggest that dietary PhDY-Chol uptake is through a ChUP-1 mediated process, and unlike mammalian CHO cells, *C. elegans* stores cholesterol in LROs, but not in LDs in the intestine.

Chemical structure (V) or Compound S8. The mixture of 4 (22 mg, 0.05 mmol), $PdCl_2(PPh_3)_2$ (1.4 mg, 0.002 mmol), CuI (0.4 mg, 0.002 mmol), and B (12.3 mg, 0.06 mmol) in THF (0.5 mL) was bubbled with Argon gas for ten minutes. To the mixture, DIPEA (0.02 mL) was added at room temperature. After stirring for 2 h at room temperature, the reaction was quenched with saturated $NH_4Cl$ aqueous solution and extracted with ethyl acetate. The organic layer was washed with brine, dried over $MgSO_4$. The solvent was removed under vacuum, and the residue was purified by chromatography (Hexane/EtOAc, 40:1) to give S8 (18 mg, 65%) as a white solid.

(V)

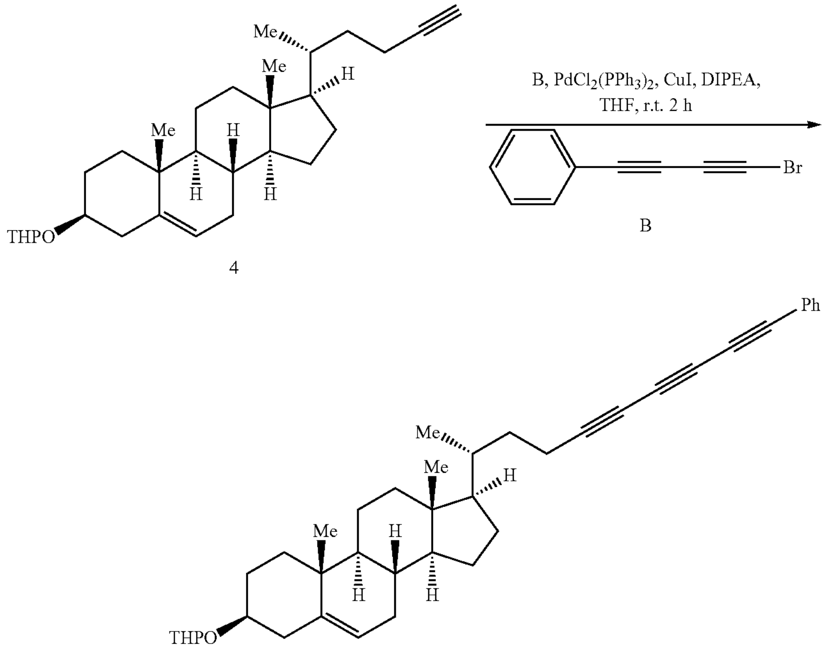

4

B

S8

$^{1}$H NMR (500 MHz, $CDCl_3$): δ 7.50 (d, J=7.0 Hz, 2H), 7.38-7.35 (m, 1H), 7.33-7.30 (m, 2H), 5.35 (t, J=6.5 Hz, 1H), 4.72 (m, 1H), 3.93-3.90 (m, 1H), 3.55-3.47 (m, 2H), 2.44-2.20 (m, 4H), 2.01-1.96 (m, 2H), 1.88-1.83 (m, 4H), 1.74-1.70 (m, 2H), 1.62-1.42 (m, 12H), 1.30-1.06 (m, 7H), 1.01 (s, 3H), 0.93 (d, J=6.5 Hz, 3H), 0.69 (s, 3H); $^{13}$C NMR (100 MHz, $CDCl_3$): δ 141.2, 141.1, 133.1, 129.6, 128.6, 121.7, 121.6, 121.4, 108.8, 97.2, 97.0, 83.3, 76.2, 75.5, 74.8, 67.6, 65.6, 63.1, 63.0, 59.6, 56.9, 56.0, 53.6, 50.3, 50.3, 42.6, 40.4, 40.0, 38.9, 37.6, 37.4, 37.0, 36.9, 35.4, 34.5, 32.0, 31.4, 29.8, 28.3, 28.1, 25.6, 24.4, 21.2, 20.3, 20.2, 19.5, 18.3, 16.8, 12.0; IR (film): 2958, 2925, 2326, 2125, 1643, 1457, 1379, 1016 $cm^{-1}$; MS (ESI): m/z 585 $[M+Na]^+$.

for Raman imaging in a low-concentration condition. It has been reported that as the chain length increases, the hyperpolarizability increases in polyynes. Also, aromatic ring capped alkyne was shown to give stronger Raman signals than terminal alkyne. To design tagged cholesterol with very strong Raman intensity, we calculated the Raman cross section of potential tags—alkyne, phenyl-alkyne, diyne, phenyl-diyne using the Q-Chem and GAMESS electronic structure packages to provide insight of the relation between molecular structure and Raman intensity. Our results show that the localized polarizabilities on each C≡C moiety increase with the number of conjugated triple bonds, as well as with addiction of a phenyl ring (FIG. 7*a* and Table 1).

(VI)

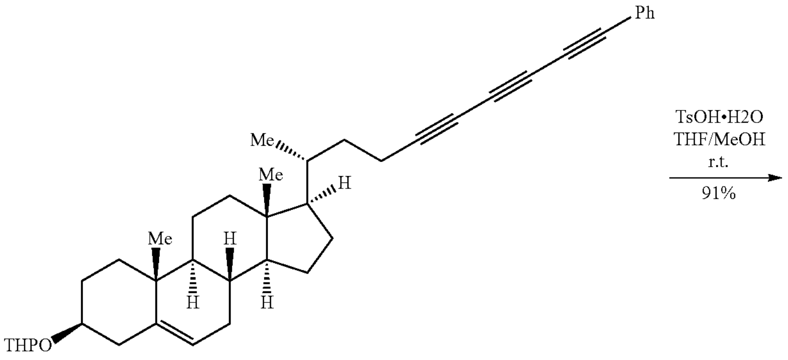

S8

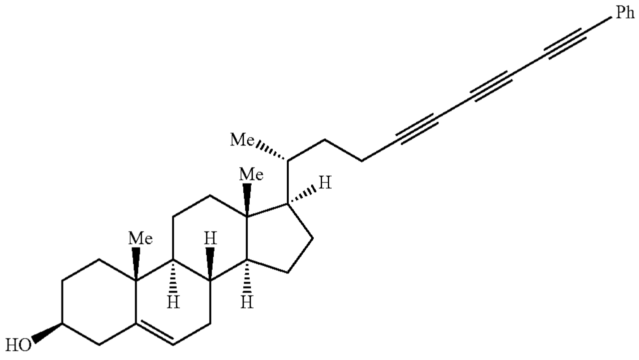

9

Additional disclosure and drawings can be found in the following paragraphs and updated drawings submitted herewith. They are part of the provisional application with the Ser. No. of 62/048,484 that the instant application claims benefits from and incorporated herein entirely.

Rational Design and Synthesis of Tagged Cholesterol with an Extremely Large Raman Scattering Cross Section In order to design a probe molecule that not only maintains physiological functions of cholesterol, but also has a large Raman scattering cross section, we chose to replace the aliphatic side chain of cholesterol with a cyano or alkynyl groups (FIG. 1). These group have small size, which could minimize structural perturbation of the molecule of interest, in this case, cholesterol. Meanwhile, these groups produce strong Raman scattering peaks in a cellular silent region (1,800-2,800 $cm^{-1}$), and therefore, can potentially be used Thus, the total polarizahility of the molecule increases as a result of the additive effect as well as non-linear boost in the polarizability of conjugated bonds. The phenyl ring serves as both a donor and an acceptor of π-electrons from the neighboring triple bonds, further escalating polarizabilities of neighboring conjugated bonds. Taking into account that the Raman intensity is proportional to squares of polarizability derivatives, the additional three-fold enhancement of the total polarizability due to conjugation results in a ~10-fold boost in Raman intensity. Together, the Raman intensity increases by 9 times by adding a phenyl group to the terminal alkyne, and 52 times by conjugating a phenyl group and another alkyne (FIG. 7*b*).

Supplementary Table 1. Distributed Polarizabilities of C≡C and Phenyl Moieties Calculated as Sums of Polarizabilities of Localized π-orbitals in Various Tags Supplementary Table 1.
Distributed polarizabilities of C≡C and phenyl moieties calculated as sums of polarizabilities of localized π-orbitals in various tags

| | XX | average |
|---|---|---|
| C≡C | 2.82 | 1.60 |
| C≡C—Ph | 7.42 | 3.76 |
| C≡C | 4.62 | 2.15 |
| Ph | 2.80 | 1.61 |
| C≡C—C≡C | 8.70 | 3.54 |
| C≡C | 4.35 | 1.77 |
| C≡C | 4.35 | 1.77 |
| C≡C—C≡C—Ph | 16.70 | 7.37 |
| left C≡C | 5.77 | 2.51 |
| middle C≡C | 7.20 | 2.95 |
| Ph | 3.73 | 1.91 |

XX: the largest components
Note:
The total polarizability of π-conjugated system increases as a result of the additive effect as well as non-linear boost in the polarizability of conjugated bonds.

Based on the above considerations, we have synthesized a series of tagged cholesterols-alkyne cholesterol (A-Chol, 5), phenyl-alkyne cholesterol (PhA-Chol, 6), phenyl-diyne cholesterol (PhDY-Chol, 7), and cyano cholesterol (CN-Chol, 8) as shown in FIG. 1. Our synthesis commenced with commercially available cholenic acid 3. Using a sequence of THP-protection, $LiAlH_4$ reduction, Dess-Martin oxidation and Seyferth-Gilbert-Bestmann homologation, cholenic acid 3 was converted to compound 4 with a terminal alkyne group in excellent yield. Removal of the THP-protecting group gave probe 5. We further prepared PhA-Chol 6 and PhDY-Chol 7 from compound 4 via a palladium-catalyzed Sonogashira reaction and a copper-catalyzed Cadiot-Chodkiewicz reaction, respectively, followed by acidic removal of THP group. Additionally, CN-Chol 8 was prepared from cholenic acid 3 via standard transformations.

Raman Spectral Analysis and SRS Imaging of Tagged Cholesterol

To determine the Raman shift of the C≡C stretching vibrational mode and to compare the level of Raman signals from the tagged cholesterols, we prepared 50 mM of each compound in cyclohexanone and performed confocal Raman spectral analysis (FIG. 2*a*). The signal from CN-Chol was too weak to be detected. A-Chol showed its peak for C≡C vibrational mode at 2,122 $cm^{-1}$; PhA-Chol at 2,239 $cm^{-1}$; PhDY-Chol at 2,254 $cm^{-1}$. (FIG. 2*a*). Comparing the Raman peak of each tag to the 1,714 $cm^{-1}$ C═O vibrational peak from the solvent (9.7 M for pure cyclohexanone), the alkyne, PhA, and PhDY groups were 11 times, 16 times, and 122 times stronger in Raman intensity, respectively. (FIG. 2*b*). This result showed that the PhDY tag produces a spectrally-isolated peak, which is stronger than the C═O vibrational mode by two orders of magnitude.

To determine the SRS imaging sensitivity for PhDY-Chol, we used a femtosecond stimulated Raman loss (SRL) microscope reported elsewhere[28]. Cyclohexanone solutions of PhDY-Chol were prepared by serial dilution, and SRS images of PhDY-Chol were recorded with the laser beating frequency tuned to be resonant with C≡C vibration at 2,252 $cm^{-1}$. In solutions without PhDY-Chol, a residual background was detected, caused by cross phase modulation. The SRS contrast, defined as (S−B)/B, where S and B denote SRS signal and background, was calculated as a function of PhDY-Chol molar concentration. At the speed of 200 μs per pixel, a linear relationship was observed (FIG. 2*c*) and 13% and 4% contrasts were reached at 313 μM and 156 μM, respectively. To increase the detection sensitivity, we chirped the femtosecond lasers to 0.8 picosecond with a SF-10 glass rod. This spectral focusing approach maintained 85% of the SRS signal while reduced the cross phase modulation background level by 3 times, to a level of $6.3\times10^{-7}$ in terms of modulation depth. As a result, the SRS contrast became 14% at 31 μM, corresponding to ~1,800 molecules in the excitation volume (FIG. 2*d*). We also depicted the modulation depth (ΔI/I) as a function of molar concentration (FIG. 8), which is used for estimating the molar concentration of PhDY-Chol inside cells in following studies.

Cytotoxicity Caused by Terminal Alkyne is Avoided by Phenyl Group

To evaluate the cytotoxicity of tagged cholesterols, we performed MTT cell-viability assays after treating CHO cells with tagged cholesterol. Various concentrations of tagged cholesterol were added to the culture media and the cells were incubated for 48 h before the assays were conducted. A-Chol was found to be toxic to the cells with $IC_{50}$ of 16 μM. Importantly, adding a phenyl group effectively reduced the cytotoxicity (FIG. 3). To directly visualize the toxic effect, we stained the cells with propidium iodide for late apoptosis and necrosis. Cells incubated with A-Chol showed reduced density and extensive apoptosis, whereas both PhA and PhDY caused minimum cell death (FIG. 9). This result presents another important role of the phenyl group, which is to reduce the toxicity caused by terminal alkyne. Based on the signal level and the severity of toxicity, we conclude that PhDY-Chol is the most suitable cholesterol probe for live cell imaging, and we used PhDY-Chol in subsequent experiments.

Membrane Incorporation and Esterification of PhDY-Chol in Live Cells

We chose CHO cells which are commonly used for cholesterol trafficking and metabolism studies. To enhance cellular uptake of PhDY-Chol, the cells were pre-incubated in medium supplemented with lipoprotein-deficient serum to deplete medium cholesterol, after which the cells were incubated with 50 μM PhDY-Chol for 16 h. By tuning the laser beating frequency to be resonant with C≡C vibration (2,252 $cm^{-1}$), SRL signals arose from PhDY-Chol. We also tuned the laser to be resonant with C—H vibration (2,885 $cm^{-1}$) and obtained signals from C—H-rich lipid structures, such as LDs.

To show the incorporation of PhDY-Clol into the plasma membrane, we trypsinized the cells and performed spectral-focusing. SRS imaging of the rounded live CHO cells with 10 μs per pixel speed. PhDY-Chol in the membrane was detected in the on-resonance image, and the contrast disappeared in the off-resonance image (FIG. 10*a*). The membrane incorporation was confirmed by filipin staining of free cholesterol and Raman spectal analysis (FIGS. 10*b* and *c*). By focusing at filipin-stained membrane, we have obtained the Raman spectrum showing the C═C band from filipin, the amide I band from protein, and the C≡C, band from the PhDY (FIG. 10*c*). Inside live CHO cells, PhDY-Chol was colocalized with LDs found in the C—H vibrational region (FIG. 4*a*). This colocalization was confirmed by two-photon-excited fluorescence (TPEF) imaging and Raman spectral analysis of BODIPY-stained LDs in fixed CHO cells. (FIG. 11*a*and *b*). The Raman spectrum of the BODIPY-labeled LDs showed the C═C band from BODIPY, 702 $cm^{-1}$ peak from cholesterol ring, and the C≡C band from the PhDY (FIG. 11*b*), which further supports the localization of PhDY-Chol in LDs.

It is important to note that PhDY-Chol-rich structures inside the CHO cells could not be stained by filipin (FIG.

10*b*), implicating that it is not in the free form. We hypothesize that PhDY-Chol is converted into PhDY-cholesteryl ester, by ACAT-1, the enzyme responsible for cholesterol esterification (FIG. 4*b*). To confirm the esterification of PhDY-Chol, we inhibited AcAT-1 with avasimibe for 24 h before addition of PhDY-Chol. After blocking cholesterol esterification, the amount of PhDY-Chol found in CHO cells significantly decreased (FIG. 4*c*). Although LDs were still visible, the amount of PhDY-Chol signal found inside LDs reduced by 4 times (FIG. 4*d*). ACAT-1 knockdown by shRNA was also conducted to specifically inhibit the enzyme. Similarly, we found decreased amount of PhDY-Chol in ACAT-1 knocked down CHO cells, and the amount of PhDY-Chol in LDs reduced significantly (FIG. 12*a*). To determine where PhDY-Chol accumulates after ACAT-1 inhibition, we stained the cells with LysoTracker for lysosomes. Our result indicated that after ACAT-1 inhibition, PhDY-Chol partially located in lysosomes (FIG. 12*b*). Collectively, these results show that PhDY-Chol can be transported into cells, converted into PhDY-cholesteryl ester by ACAT-1, and stored in LDs following the normal metabolic pathway of cholesterol. To emphasize the physiological compatibility of our PhDY tag, we treated CHO cells with BODIPY-cholesterol. The amount of BODIPY-cholesterol incorporated into LDs did not change after ACAT-1 inhibition (FIGS. 4*d* and 4*e*), indicating that BODIPY-cholesterol directly labels the LDs without metabolic conversion into cholesterol ester.

Lysosomal Accumulation and Relocation to LDs in NP-C Disease Model

Next, we explored the potential of PhDY-Chol for studying cholesterol transport in NP-C disease, a disorder featured by abnormal cholesterol accumulation in late endosome/lysosome caused by mutation in NPC1 or 2 gene[38]. M12 cells, mutant CHO cells that contain a deletion of the NPC1 locus, were established as a cellular model of the NP-C disease[39]. By combining SRL imaging of PhDY with TPEF imagine of filipin, we observed that, unlike wildtype CHO cells, the PhDY-Chol-rich structures were stained by filipin, indicating that these PhDY-Chol molecules were located in lysosomes, (FIG. 5*a*, FIGS. 13*a* and 13*b*). Moreover, we observed some filipin labeled structures that do not contain PhDY-Chol. This result is reasonable given that filipin has been shown to label other lipid molecules, such as glycosphingolipids[21]. As additional evidence, we incubated M12 cells with PhDY-Chol and stained the cells with LysoTracker. It was found that all PhDY-Chol-rich area were localized in LysoTracker-stained organelles (FIG. 13*c*). Collectively, these results showed that PhDY-Chol can selectively represent the lysosomal storage of cholesterol in the NP-C disease model.

We then treated the PhDY-Chol-labeled M12 cells with a cholesterol-mobilizing drug, HPβCD[40]. This drug is known to mediate lysosomal escape of cholesterol, and promote storage of excess cholesterol into LDs[41]. After treating with HPβCD, the amount of PhDy-Chol in M12 cells decreased by half (FIGS. 5*b* and *c*). Interestingly, we observed that some PhDY-Chol-rich area were not labeled filipin after HPβCD treatment (FIG. 5*b*, arrow heads). These areas likely represent PhDY-cholesteryl ester stored in LDs. To confirm this possibility, we stained the cells with BODIPY for localization of LDs. The result clearly showed that PhDY-Chol has moved into LDs after HPβCD treatment, and the number of PhDY-rich LDs increased significantly (FIGS. 5*d* and *e*). Together, these data indicate that PhDY-Chol can be used as a reliable probe molecule to study cholesterol mobilization inside living cells.

Cholesterol Storage Compartments in *C. elegans* Visualized by PhDY-Chol

Finally, to demonstrate the capability of monitoring cholesterol uptake and distribution in vivo, we fed N2 wildtype *C. elegans* with PhDY-Chol-labeled *E. coli* and imaged PhDY-Chol storage in the worms using our SRL microscope at speed of 40 μs per pixel. PhDY-Chol was found to he stored in the intestinal cells inside the wildtype worms (FIG. 6*a*, upper panels). To confirm the uptake of PhDY-Chol by intestinal cells, we fed mutant *C. elegan*, in which dietary cholesterol uptake is inhibited by ChUP-1 deletion, with PhDY-Chol. We did not observe PhDY-Clol inside this strain (FIG. 6*a*, lower panels), which indicates that the PhDY tag did not affect the cholesterol uptake process. Then, we tuned the laser to be resonant with C—H vibration for lipid-rich LDs. Unlike wildtype CHO cells, the PhDY-Chol-rich compartments were found to be distinguished from LDs in wildtype worns (FIG. 6*a*, upper panels). To explore the nature of these compartments, we used hjIs9 worms that contains GFP targeted to lysosome-related organelles (LROs) in intestinal cells[43]. Dual-modality SRS and TPEF imaging showed that PhDY-Chol is stored in the LROs (FIG. 6*b*). Collectively, these results suggest that dietary PhDY-Chol uptake is through a ChUP-1 mediated process, and unlike mammalian CHO cells, *C. elegans* stores cholesterol in LROs, but not in LDs in the intestine. We have developed a series of tagged cholesterols based on quantum chemistry calculations and chemical synthesis. By using PhDY to replace the aliphatic chain in cholesterol, we produced a cholesterol probe, PhDY-Chol, with a Raman signal that is two orders of magnitude stronger than the group C═O group. By SRS imaging of live CHO cells, PhDY-Chol was found to be incorporated into the membrane, and converted to PhDY-cholesteryl ester for storage in LDs. With this cholesterol probe, we experimentally validated that after ACAT-1 inhibition, cholesterol partly accumulates in lysosomes. In live NPCl-deleted CHO cells, PhDY-Chol selectively represented lysosomal accumulation of cholesterol in untreated cells, and esterification and relocation to LDs after HPβCD treatment. Lastly, SRS imaging of PhDY-Chol in live *C. elegans* identified LROs, but not LDs, as the cholesterol storage compartments in the intestine.

In this study, we have developed a series of tagged cholesterols based on quantum chemistry calculations and chemical synthesis. By using PhDY to replace the aliphatic chain in cholesterol, we produced a cholesterol probe, PhDY-Chol, with a Raman signal that is two orders of magnitude stronger than the C═O group. By SRS imaging of live CHO cells, PhDY-Chol was found to be incorporated into the membrane, and converted to PhDY-cholesteryl ester for storage in LDs. With this cholesterol probe, we experimentally validated that after ACAT-1 inhibition, cholesterol partly accumulates in lysosomes. In live NPCl-deleted CHO cells, PhDY-Chol selectively represented lysosomal accumulation of cholesterol in untreated cells, and esterification and relocation to LDs after HPβCD treatment. Lastly, SRS imaging of PhDY-Chol in live *C. elegans* identified LROs, but not LDs, as the cholesterol storage compartments in the intestine.

Essential parameters of a valid Raman tag include its amplitude of Raman scattering cross section, cytotoxicity, and biocompabbility. Although the C-D bond can be used to replace C—H bonds without changing the structures of the molecules, it gives relatively weak Raman intensities. Raman signal from alkyne bond is stronger than that from C-D bond by one order of magnitude, and detection at hundreds of μM of alkyne-containing molecules by SRS microscopy was reported. In our study, through rational design and synthesis of a PhDY tag, we increased the Raman scattering cross section by 11 times compared to the alkyne group, and 122 times compared to the endogenous C═O group. This enhancement is a result of conjugation of π-electrons among the two C≡C bonds and the phenyl group. As a result, we have been able to detect ~30 μM of PhDY-Chol molecules (~1,800 molecules at excitation volume), and demonstrated SRS imaging of PhDY-Chol in single membrane at speed of 10 μs per pixel. Importantly, this design also shielded the activity of terminal alkyne and significantly reduced cytotoxicity. Moreover, PhDY-Chol structurally mimics cholesterol, using the same physiological process for cholesterol transport and metabolism inside cells. Using the same strategy, other Raman tag molecules can be designed for sensitive and biocompatible probing of biomolecules in live cells.

The potential value of a Raman tag is also related to the detection sensitivity of SRS microscopy. One limitation comes from the cross phase modulation, which produces a background that reduces the contrast for the tag molecules. Although broadband femtosecond lasers provide high peak intensity to enhance the SRS signal, they also increase the amplitude of the cross phase modulation. As shown in our study, this background can be reduced by 3 times using spectral focusing. The spectral focusing approach also increases the spectral selectivity, reduces the photodamage, and provides opportunities to conduct hyperspectral SRS imaging.

In this study, we compared BODIPY-cholesterol and PhDY-Chol. Our results show that PhDY-Chol is stored in LDs via esterification which can be blocked by ACAT-1 inhibition. In contrast, BODIFY-cholesterol labels LDs even after ACAT-1 inhibition. This result may be due to the strong hydrophobic interaction of BODIPY with LDs, and is consistent with previous studies showing that BODIPY-cholesterol is hardly esterified by ACAT-1 inside the cells. We also showed that PhDY-Chol reflects the location of the cholesterol more specifically than filipin staining. Lastly, SRS microscopy utilizes chemical-bond vibrational signals for visualization. Thus, unlike fluorophores, the PhDY tag does not undergo bleaching (FIG. 14), in contrast to BODIPY-cholesterol and DHE which is known to have a rapid photo-bleaching rate. Combining these unique properties, PhDY-Chol allows quantitative imaging of intracellular cholesterol, and repetitive observation of the same sample before and after treatment.

It is worth discussing the new opportunities for study of the NP-C disease and genomic screening of cholesterol-related genes. NP-C disease is a fatal neurodegenerative disease that show extensive lysosomal accumulation of cholesterol, and early detection and treatment strategies are still under development. The involvement of lysosornal cholesterol accumulation to the neurodegeneration is still unclear. In this study, we have demonstrated in vitro study of cholesterol trafficking and metabolism in a cellular model. This can be extended to in vivo studies using mouse models to understand the progression of the disease and impact of potential therapeutic strategies, especially in central nervous system. *C. elegans* is an important model for genetic and chemical screening in many diseases, including NP-C disease. It has been proposed that the intracellular sterol trafficking pathway might be conserved in this animal model. However, imaging cholesterol in *C. elegans* has been a challenge due to strong autofluorescence from the worm. SRS imaging of PhDY-Chol opens an avenue to genome-wide RNA interference screening of *C. elegans* for cholesterol transport and storage genes in this animal model. Finally, our work also opens new opportunities to study cholesterol trafficking and metabolism in other animal models such as zebrafish and mice.

Methods

Calculation of Raman intensity. All calculations were performed at the HF/6-311G* level of theory. Geometry optimizations, vibrational frequencies and Raman intensities are obtained in Q-Chem electronic structure package. Localized polarizabilities are calculated in the GAMESS quantum chemistry software.

Chemicals. 3β-hydroxy-$\Delta^5$-cholenic acid was purchased from VWR. Lipoprotein-deficient serum was purchased from Biomedical Technologies Inc. Cholesterol, avasimibe, and filipin complex were purchased from Sigma-Aldrich. BODIPY-cholesterol was purchased from Avanti Polar Lipids, Inc. Propidium iodide, BODIPY, and LysoTracker were purchased from Life technologies.

Synthesis of Raman-tagged cholesterol. Detailed synthesis procedures and characterization of compounds are shown as following:

Synthesis of Cholesterol Mimics

General Methods. NMR spectra were recorded on ($^1$H at 400 MHz, 500 MHz and $^{13}$C at 100 MHz, 125 MHz) spectrometers. Chemical shifts (δ) were given in ppm with reference to solvent signals [$^1$H NMR: $CDCl_3$ (7.26); $^{13}$C NMR: $CDCl_3$ (77.2)]. Column chromatography was performed on silica gel. All reactions sensitive to air or moisture were carried out under argon atmosphere in dry and freshly distilled solvents under anhydrous conditions, unless otherwise noted. Anhydrous THF was distilled over sodium benzophenone ketyl under $N_2$. Anhydrous $CH_2Cl_2$ was distilled over calcium hydride under $N_2$. Anhydrous MeOH was distilled over magnesium under $N_2$. All other solvents and reagents were used as obtained from commercial sources without further purification.

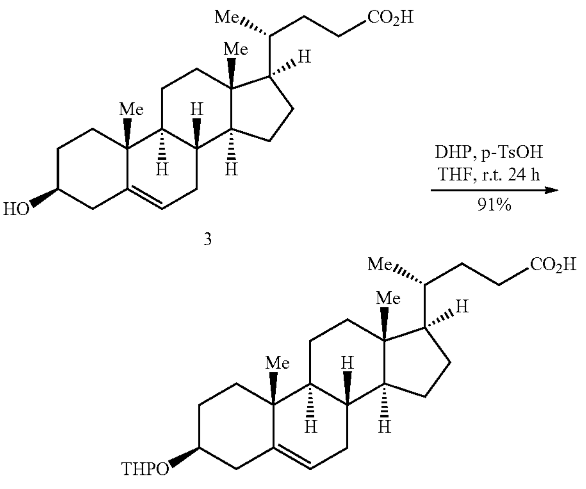

3

S1

Compound S1. To a solution of acid 3 (200 mg, 0.53 mmol) in dry THF (22.5 mL) were added 3,4-dihydro-2H-pyran (DHP) (0.24 mL 2.65 mmol) and p-toluenesulfonic acid monohydrate (p-TsOH) (20.2 mg, 0.11 mmol) under argon. After the mixture was stirred at room temperature for 24 h, saturated aqueous $NaHCO_3$ solution and $CH_2Cl_2$ were added to quench the reaction. The aqueous layer was extracted with $CH_2Cl_2$ (3x50 mL), and the combined organic layers were acidified with acetic acid (15 mL), washed with water (3×50 mL) and dried with $Na_2SO_4$. The solvent was removed under vacuum, and the residue was purified by chromatography (Hexane/EtOAc, 8:1) to give S1 (222 mg, 91%) as a white solid.

$^1$H NMR (500 MHz, $CDCl_3$): δ 5.35-5.33 (m, 1H), 4.74-4.71 (m, 1H), 3.93-3.90 (m, 1H), 3.54-3.46 (m, 1H), 2.42-2.19 (m, 4H), 1.98-1.71 (m, 9H), 1.61-1.43 (m, 12H), 135-1.07 (m, 7H), 1.00 (s, 3H), 0.93 (d, J=7.0 Hz, 3H), 0.67 (s, 3H); $^{13}$C NMR (100 MHz, $CDCl_3$): δ 180.0, 141.2, 121.7, 97.1, 96.9, 76.2, 63.0, 62.9, 56.9, 55.9, 50.3, 42.5, 40.4, 39.9, 38.9, 37.6, 37.4, 36.9, 35.5, 32.0, 31.4, 31.1, 30.9, 29.8, 28.2, 28.2, 28.1, 25.6, 24.4, 21.2, 20.1, 19.5, 18.4, 12.0; IR (film): 2938, 1708, 1454, 1200, 1059, 1033, 975 $cm^{-1}$: MS (ESI): m/z 457.4 $[M-H]^-$.

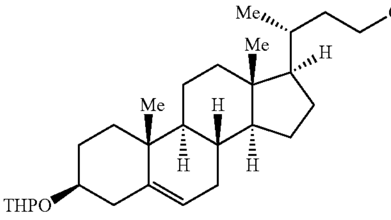

S1

$LiAlH_4$, THF
r.t. 12 h
98%

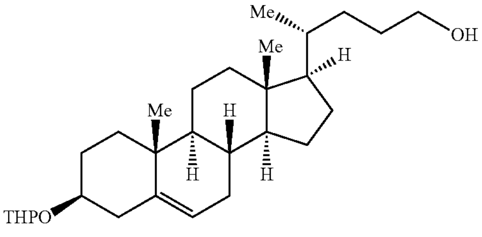

S2

Compound S2. A solution of S1 (222 mg, 0.48 mmol) in dry THF (12 mL) was added dropwise to a suspension of $LiAlH_4$ (55 mg, 1.45 mmol) in dry THF (8 mL) under argon at 0° C. After the addition, the reaction mixture was allowed to warm to room temperature and stirred overnight. Saturated aqueous $NaHCO_3$ solution (10 mL) was added slowly to quench the reaction, and the resulting mixture was extracted with $CH_2Cl_2$ (3×60 mL). The combined organic layers were washed with brine and dried with $Na_2SO_4$. The solvent was removed under vacuum, and the residue was purified by chromatography (Hexane/EtOAc, 4:1) to give S2 (209 mg, 98%) as a white solid.

$^1$H NMR (400 MHz, $CDCl_3$): δ 5.32 (t, J=6.0 Hz, 1H), 4.70 (s, 1H), 3.93-3.86 (m, 1H), 3.58 (td, J=9.2, 2.8 Hz, 2H), 3.52-3.45 (m, 2H), 2.34-2.18 (m, 2H), 1.97-1.81 (m, 8H), 1.57-1.38 (m, 16H), 1.23-1.05 (m, 6H), 0.98 (s, 3H, 0.92 (d, J=6.4 Hz, 3H), 0.66 (s, 3H); $^{13}$C NMR (100 MHz, $CDCl_3$): δ 141.2, 141.0, 121.6, 121.6, 97.1, 96.9, 76.1, 63.6, 63.0, 62.9, 56.8, 56.1, 50.3, 50.2, 42.4, 40.3, 39.9, 38.9, 37.6, 37.3, 36.9, 36.9, 35.7, 32.0, 32.0, 31.4, 29.8, 29,5. 28.3, 28.1, 25.6, 24.4, 21.2, 20.2, 20.1, 19.5, 18.8, 12.0; IR (film): 2936, 1456, 1377, 1112, 1059, 1033 $cm^{-1}$; MS (ESI): m/z 467.4 $[M+Na]^+$.

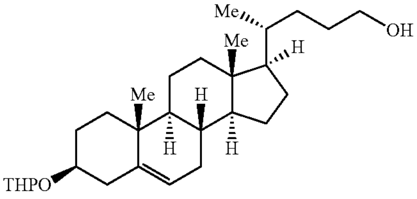

S2

DMP, $NaHCO_3$
DCM, 0° C.
86%

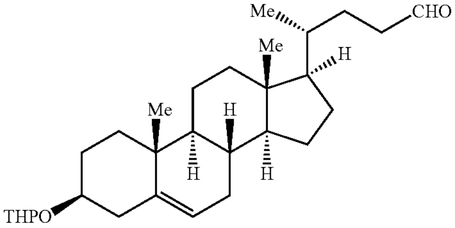

S3

Compound S3. To a suspension of S2 (79 mg, 0.18 mmol) and $NaHCO_3$ (45 mg, 0.53 mmol) in $CH_2Cl_2$ (4 mL) was added freshly prepared Dess-Martin Periodinane (113 mg, 0.27 mmol) at 0°C. The reaction mixture was stirred at 0°C. After the reaction is complete, saturated aqueous $NaHCO_3$ solution (10 mL) and saturated aqueous $Na_2S_2O_3$ solution (10 ml) were added and allowed to stir for 30 min at room temperature. Two layers were separated and the aqueous layer was washed with EtOAc (2×40 mL). The combined organic layers were washed with saturated aqueous $NaHCO_3$ solution (2×30 mL), brine and dried with $Na_2SO_4$. The solvent was removed under vacuum, and the residue was purified by chromatography (Hexane/EtOAc, 4:1) to give S3 (68 mg, 86%) as a white solid.

$^1$H NMR (400 MHz, $CDCl_3$): δ 9.75 (t, J=2.0 Hz, 1H), 5.33 (td, J=5.2, 1.6 Hz, 1H), 4.70 (t, J=3.6 Hz, 1H), 3.93-3.87 (m, 1H), 3.55-3.44 (m, 2H), 2.44-2.18 (m, 4H), 1.99-1.93 (m, 2H), 1.84-1.69 (m, 6H), 1.57-1.42 (m, 12H), 1.33-1.05 (m, 7H), 0.99 (s, 3H), 0.91 (d, J=6.4 Hz, 3H), 0.66 (s, 3H); $^{13}$C NMR (100 MHz, $CDCl_3$): δ 203.2, 141.2, 142.0, 121.6, 121.5, 97.1, 96.9, 76.1, 63.0, 63.0, 56.8, 55.9, 50.2, 50.2, 42.5, 41.0, 40.4, 39.8, 38.9, 37.6, 37.3, 36.9, 36.9, 35.4, 32.0, 31.4, 29.8, 28.3, 28.1, 25.6, 24.4, 21.1, 20.2, 20.1, 19.5, 18.5, 12.9; IR (film): 2936, 2867, 1726, 1440, 1199, 1134, 1033, 1025, 976 $cm^{-1}$; MS (ESI): m/z 441.1 $[M-H]^-$.

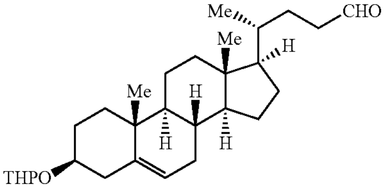

S3

Bestmann Reagent
$K_2CO_3$, MeOH/THF
r.t.
99%

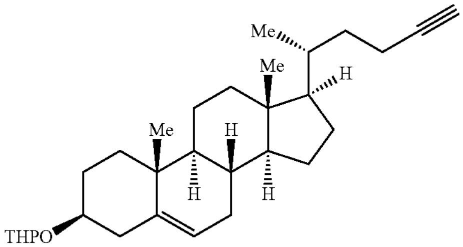

4

Compound 4. To a solution of S3 (415 mg, 0.914 mmol) and $K_2CO_3$ (504.6 mg, 3.66 mmol) in dry methanol (14 mL) and THF (14 mL) were added dimethyl-1-diazo-2-oxopropylphosphonate (Bestmann Reagent, 0.33 mL, 2.194 mmol) and stirred under room temperature. After the reaction was complete, the reaction was diluted with EtOAc, washed with saturated aqueous $NaHCO_3$ solution, and dried over $MgSO_4$. The solvent was removed under vacuum, and the residue was purified by chromatography (Hexane/EtOAc, 20:1) to give 4 (397 mg, 99%) as a white solid.

$^1$H NMR (500 MHz, $CDCl_3$); δ 5.35-5.32 (m, 1H), 4.71-4.70 (m, 1H), 3.93-3.88 (m, 1H), 3.53-3.46 (m, 2H), 2.35-2.09 (m, 4H), 2.00-1.82 (m, 7H), 1.73-1.70 (m, 2H), 1.64-1.40 (m, 12H), 1.30-1.05 (m, 7H), 1.00 (s, 3H), 0.92 (d, J=6.5 Hz, 3H), 0.68 (s, 3H); $^{13}$C NMR (125 MHz, $CDCl_3$): δ 141.2, 141.0, 121.6, 121.6, 97.1, 96.9, 85.3, 76.1, 68.0, 63.0, 62.9, 56.8, 56.0, 50.3, 50.2, 42.6, 40.4, 39.9, 38.9, 37.6, 37.3, 36.9, 36.9, 35.3, 35.0, 32.0, 32.0, 31.4, 28.3, 28.1, 25.6, 24.4, 21.2, 20.2, 20.2, 19.5, 18.3, 15.6, 12.0; IR (film): 3311, 2935, 2868, 2850, 2118, 1466, 1454, 1440, 1376, 1114, 1057, 869 $cm^{-1}$; MS (ESI): m/z 461.4 [M+Na]$^+$.

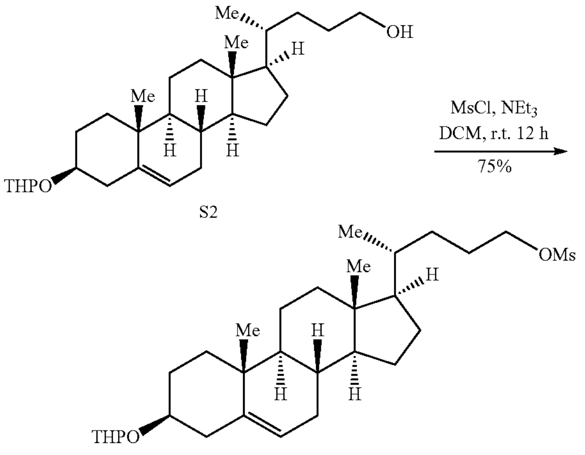

S2
S4

Compound S4. To a solution of S2 (100 mg, 0.225 mmol) and triethylamine (0.094 mL, 0.676 mmol) in $CH_2Cl_2$ (5 mL) was added methanesulfonyl chloride (77.4 mg, 0.676 mmol) under 0° C. After the addition, the reaction mixture was allowed to warm to room temperature and stirred overnight. Saturated aqueous $NaHCO_3$ solution was added to quench the reaction, and the resulting mixture was extracted with ethyl ether. The combined organic layers were washed with brine and dried with $MgSO_4$. The solvent was removed under vacuum, and the residue was purified by chromatography (Hexane/EtOAc, 8:1) to give 7 (88 mg, 75%) as a white solid.

$^1$H NMR (400 MHz, $CDCl_3$): δ 5.33 (t, J=4.8 Hz, 1H), 4.70 (s, 1H), 4.19 (dd, J=10.0, 5.2 Hz, 2H), 3.92-3.89 (m, 1H), 3.54-3.46 (m, 2H), 2.99 (s, 3H), 2.35-2.16 (m, 2H), 2.00-1.94 (m, 2H), 1.85-1.79 (m, 5H), 1.70-1.44 (m, 15H), 1.24-1.08 (m, 7H), 1.00 (s, 3H), 0.93 (d, J=5.2 Hz, 3H), 0.67 (s, 3H); $^{13}$C NMR (125 MHz, $CDCl_3$); δ 141.2, 141.0, 121.6, 121.6, 97.1, 97.0, 76.1, 70.8, 63.0, 63.0, 56.8, 55.9, 50.2, 42.5, 40.4, 39.9, 38.9, 37.5, 37.3, 36.9, 35.4, 32.0, 31.6, 31.4, 29.8, 28.3, 28.1, 26.0, 25.6, 25.6, 24.4, 21.2, 20.2, 19.5, 18.7, 12.0; IR (film): 2937, 2881, 2858, 1355, 1034, 962, 837 $cm^{-1}$; MS (ESI); m/z 545.4 [M+Na]$^+$.

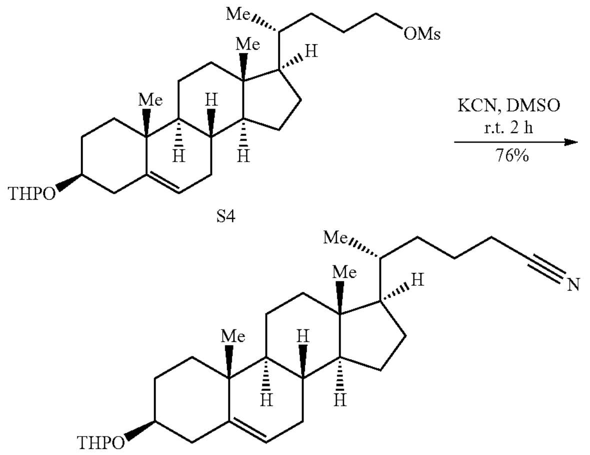

S4
S5

Compound S5. To a solution of S4 (40 mg, 0.077 mmol) in DMSO (1.5 mL) was added potassium cyanide (10 mg, 0.153 mmol). After the addition, the reaction mixture was heated to 90°C and stirred for 2 h. Water (5 mL) was added to quench the reaction, and the resulting, mixture was extracted with ethyl acetate (4×4 mL). The combined organic layers were washed with brine and dried with $MgSO_4$. The solvent was removed under vacuum, and the residue was purified by chromatography (Hexane/EtOAc, 8:1) to give S4 (27 mg, 76%) as a white solid.

$^1$H NMR (500 MHz, $CDCl_3$): δ 5.34 (dd, J=6.8, 4.4 Hz, 1H), 4.72-4.70 (m, 1H), 3.94-3.89 (m, 1H), 3.55-3.46 (m, 2H), 2.36-2.16 (m, 4H), 2.00-1.94 (m, 2H), 1.87-1.83 (m, 4H), 1.73-1.68 (m, 2H), 1.62-1.41 (m, 14H), 1.30-1.04 (m, 7H), 1.00 (s, 3H), 0.93 (d, J=6.5 Hz, 3H), 0.68 (s, 3H); $^{13}$C NMR (125 MHz, $CDCl_3$); δ 141.2, 141.0, 121.6, 121.6, 120.0, 97.1, 97.0, 76.1, 63.1, 63.0, 56.8, 56.0, 50.3, 50.2, 42.5, 40.4, 39.9, 39.0, 37.6, 37.3, 36.9, 36.9, 35.4, 35.2, 32.0, 31.4, 29.8, 28.3, 28.1, 25.6, 24.4, 22.3, 21.2, 20.2, 20.2, 19.5, 18.7, 17.7, 12.0; IR film): 2924, 2854, 2352, 2323, 1456, 1033, 1021, 973 $cm^{-1}$; MS (ESI); m/z 476.4 [M+Na]$^+$.

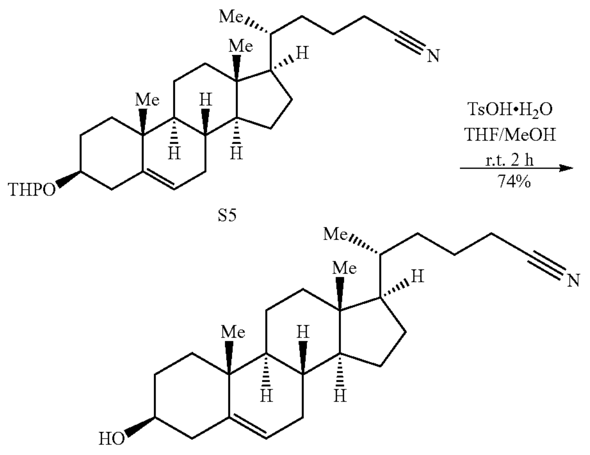

S5
8

Compound 8. S5 (20 mg, 0.044 mmol) and p-toluenesulfonic acid monohydrate (1.68 mg, 0.009 mmol) were dissolved in THF (0.5 mL) and methanol (0.5 mL), and stirred under room temperature. After the reaction is complete (2 h), the reaction mixture was diluted with ethyl ether, washed with saturated aqueous $NaHCO_3$ solution, and dried with $MgSO_4$. The solvent was removed under vacuum, and the residue was purified by chromatography (Hexane/EtOAc, 4:1) to give 8 (16 mg, 74%) as a white solid.

$^1H$ NMR (400 MHz, $CDCl_3$): δ 5.35 (dt, J=5.2, 2.0 Hz, 1H), 3.53 (tt, J=11.2, 4.4 Hz, 1H), 2.33-2.23 (m, 4H), 2.01-1.95 (m, 2H), 1.86-1.69 (m, 5H), 1.63-1.41 (m, 10 H), 1.29-1.05 (m, 7H), 1.00 (s, 3H), 0.94 (d, J=6.4 Hz, 3H), 0.68 (s, 3H); $^{13}C$ NMR (100 MHz, $CDCl_3$); δ 140.9, 121.8, 120.0, 71.9, 56.9, 55.9, 50.2, 42.5, 42.4, 39.9, 37.4, 36.6, 35.4, 35.2, 32.0, 31.8, 28.4, 24.4, 22.4, 21.2, 19.5, 18.7, 17.7, 12.0; IR (film): 2939, 2890, 2345, 2316, 1465, 1063, 960 $cm^{-1}$; MS (ESI): m/z 368.2 $[M-H]^-$.

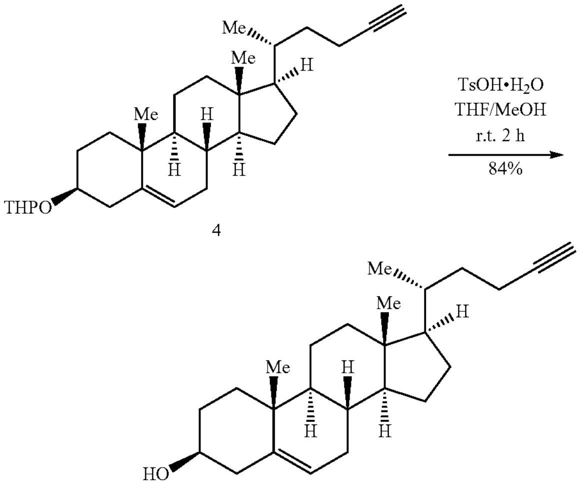

4

5

Compound 5. Compound 4 (53 mg, 0.121 mmol) and p-toluenesulfonic acid monohydrate (4.6 mg, 0.024 mmol) were dissolved in THF (1 mL) and methanol (1 mL), and stirred under room tem temperature. After the reaction is complete (2 h), the reaction mixture was diluted with ethyl ether, washed with saturated aqueous $NaHCO_3$ solution, and dried with $MgSO_4$. The solvent was removed under vacuum, and the residue was purified by chromatography (Hexane/EtOAc, 10:1 to 4:1) to give 5 (36 mg, 84%) as a white solid.

$^1H$ NMR (400 MHz, $CDCl_3$); δ 5.34 (dd, J=4.4, 2.0 Hz, 1H), 3.51 (tt, J=11.6, 4.0 Hz, 1H), 2.31-2.05 (m, 4H), 2.01-1.91 (m, 3H), 1.87-1.80 (m, 3H), 1.73-1.66 (m, 2H), 1.60-1.40 (m, 8H), 1.33-1.07 (m, 7H), 1.00 (s, 3H), 0.92 (d, J=6.8 Hz, 3H), 0.68 (s, 3H); $^{13}C$ NMR (100 MHz, $CDCl_3$); δ 140.9, 121.8, 85.3, 71.9, 68.0, 56.9, 56.0, 50.2, 42.6, 42.4, 39.9, 37.4, 36.6, 35.3, 34.9, 32.0, 31.8, 28.3, 24.4, 21.2, 19.5, 18.3, 15.6, 12.0; IR (film): 3302, 2935, 2852, 2334, 1465, 1377, 1135, 1051, 801 $cm^{-1}$; MS (ESI); m/z 353.2 $[M-H]^-$.

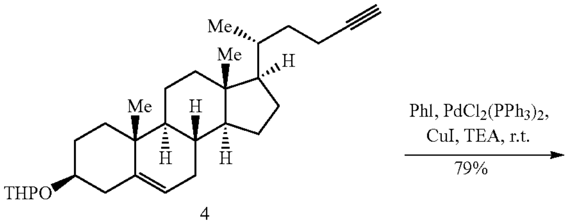

4

-continued

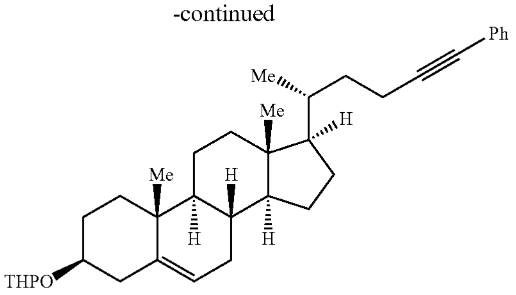

S6

Compound S6. The mixture of $PdCl_2(PPh_3)_2$ (2.2 mg, 0.003 mmol), CuI (0.6 mg, 0.003 mmol), and iodobenzene (7.2 μL, 0.064 mmol) in triethylamine (0.2 mL) was bubbled with Argon gas for ten minutes. To the mixture, triethylamine solution (0.2 mL) of 4 (27.6 mg, 0.063 mmol) was added at room temperature. After stirring for 5 h at room temperature, the reaction was quenched with saturated $NH_4Cl$ aqueous solution and extracted with ethyl acetate. The organic layer was washed with brine, dried over $MgSO_4$. The solvent was removed under vacuum, and the residue was purified by chromatography (Hexane/EtOAc, 40:1) to give S6 (26 mg, 79%) as a white solid.

$^1H$ NMR (400 MHz, $CDCl_3$); δ 7.38 (d, J=5.2 Hz, 2H), 7.27-7.26 (m, 3H), 5.35 (m, 1H), 4.72 (s, 1H), 3.92 (s, 1H), 3.50 (t, J=14.4 Hz, 2H), 2.49-2.17 (m, 4H), 2.03-1.71 (m, 9H), 1.56-1.44 (m, 9H), 1.34-1.04 (m, 9H), 1.01 (s, 3H), 0.98 (d, J=6.8 Hz, 3H), 0.7 (s, 3H); $^{13}C$ NMR (100 MHz, $CDCl_3$); δ 141.2, 141.1, 131.6, 128.3, 127.6, 124.3, 121.7, 97.1, 97.0, 91.0, 80.5, 76.1, 63.1, 63.0, 56.9, 56.0, 50.3, 42.6, 40.4, 39.9, 38.9, 37.6, 37.4, 36.9, 35.5, 35.2, 32.1, 31.4, 29.8, 28.4, 28.1, 25.6, 24.4, 21.2, 20.3, 20.2, 19.5, 18.5, 16.7, 12.0; IR (film); 2942, 2864, 2333, 1492, 1201, 1136, 1024, 972 $cm^{-1}$; MS (ESI); m/z 537.4 $[M+Na]^+$.

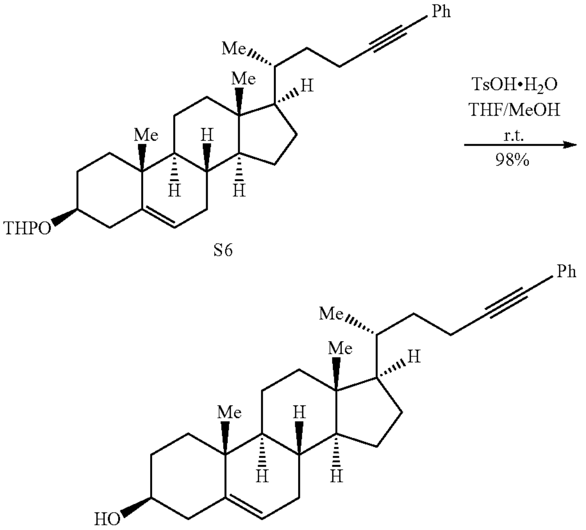

S6

6

Compound 6. S6 (26 mg, 0.05 mmol) and p-toluenesulfonic acid monohydrate (9.5 mg, 0.05 mmol) were dissolved in THF (1 mL) and methanol (1 mL), and stirred under room temperature. After the reaction was complete, the reaction mixture was diluted with ethyl ether, washed with saturated aqueous $NaHCO_3$ solution, and dried with $MgSO_4$. The solvent was removed under vaeuum, and the residue was purified by chromatography (Hexane/EtOAc, 4:1) to give 6 (21 mg, 98%) as a white solid.

$^1H$ NMR (400 MHz, $CDCl_3$); δ 7.38 (d, J=5.6 Hz, 2H), 5.35 (s, 1H), 3.55-3.50 (m, 1H), 2.49-2.20 (m, 4H), 2.04-1.74 (m, 7H), 1.58-1.45 (m, 8H), 1.34-1.08 (m, 7H), 1.01 (s, 3H), 0.98 (d, J=6.4 Hz, 3H), 0.70 (s, 3H); $^{13}$ C NMR (100 MHz, $CDCl_3$); δ 140.9, 131.6, 128.3, 127.6, 124.3, 121.8, 91.0, 80.5, 71.9, 56.9, 56.0, 50.2, 42.6, 42.4, 39.9, 37.4, 37.6, 35.5, 35.2, 32.0, 31.8, 28.3, 24.4, 21.2, 19.5, 18.5, 16.7, 12.0; IR, (film): 2934, 2851, 2325, 1597, 1466, 1376, 1132, 1108, 1040 $cm^{-1}$; MS (ESI): m/z 453.2 $[M+Na]^+$.

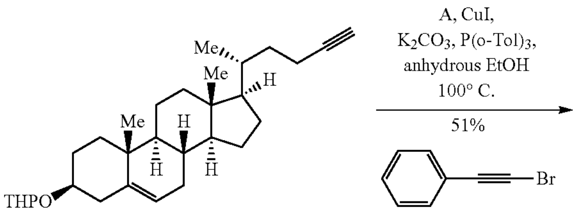

4

A

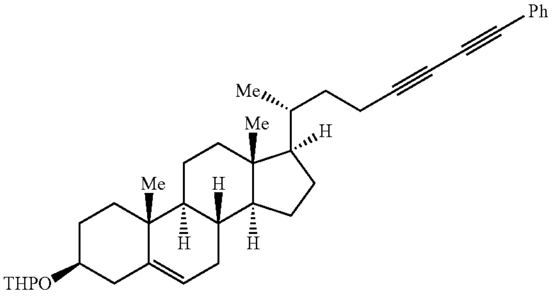

S7

Compound S7. A vial was charged with CuI (1.7 mg, 0.009 mmol), P(o-Tol)$_3$ (5.5 mg, 0.018 mmol), $K_2CO_3$ (24.9 mg, 0.18 mmol), 4 (40 mg, 0.09 mmol), compound A (freshly synthesized according to the literature route,[3] 21.2 mg, 0.117 mmol), and anhydrous EtOH (3 mL). The mixture was stirred for 12 h at 100° C. then cooled to room temperature. The mixture was diluted with EtOAc, filtered through a pad of Celite, and concentrated under vacuo. The residue was purified by Chromatography (Hexane/EtOAc, 20:1) to give S7 (25 mg, 51%) as a white solid.

$^1H$ NMR (400 MHz, $CDCl_3$): δ 7.47 (dd, J=4.0, 2.0 Hz, 2H), 7.35-7.27 (m, 3H), 5.35 (t, J=6.0 Hz, 1H), 4.72 (t, J=4.0 Hz, 1H), 3.56-3.45 (m, 2H), 2.37-2.23 (m, 4H), 2.02-1.94 (m, 2H) 1.86-1.83 (m, 5H), 1.75-1.71 (m, 2H), 1.59-1.44 (m, 10 H), 1.32-1.08 (m, 8H), 1.01 (s, 3H), 0.94 (d, J=6.8 Hz, 3H), 0.70 (s, 3H); $^{13}C$ NMR (100 MHz, $CDCl_3$); δ 141.2, 141.0, 132.6, 128.9, 128.4, 122.3, 121.6, 121.6, 97.1, 97.0, 85.4, 76.2, 74.8, 74.6, 65.0, 63.0, 63.0, 56.9, 56.0, 50.3, 50.3, 42.6, 40.4, 39.9, 38.9, 37.6, 37.4, 36.9, 36.9, 35.4, 34.7, 32.0, 31.4, 29.8, 28.3, 28.1, 25.6, 24.4, 21.2, 20.2, 20.2, 19.5, 18.3, 16.8, 12.0; IR (film): 2938, 2868, 2325, 1508, 1456, 1116, 1026, 755 $cm^{-1}$; MS (ESI): m/z 537.3 $[M-H]^-$.

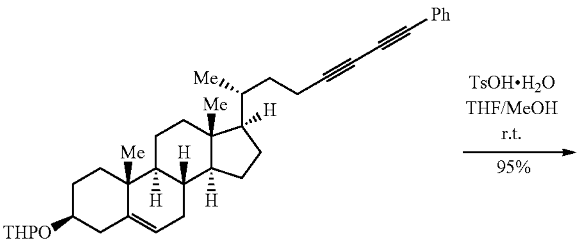

S7

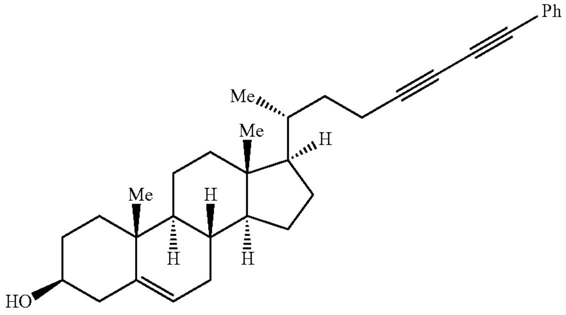

7

Compound 7. S7 (25 mg, 0.046 mmol) and p-toluenesulfonic acid monohydrate (1.70 mg, 0.010 mmol) were dissolved in THF (1 mL) and methanol (1 mL), and stirred under room temperature. After the reaction was complete, the reaction mixture was diluted with ethyl ether, washed with saturated aqueous $NaHCO_3$ solution, and dried with $MgSO_4$. The solvent was removed under vacuum, and the residue was purified by chromatography (Hexane/EtOAc, 4:1) to give 7 (20 mg, 95%) as a white solid.

$^1H$ NMR (400 MHz, $CDCl_3$); δ 7.47 (dd, J=4.0, 2.0 Hz, 2H), 7.33-7.29 (m, 3H), 5.36-5.34 (m, 1H), 3.52 (tt, J=11.2, 4.8 Hz, 1H), 2.44-2.20 (m, 4H), 2.02-1.95 (m, 2H), 1.85-1.71 (m, 4H), 1.59-1.41 (m, 8H), 1.32-1.08 (m, 8H), 1.01 (s, 3H), 0.94 (d, J=6.4 Hz, 3H), 0.70 (s, 3H); $^{13}C$ NMR (100 MHz, $CDCl_3$); δ 141.0, 132.6, 128.9, 128.5, 122.3, 121.8, 85.4, 74.8, 74.6, 71.9, 65.0, 56.9, 56.0, 50.2, 42.6, 42.4, 39.9, 37.4, 36.6, 35.5, 34.7, 32.0, 31.8, 28.3, 24.4, 21.2, 19.5, 18.3, 16.8, 12.0; IR (film): 2925, 2853, 2343, 1465, 1377, 1108, 1059 $cm^{-1}$; MS (ESI): m/z 478 $[M+Na]^+$.

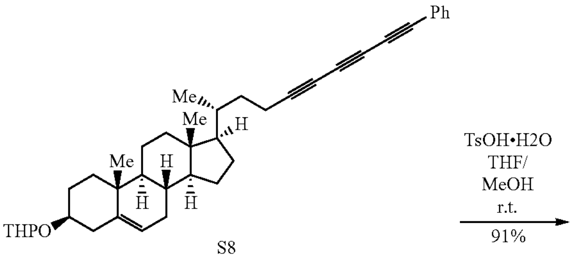

S8

-continued

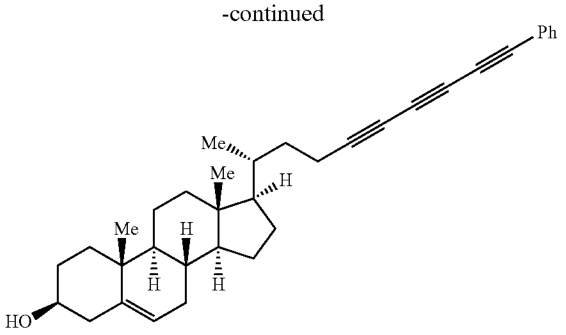

9

Compound 9. S8 (18 mg, 0.033 mmol) and p-toluensulfonic acid monohydrate (6.3 mg, 0.033 mmol) were dissolved in THF (0.7 mL) and methanol (0.7 mL), and stirred under room temperature. After the reaction is complete, the reaction mixture was diluted with ethyl ether, washed with saturated aqueous $NaHCO_3$ solution, and dried with $MgSO_4$, The solvent was removed under vacuum, and the residue was purified by chromatography (Hexane/EtOac, 4:1) to give 8 (14 mg, 91%) as a white solid.

$^1$H NMR (400 MHz, $CDCl_3$): δ 7.50 (d, J=8.0 Hz, 2H), 7.37-7.25 (m, 3H), 5.35 (d, J=4.0 Hz, 1H) 3.55-3.50 (m, 1H), 2.36-2.24 (m, 4H) 2.01-1.98 (m, 2H), 1.85-1.41 (m, 14H), 1.30-1.03 (m, 6H), 1.01 (s, 3H), 0.93 (d, J=6.4 Hz, 3H), 0.69 (s, 3H); $^{13}$C NMR (125 MHz, $CDCl_3$); δ 140.9, 133.1, 129.6, 128.6, 121.8, 121.3, 83.2, 75.5, 74.8, 71.9, 67.6, 65.6, 59.6, 56.8, 55.9, 50.2, 42.6, 42.4, 39.9, 37.4, 36.6, 35.4, 34.4, 32.0, 31.8, 28.3, 24.4, 21.2, 19.5, 18.3, 16.8, 12.0; IR (film): 2932, 2335, 2221, 1488, 1442, 1376, 1052 $cm^{-1}$; MS (ESI); m/z 477.2 $[M-H]^-$.

Solubilization of tagged cholesterol. To solubilize the tared cholesterol molecules, the following procedure was used to prepare a stock solution of 10 mM cholesterol probe molecules. The appropriate amount of cholesterol probe powder was dissolved in 100% ethanol to make a 20 mM solution. The tube was vortexed and then sonicated in bath sonicator for 2 min. The same volume of DMSO was added into the tube, vortexed, and then sonicated in bath sonicator for 2 min. BODIPY-cholesterol was prepared with the same procedure. For SRS imaging and Raman spectral analysis of tagged cholesterol solutions, cholesterol robe molecules were prepared in cyclohexanone, at 50 mM. The tube was vortexed and then sonicated in bath sonicator for 2 min. 1 μL of the solution was taken to prepare cover glass samples immediately before use.

Cell culture and PhDY-Chol treatment. CHO-K1 cells and M12 cells (mutant CHO-K1 cells that contain a deletion of the NPCl locus[39]) were kindly provided by Dr. Daniel Ory, and were grown in a monolayer at 37° C. in 5% $CO_2$ in DMEM/F-12 medium supplemented with 10% (vol/vol) FBS. To incubate cells with PhDY-Chol, cells were pre-incubated in DMEM/F-12 medium supplemented with 4.4% lipoprotein-deficient serum to deplete medium cholesterol for 16 h. The cells were then incubated with PhDY-Chol containing medium (DMEM/F-12+4.4% lipoprotein-delicient serum +50 μM. PhDY-Chol) for 16 h to 24 h. Cells were rinsed with 1× PBS buffer three times before the next procedure.

Raman spectromicroscopy. The background of Raman spectrum was removed as described. Each Raman spectrum of tagged cholesterol solution was acquired in 10 seconds, and each Raman spectrum of fluorescence stained cells was acquired in 30 seconds. On the same microscope. TPEF imaging was performed with 707 nm laser with 100 mW power. Backward-detected two-photon fluorescence signal was collected through a 425/40 nm or 522/40 nm band-pass filter for imaging filipin BODIPY fluorescence, respectively.

SRS microscopy. SRS imaging was performed on a femtosecond SRL microscope, with the laser beating frequency tuned to the C≡C vibration band at 2,252 $cm^{-1}$, or to the C—H vibration band at 2,885 $cm^{-1}$, as described previously. The laser power at the specimen was maintained at 75 mW, and no cell or tissue damage was observed. For off-resonance, 2,099 $cm^{-1}$ was used. On the same microscope. TPEF imaging was performed with 843 mn laser with 30 mW power. Forward-detected two-photon fluorescence signal was collected through an appropriate hand-pass filter for imaging filipin, BODIPY, or LysoTracker.

ACAT-1 inhibition. ACAT-1 inhibition was used to block cholesterol esterification either by adding a potent ACAT inhibitor, avasimibe, or by RNA interference with ACAT-1 shRNA plasmid. Avasimibe: Cells were pre-treated with avasimibe at a final concentration of 10 μM for 24 h. Then PhDY-Chol containing medium with 10 μM avasimibe was added into the cells and incubated for 24 h. RNA interference: RNA interference was employed to specifically inhibit endogenous ACAT-1. The ACAT-1 shRNA plasmid was purchased from Santa Cruz (sc-29624-SH), shRNA plasmid was transfected with Lipofectaminee®2000 (Invitrogen 11668030) as described in the mwinfacturer's protocols.

HPβCD treatment. HPβCD was used as a drug treatment of NP-C disease. M12 cells were incubated with PhDY-Chol for 16 h as described above. Then cells were treated with 500 μM HPβCD for 30 h.

Cell-viability assay. CHO cells were grown in 96-well plates with density of 4000 cells well. The next day, the cells were treated with each cholesterol probe at the indicated concentrations for 48 h. Cell-viability was measured with the MTT colorimetric assay (Sigma).

Propidiun iodide staining. Propidium iodide was used to stain late apoptotic or necrotic cells. CHO cells were incubated with 30 μM of tagged cholesterol molecules for 24 h. The propidium iodide staining was performed following protocols provided by the manufacturer (Life Technologies).

Fluorescent staining of free cholesterol, LDs, and lysosmes. Filipin was used to stain free cholesterol. Cells were fixed with 10% formalin solution (Sigma) for 1 h at room temperature. 1.5 mg/mL glycine in PBS was used to quench the formalin by incubating the fixed cells for 10 minutes at room temperature. To stain the cells with filipin, working solution of 0.05 mg/mL, of filipin in PBS/10% PBS was used to incubate cells for 2 h at room temperature. BODIPY was used to label LDs. Cells were incubated with 10 μg/mL of BODIPY for 30 minutes at room temperature. LysoTracker Yellow-HCK-123 was used to stain lysosomes following protocols provided by the manufacturer (Life Technologies). Cells were rinsed with PBS three times before TPEF imaging.

*C. elegans* strains. The N2 Bristol was used as wild-type strain. VC452 strain with chup-1(gk245) X genotype was used to study PhDY-Chol uptake. VS17 strain with hjIs9 [ges-1p::glo-1::GFP+unc-119(+)] genotype was used to study cholesterol storage in LROs.

PhDy-Chol uptake into *C. elegans*. PhDY-Chol uptake procedure was modified from a previously reported procedures. Briefly, 500 μM of PhDY-Chol DMSO was spread on the NGM plates seeded with an *E. coli* OP50 lawn and allowed to grow overnight at room temperature. *C. elegans* was then transferred to PhDY-Chol containing plates and grown for 3 days before SRS imaging.

Statistical analysis. To quantify PhDY-rich area, we first selected one cell and used "Threshold" function to select PhDY-rich cellular regions using ImageJ. Then, by using "Analyze Particles" function, the area fraction (%) of PhDY-rich region was obtained. To quantify PhDY-rich LDs, "Image Calculator" function in ImageJ was used to multiply SRS image of PhDY-Chol by TPEF image of BODIPY. Then, after using "Threshold" function to select PhDY-rich LDs, the number of PhDY-rich LDs was counted by "Analyze Particles" function. For each group, 7 cells were analyzed, and results were shown as mean±standard deviation (SD). Student's test was used for all the comparisons, $p<0.05$ was considered statistically significant.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A compound with the following formula:

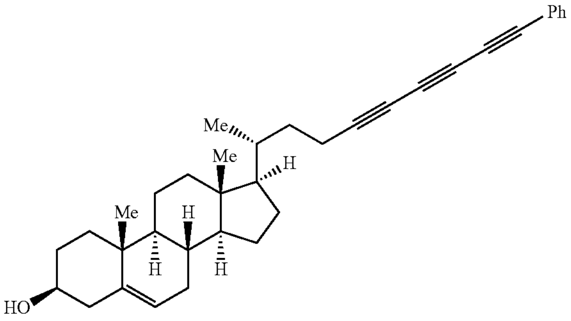

or (7)

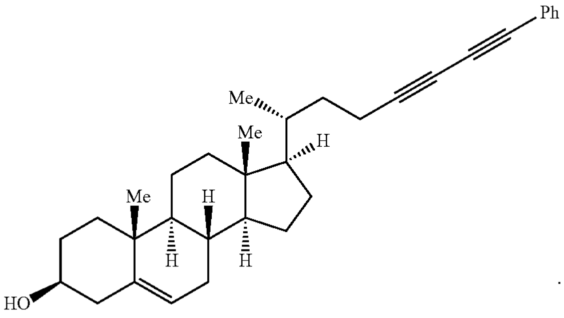

.

PhDY-Chol

2. A method to use the compound of claim 1 to detect cholesterol storage and trafficking in live cells, comprising applying the compound to said live cells and subjecting said live cells to Raman Spectroscopy to identify cholesterol location in said live cells.

3. The compound according to claim 1, wherein the compound is inert.

4. The method according to claim 2, wherein the compound is selectively accumulated in lysosomes in a cellular model of NP-C disease.

5. The method according to claim 2, wherein said compound reacts with Acyl-CoA and ACAT-1 (cholesterol acyltransferase 1) and deposits the resultant ester product in lipid droplets (LDs).

6. A method for screening a lead compound that interfere cholesterol metabolism in live cells, comprising applying the compound in claim 1 with or without said lead compound to said live cells, subjecting said live cells to Raman Spectroscopy and identifying cholesterol storage and localization changes in lead compound treated live cells compared to those not treated cells.

* * * * *